Figure 1:
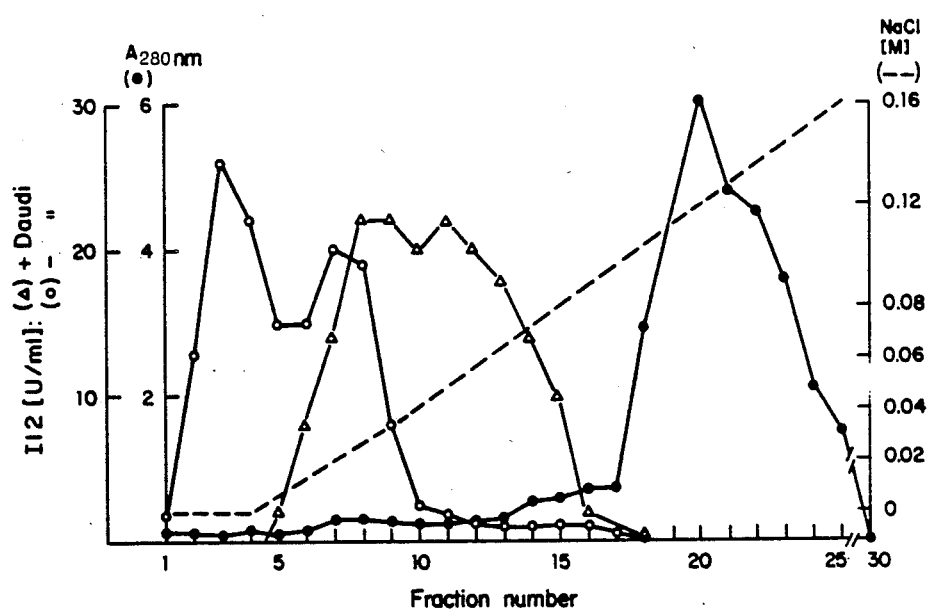

United States Patent [19]

Mertelsmann et al.

[11] Patent Number: 4,908,433

[45] Date of Patent: Mar. 13, 1990

[54] USES OF INTERLEUKIN-2

[75] Inventors: Roland Mertelsmann, Chappaqua; Karl Welte, New York, both of N.Y.; Salvatore Venuta, Napoli, Italy

[73] Assignee: Sloan-Kettering Institute for Cancer Research, New York, N.Y.

[21] Appl. No.: 205,451

[22] Filed: Jun. 10, 1988

Related U.S. Application Data

[60] Division of Ser. No. 603,580, Apr. 25, 1984, Pat. No. 4,778,879, which is a continuation-in-part of Ser. No. 370,223, Apr. 20, 1982, abandoned.

[51] Int. Cl.⁴ .............................................. C07G 7/00
[52] U.S. Cl. ..................................... 530/351; 424/95; 424/101; 514/2; 514/21; 514/885; 530/350
[58] Field of Search ..................... 530/350, 351; 514/2, 514/21, 885; 424/95, 101

[56] References Cited

U.S. PATENT DOCUMENTS

| | | | |
|---|---|---|---|
| 4,315,852 | 2/1982 | Leibowitz et al. | 530/351 |
| 4,390,523 | 6/1983 | Fabricius et al. | 435/68 |
| 4,401,756 | 8/1983 | Gillis | 435/68 |
| 4,448,879 | 5/1984 | Fabricius et al. | 424/85.2 |
| 4,450,103 | 5/1984 | Konrad et al. | 530/351 |
| 4,462,940 | 7/1984 | Hanisch et al. | 530/351 |
| 4,464,295 | 8/1984 | Bhaduri et al. | 530/419 |
| 4,464,355 | 8/1984 | Fabricius et al. | 424/85.2 |
| 4,476,049 | 10/1984 | Kung | 530/351 |
| 4,490,289 | 12/1984 | Stern et al. | 530/351 |
| 4,508,833 | 4/1985 | Sonneborn et al. | 530/351 |
| 4,511,502 | 4/1985 | Builder et al. | 530/417 |
| 4,511,503 | 4/1985 | Olson et al. | 530/422 |
| 4,512,922 | 4/1985 | Jones et al. | 530/408 |
| 4,518,584 | 5/1985 | Mark et al. | 424/85.2 |
| 4,530,787 | 7/1985 | Shaked et al. | 530/351 |
| 4,564,593 | 1/1986 | Tsukamoto et al. | 435/91 |
| 4,569,790 | 2/1986 | Koths et al. | 530/351 |
| 4,572,798 | 2/1986 | Koths et al. | 530/351 |
| 4,675,383 | 6/1987 | Bohlen et al. | 530/351 |
| 4,738,927 | 4/1988 | Taniguchi et al. | 435/243 |
| 4,778,879 | 10/1988 | Mertelsmann et al. | 530/351 |
| 4,789,658 | 12/1988 | Yoshimoto et al. | 514/2 |

FOREIGN PATENT DOCUMENTS

| | | |
|---|---|---|
| 0088195 | 9/1983 | European Pat. Off. |
| 0091539 | 10/1983 | European Pat. Off. |
| 0092163 | 10/1983 | European Pat. Off. |
| 0094317 | 11/1983 | European Pat. Off. |
| 0111344 | 6/1984 | European Pat. Off. |
| 0118617 | 9/1984 | European Pat. Off. |
| 0118977 | 9/1984 | European Pat. Off. |
| 0119621 | 9/1984 | European Pat. Off. |
| 0121352 | 10/1984 | European Pat. Off. |

(List continued on next page.)

OTHER PUBLICATIONS

Stötter, Hans and Rude, E., Fur. J. Immunol. 1980, 10 pp. 719-722.

(List continued on next page.)

Primary Examiner—John Kight
Assistant Examiner—Carlos Azpuru
Attorney, Agent, or Firm—John P. White

[57] ABSTRACT

Interleukin 2 (IL 2; T-cell growth factor), produced with and without costimulation by Burkitt's lymphoma line Daudi, is highly purified approximately over 37,000-fold to apparent homogeneity from lymphocyte-conditioned medium derived from normal human blood cells by $(NH_4)_2SO_4$-precipitation, ion exchange chromatography, gel filtration and hydrophobic chromatography, hp IL-2 is free of pyrogens, B cell inducing factor, B cell growth factor, interferon, CSF, and thymocyte differentiating factor. Nature IL 2 produced in the absence of Daudi cells has a molecular weight of about 26,000 daltons as measured by gel filtration and yields Il 2 having two molecular weights of about 16,000 and 17,000 daltons after denaturation as measured by sodium dodecyl sulfate-poylacrylamide gel electrophoresis, IL 2 produced in the presence of Daudi cells shows a molecular weight of approximately 14,500 daltons as measured by both gel filtration and sodium dodecyl sulfate-polyacrylamide gel electrophoresis.

21 Claims, 11 Drawing Sheets

FOREIGN PATENT DOCUMENTS 0128467 12/1984 European Pat. Off. .
0132359 1/1985 European Pat. Off. .
0142268 5/1985 European Pat. Off. .
0145390 6/1985 European Pat. Off. .
0147819 7/1985 European Pat. Off. .
0158198 10/1985 European Pat. Off. .
0158487 10/1985 European Pat. Off. .
0148098 11/1980 Japan .

OTHER PUBLICATIONS

Kawamura Hajime and Rosenberg, Steven A., Journal of Experimental Medicine, 1985, Immunizat. with Ag and IL-2 in Vivo Overcomes Ir Gene Low Responsiveness 162.381–86.
Farrar, John J. et al., Immunol. Review (1982), 63.158–160 Bioch, Biol, & Role of Il-2 in the Induction of Cyt T-Cell & Ab Forming B Cell Responses.
Ruscetti, F. and Gallo, R., *Blood*, vol. 57, no. 3, pp. 379–394 (1981).
Reed, S., et al., *J. Immunol.*, vol. 133, no. 6, pp. 3333–3337 (1984).
Riendeau et al., *J.B.C.*, (1983), 258(20):12114–12117.
Taniguchi et al., *Nature*, (1983), 302:305.
Robb, R. J., *Immunology Today*, (1984), 5(7):203.
Rosenburg, S. A., *Science*, (1984), 223:1412
Stern, A.S., et al., *Proc. Natl. Acad. Sci.* (U.S.A.), (1984), 81:871–875.
Wang, Alice, et al., *Science*, 224:1431–1433.
"Chromatographic Removal of Pyrogens", *Bio/Technology*, Dec. 1984, 1035–1038.
Lahm et al., *J. of Chromatography*, (1985), 326:357–361.
Rosenberg et al., *New England Journal of Medicine*, (1985), 313:1485–1492.
Mier, et al., *J. Immunol.*, vol. 128, no. 3 pp. 1122–1127 (1982).
Welte, K., et al., *J. Exp. Med.*, (1982), 156:454–464.
*Lymphokine Res.*, (1982), I(2), FASEB Editorial.
Coughlin, R. T., et al., *Federation Proceedings*, (1983), 42(7):2022.
Devos et al., *Nucleic Acid Res.*, (1983), 11(13):4307.
Henderson et al., *J. Immunol.*, (1983), 131(2):810–815.
Milstone et al., *Biochem, Biophy, Res. Comm.*, (1983) 115(3):762–768.
Mochizuki et al., *J. Immuno. Meth.*, (1980), 39:185–201.
Henriksen et al., *Cell Immunol.*, (1982), 73:106–114.
Ihle et al., *J. Immunol*, (1982), 129(6):2431.
Watson, et al., *J. Exp. Med.*, (1979), 150:849–861.
Derynck et al., *Nature*, (1980), 287:193–197.
Gillis et al., *J. Immunol.*, (1980) 124:1954–1962.

USES OF INTERLEUKIN-2

This invention was made with support in part under Grants CA 08748, CA 22507, CA 25608, CA 20194, CA 21525, CA31525, PO1-CA-20194, AI 18 321-01, CA 23766 and CA 33050 awarded by the National Cancer Institute, National Institute of Health, DHEW. The government has certain rights in this invention.

This application is a divisional of U.S. Ser. No. 603,580, filed Apr. 25, 1984, now U.S. Pat. No. 4,778,879, issued Oct. 18, 1988, which in turn is a continuation-in-part of U.S. Ser. No. 370,223, filed Apr. 20, 1982, now abandoned. The contents of U.S. Pat. No. 4,778,879 are hereby incorporated by reference into the subject application.

Human interleukin 2 (IL 2; T-cell growth factor), produced in normal human blood with and without costimulation by Burkitt's lymphoma line Daudi, is purified approximately 37,000-fold to apparent homogeneity from lymphocyte-conditioned medium by $(NH_4)_2SO_4$-precipitation, ion-exchange chromatography (diethylaminoethyl cellulose), gel filtration (AcA 44 Ultrogel), and hydrophobic chromatography, preferably on Blue Agarose and on Procion$^R$-Red Agarose. IL2 can also be separated from B cell growth factor (BGF) and B cell inducing factor (BIF) by hydrophobic chromatography or by a further step using high pressure liquid chromatography preferably in reverse phase. BIF is also known as T-cell replacing factor. (See Table I)

TABLE I
Purification of Human Interleukin 2

| Fraction | Total Protein (mg) | Total Activity (U) | Specific Activity (U/mg protein) | Purification (fold) | Yield (%) |
|---|---|---|---|---|---|
| I Ly—CM+ | 10,800 | 297,000 | 27 | 1 | 100 |
| II $(NH_4)_2SO_4$-precipitate | 9,000 | 247,000 | 27 | | 84 |
| III DDAE cellulose(DE 52) | 135 | 183,000 | 1,356 | 50 | 62 |
| IV AcA 44 Ultrogel | 40 | 145,000 | 3,625 | 135 | 49 |
| V Blue Agarose | 0.96 | 87,680 | 91,333 | 3,382 | 30 |
| VI Procion$^R$-Red Agarose* | 0.055++ | 55,229 | 1,004,164 | 37,191 | 19 |

+The IL 2 activity in the Ly—CM (lymphocyte-conditioned medium) was 100 U/ml.
++Protein concentration was determined by densitometric comparison of the protein content in the samples with known amounts of protein standards as detailed herein.
*Use of HPLC is limited to those samples where there is incomplete separation and/or trace materials are present.

Native IL 2 produced in the absence of Daudi cells has a molecular weight of about 26,000 daltons as measured by gel filtration and yields IL 2 having two molecular weights of about 16,000 and 17,000 daltons after denaturation as measured by sodium dodecyl sulfate-polyacrylamide gel electrophoresis. IL 2 in the presence of Daudi cells ($10^6$/ml) shows a molecular weight of approximately 14,500 daltons as measured by both gel filtration and sodium dodecyl sulfate-polyacrylamide gel electrophoresis.

This highly purified IL 2 shows a specific activity of about $10^6$ U/mg protein which appears to be independent of molecular weight and an isoelectric point of approximately pH 6.7 for the 26,000 MW form and about pH 8.1 for the 14,500 MW variant.

The highly purified IL 2 lacks detectable Interferon (alpha and gamma), granulocyte-macrophage colony-stimulating factor (CSF), T-cell replacing factor (TRF of BIF), B cell growth factor (BCGF) and thymocyte differentiating activity, and was free of any contaminating proteins as judged by silver staining and by $I^{125}$ exolabelling in sodium dodecyl sulfate-polyacrylamide gel electrophoresis. It is also pyrogen-free as tested in rabbits. In this test doses of purified IL 2 were used comparable to the clinical doses tried (see below). Tests were done in 3 rabbits/dose and little or no temperature rise is effected (Liberco Testing Corp, Roselle Park, NJ 07204 USP-XX). All four molecular forms of IL 2 were biologically active at concentrations of $10^{-11}$–$10^{-10}$ M (0.2±0.05 U/ml), supporting the growth of human and murine cytotoxic T-cell lines.

In recent years, several functionally and biochemically unique soluble proteins have been discovered that play a central role in regulating the responsiveness of the immune system and/or act as antigen-non-specific effector molecules capable of mediating one or more aspects of immune function. Most of these factors are synthesized by hemopoietic cells, especially lymphoid cells and monocytes, and are generally termed cytokines. Recent refinements in protein chemistry and separation techniques, and the development of continuous cell lines secreting particular cytokines, have made detailed cytokine analysis possible.

It was discovered that many of the cell interactions involved in the afferent arm of immune responses involved soluble helper or suppressor substances elaborated by these cells. These non-antibody mediators produced by lymphocytes and other cells generated a degree of interest comparable to that previously only given to antibodies themselves.

Today, there is hardly any area of the immune response concerning which cytokine action has not been demonstrated or inferred.

Soon after the discovery that plant lectins stimulated the proliferation of human T-lymphocytes, soluble mitogenic factors were found in the culture supernatants. Since 1965, many such mitogenic factors have been described, and, depending upon the assay used, as many different names and acronyms were applied to the activities.

In 1976, it was reported that conditioned media from lectin-stimulated mononuclear cells contained a mitogenic factor that would support the continuous exponential growth of lectin-activated human T-cells. This discovery allowed for the construction of a rapid, quantitative assay for the T-cell growth factor (TCGF, IL 2), in that the growth of the cultured T-cells was entirely dependent upon an exogenous supply of IL 2. Within 24 hours, sigmoid IL 2 dependent dose-response curves, which were amenable to probit analysis, yielded reproducible, quantitative data, such that a comparison of IL 2 titers was possible. The development of an IL 2 assay, which was rapid, simple and quantitative, prompted experiments to define its biochemical characteristics. As a result, it is now clear that IL 2 provides the mitogenic stimulus after lectin or antigen initiated T-cell activation. The addition of a lectin or antigen to mononuclear cells results in at least three responses: first, release of a soluble factor from monocytes/macrophages (IL 1); second, under the influence of this monokine, the release of IL 2 by a specific T-cell subset; and third, expression of IL 2 receptors and binding to IL 2 to its receptor in a proliferative response. While these responses all require initiation by lectins or antigens, the proliferative response is mediated solely by IL 2.

Interleukin 2 (IL 2, T-cell growth factor), discovered by Morgan et al. [Morgan, D. A., et al., (1976) Science 193:1007] is produced by T-lymphocytes after antigen- or mitogen-stimulation and is required for proliferation of activated T-cells. IL 2 is an essential mediator of the immune response [Paetkau, V., (1981) Nature 294:689; Ruscetti, F. W., et al. (1981) Blood 47:379] and there is preliminary evidence that it may also be responsible for the abnormal cell proliferation in human lymphoblastic leukemias [Gillis, S., et al. (1980) AACR, Abstract No. 955, p. 238; Venuta, S., et al. (1983) Blood 61:781].

These observations have led investigators to initiate antigen-specific proliferative responses, followed by attempts to maintain functional, antigen-specific T-cells in continuous IL 2-dependent proliferation culture. The ability to culture functional monoclonal T-cells should provide the cellular reagents necessary for detailed studies of the nature of the T-cells immune response. The cultured T-cells have also provided the cellular reagents necessary for detailed studies of IL 2 cellular interaction.

Results of experimentation indicate that IL 2 satisfies most of the criteria for a hormone. It is produced by a distinct cell type and acts at a distance on other cell types by means of specific receptors. Study of the molecular mechanisms of IL 2 production, hormone-receptor interaction, and the identification of IL 2 agonists and antagonists should provide new insights into pathological disease states which involve T-lymphocytes.

Studies of the mechanism of action of IL 2 using unpurified or partially purified preparations have been very difficult because conditioned media contain other lymphokines and cytokines with potent biological activities. Several groups have reported purification procedures for both murine [Watson, J., et al. (1979) J. Exp. Med. 150:849; Granelli-Piperno, A., et al. (1981) J. Exp. Med. 154:422] and human IL 2 [Mier, J. W., et al. (1980) Proc. Nat'l. Acad. Sci. U.S.A. 77:6134; Gillis, S., et al. (1980) J. Immunol. 124:1954; Robb, R. J., et al. (1981) Mol. Immunol. 18:1087]. These IL 2 preparations have permitted an increasingly better definition of IL 2 regulation.

The work of Granelli-Piperino et al. Supra involves mouse IL 2 which is not active in humans and, differs in molecular weight and isoelectric point from human IL 2. It is noted that the method of preparation and/or purification of mouse IL 2 differs from that of the present invention. Granelli et al. use preparative electrophoresis.

The work of Mier et al. [J. Immunology (1982) 128:1122] uses preparative gel electrophoresis so differs from the invention detailed herein. No use of Sendai virus or Daudi cells is found in Mier et al and the disclosed molecular weight is 13,000. The Mier et al. reported purification factor was 800 fold is compared to the present work which purifies IL 2 over 37,000 fold. Also note the specific activity of IL 2 is a fraction of that obtained in the invention. No work in humans is reported.

The work of Gillis et al. [(1980) J. Immunol. 124:1954] uses a simple method to prepared IL 2 containing fractions differing from the extensive preparative method of the invention. Also, the work is dependent on Daudi cell stimulation. No sendai viral stimulation is used. The molecular weight of Gillis et al. is of the first impression. No work in humans is shown in Gillis et al. The majority of the Gillis et al. evidence for IL 2 is . . . admittedly generated from murine systems . . ." (p. 1960).

The work of the invention contains information from several papers which are hereby incorporated by reference as follows:
(1) Ciobanu, Niculae et al. (1983) J. Clin. Immunol. 3:332.
(2) Mertelsmann, Roland et al. (1983) in Normal and Neoplastic Hematopoiesis pp. 545–555 Alan R. Liss, New York
(3) Welte, Karl et al. (1982) J. Exp. Med., 156:454.
(4) Flomenberg, W., et al. (1983) J. Immunol. 130:2644.
(5) Merluzzi, Vincent et al. (1983) J. Immunol. 131:806.
(6) Venuta, S., et al. (1983) *Blood* 61:781.
(7) Welte, K., et al. (1984) *Blood* in press.

In the course of purification of the highly purified human IL 2 of the invention, several reproducible conditions for the production of high levels of human IL 2 have been previously developed. First, nylon-column purified peripheral blood lymphocytes prepared from many allogeneic donors were cultured for 72 hours at $4 \times 10^6$ cells/ml in the presence of 1% phytohemagglutinin-M and a 0.25% bovine serum albumin. In general, phytohemagglutinin-stimulated leukocytes from a single donor produce much lower levels of IL 2. Second is a method that relies on the use of phytohemagglutinin-stimulated cells from a single donor but co-cultivated with x-irradiated cells from a B-lymphoblastoid cell line such as RM-1, SR, or Daudi. The rationale for use of B-cell lines was to provide a standard source of allogeneic stimulation and thus eliminate the need for mixing several allogeneic donors. Third, after screening for cell lines that will release IL 2 after mitogen stimulation, a human T-leukemic cell line Jurkat was found to be a high producer. This cell line has since been used by many investigators as a consistent source of IL 2. Tumor promotors have also been used as costimulators, leading to high IL 2 concentrations in the conditioned media, but these preparations would certainly be difficult to use in humans because of the potentially increased risk of cancer promotion.

In the past, IL 2 has been induced as crude lymphocyte-conditioned medium by any of the three methods previously described and prepared under serum-free conditions with bovine serum albumin (0.2%) as the serum replacement.

After ultrafiltration, the crude lymphocyte-conditioned medium was concentrated by $(NH_4)_2SO_4$ fractionation and then dialyzed. The dialyzed active sample was passed over an anion-exchange chromatographic column (diethylaminoethyl-Sepharose). IL 2 activity eluted as a broad peak centered at approximately 0.07M NaCl. Subsequent gel filtration with an Ultrogel AcA 54 column separated the IL 2 from most of the detectable proteins, and this sequence of steps achieved more than a 400-fold increase in specific activity over the IL 2 in the serum-free lymphocyte-conditioned medium. The IL 2-containing material was further purified using polyacrylamide gel electrophoresis containing sodium dodecyl sulfate. The IL 2 activity corresponded to a pair of protein bands present in the 13,000 molecular weight region in the sodium dodecyl sulfate gel. This procedure has been reported by Mier et al. (1982) Supra and Frank et al., (1981) J. Immunol. 127:2361, for the purification of human IL 2. More recently the use of phenylsepharose has been introduced as a first step in the purification scheme of IL 2 [Stadler et al., (1982) J.

Immunol. 128:1620]. However, since phenylsepharose as hydrophobic absorption chromatography was used only in the first step of purification, the major advantages of this technique for separation of multiple lymphokines were not utilized (see below).

Thus although reports are known of purification procedures for both murine and human IL 2, and these preparations have permitted an increasingly better definition of IL 2 regulation, the purity of such preparations has not been well-documented.

We recently found that hydrophobic absorption chromatography following other separation means permits the purification of human IL 2 to apparent homogeneity. A 37,000-fold high purification may be achieved compared to the 60-fold purification reported by Stadler et al. (1982) Supra and the 800-fold purification disclosed by Mier et al., (1982) Supra. Our purified IL 2 preparation is apparently free of all other lymphokines and factors present in the crude lymphocyte-conditioned medium, including Interferon (alpha and gamma), colony stimulating factor (CSF), B-cell growth factor (BCGF), serum thymic factor (FTS) and B cell inducing factor (BIF or T-cell replacing factor).

The highly purified IL 2 obtained by us appears to be free of any contaminating proteins in sodium dodecyl sulfate-polyacrylamide gel electrophoresis after staining with a silver nitrate method [Merril, C. R., et al. (1979) Proc. Nat'l. Acad. Sci. U.S.A. 76:4335], and after exolabelling with $I^{125}$ [Branca, A. A. et al., (1981) Nature 294:768; Bio-Rad (Rockville Center, New York) Technical Bulletin 1071 Iodinating Proteins with Enzymobeads (May 1981) which references are hereby incorporated by reference].

Up to three functionally active bands were detected in this preparation. Elution of the materials from the sliced gels possessed high specific activity. We found that the molecular species of IL 2 are dependent on the experimental conditions used for IL 2 induction. All purification steps have been developed to allow large scale production and are currently being used for 10 liters of conditions medium per week.

Although this purification protocol has been successfully used not only for IL 2 from normal lymphocytes, but also for IL 2 from leukemic lymphoblasts as well as from the Jurkat cell line, our work has focused predominantly on IL 2 from normal human lymphocytes. Since the pure material was intended for use in humans, leukemic cell sources as well as induction conditions using tumor promoters [Frank et al., (1981) J. Immunol. 127:2361; Stadler et al., (1982) Supra. Stern, A., et al. (1984) Proc. Nat'l. Acad. Sci. 81:871 and European patent application E P No. 0089062 by Ajinomoto] and/or tumor cell line costimulators [Gillis et al., (1980), J. Immunol. 124:1954] appeared highly undesirable for this purpose. Furthermore, there is the possibility that the leukemic IL 2 might be different from normal IL 2 which, although unlikely, would be an additional hazard for in vivo administration. Robb, R. J., et al. [Proc. Nat'l. Acad. Sci. U.S.A. (1983) 80:5990] at 5993 note such a difference since a structural feature of the IL 2 molecule recognized by specific antibody is absent or masked on most IL 2 secreted by normal human lymphocytes.

Obtaining highly purified human IL 2 according to the invention comprises conditioning the source medium to increase the IL 2 content thereof; concentrating the proteinaceous components of the medium by precipitating same and separating therefrom unprecipitated non-proteinaceous material and smaller molecules (e.g., MW less than 5,000), such as amino acids and small peptides; removing extra salts from the proteinaceous material via dialysis; separating some of the non-specific proteins from desired proteinaceous material by anion exchange; effecting separation by molecular weight of the IL 2-containing proteinaceous material by gel filtration; and separating IL 2, which is highly hydrophobic, from other lymphokines of about the same molecular weight via hydrophobic chromatography. Further purification of IL 2 is achieved using high pressure liquid chromatography to insure removal of B-cell growth factor (BGF) and B cell introducing factor (BIF) also known as T-cell replacing factor, in those batches where the factor(s) dose not completely separate out after hydrophobic chromatography. HPLC also removes trace impurities.

FIG. 1 relates to diethylaminoethyl cellulose (DE 52) chromatography of IL 2. A dialyzed sample of the $(NH_4)_2SO_4$-precipitate fraction was loaded on the DE 52 column. Proteins were eluted with a linear gradient of NaCl (0–0.3M) in 0.05M Tris-HCl (pH 7.8) and 5 ml fractions collected (absorbtion at 280 nm (filled circles), IL 2 (U/ml) produced in the presence (blank triangles) or absence (0—0) of Daudi cells).

Figure 2:
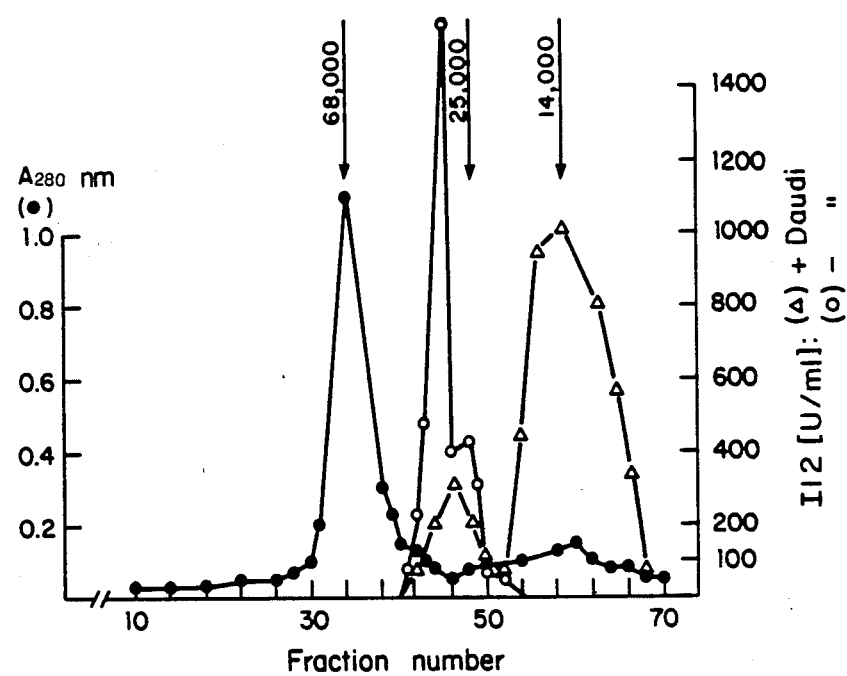

FIG. 2 concerns gel filtration of IL 2 on AcA 44 Ultrogel. DE 52-purified IL 2 was loaded on an AcA 44 Ultrogel column and eluted with phosphate-buffered saline (pH 7.2)/0.1% polyethyleneglycol (MW 6000). Six ml fractions were collected. The column was calibrated with bovine serum albumin (MW 68,000), chymotrypsinogen (MW 25,000), and ribonuclease A (MW 14,000) (absorption at 280 nm (filled circles), IL 2 (U/ml) produced in the presence (blank triangles) or absence (0—0) of Daudi cells).

Figure 3:
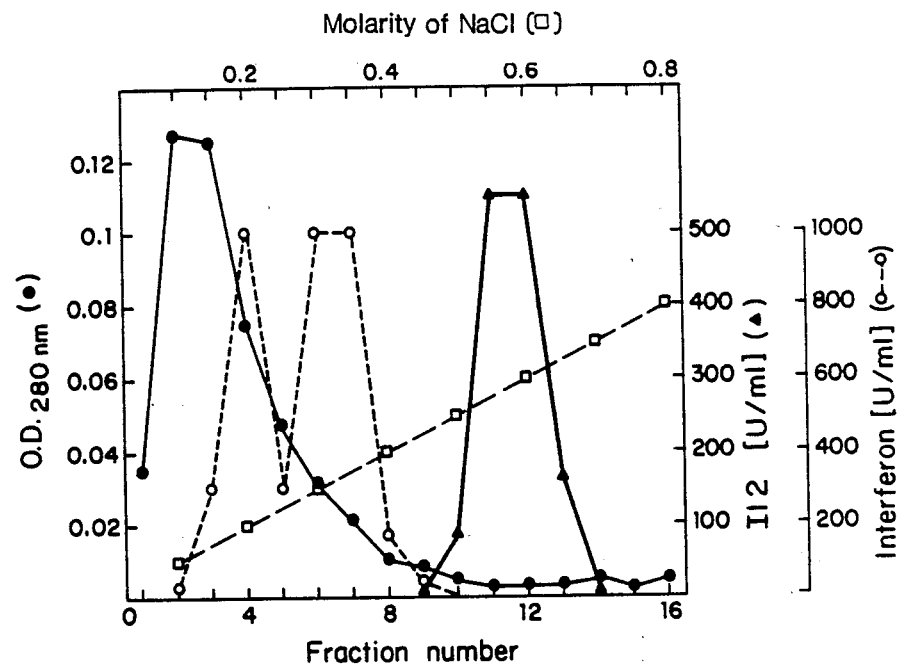

FIG. 3 illustrates chromatography of IL 2 on Blue Agarose. AcA 44 Ultrogel-purified IL 2 was applied to a Blue Agarose column and eluted with a linear gradient of phosphate-buffered NaCl (0.05–0.8M). Twenty ml fractions were collected (O.D. at 280 nm (filled circles), IL 2 (U/ml) (filled triangles), alpha-Interferon (U/ml) (0—0), NaCl molarity (M) (blank squares)).

Figure 4:
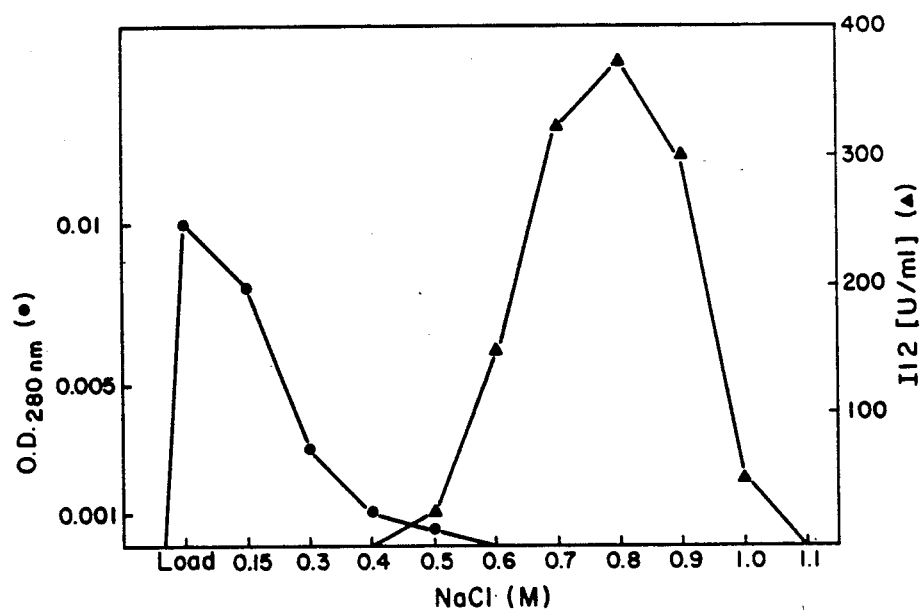

FIG. 4 relates to chromatography of IL 2 on Procion$^R$-Red Agarose. The IL 2-containing fractions from Blue Agarose were pooled and loaded on a Procion$^R$-Red Agarose column. The bound proteins were eluted with a stepwise increase in salt concentration (0.15–1.0M NaCl in phosphate buffer) (O.D. at 280 nm (filled circles), IL 2 (U/ml) (filled triangles)).

Figure 5:
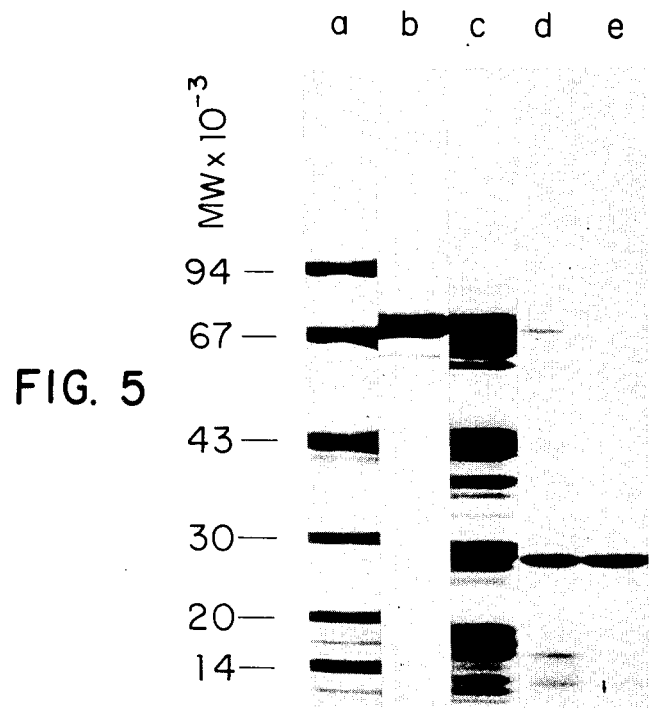

FIG. 5 illustrates a sodium dodecyl sulfate-polyacrylamide gel electrophoresis profile of various steps of IL 2 purification ((a) molecular weight standards: phosphorylase b (MW 94,000), bovine serum albumin (MW 68,000), ovalbumin (MW 43,000), carbonic anhydrase (MW 30,000), soybean trypsin inhibitor (MW 20,000), and alpha-lactalbumin (MW 14,500); (b) IL 2-containing lymphocyte-conditioned medium; (c) dialyzed ammonium sulfate precipitate; (d) pool of IL 2-containing diethylaminoethyl cellulose eluate; (e) IL 2-containing fractions pooled from AcA 44 Ultrogel gel filtration).

Figure 6:
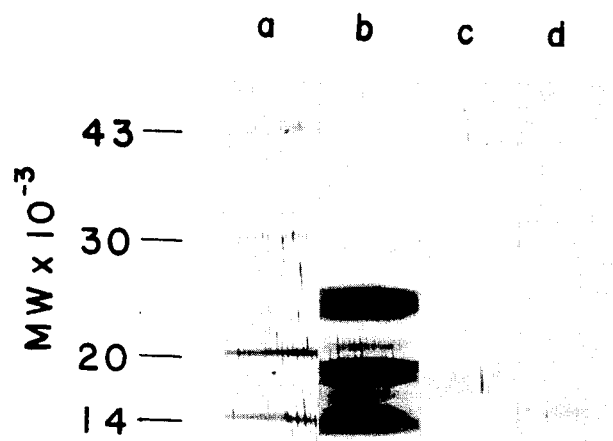

FIG. 6 shows the sodium dodecyl sulfate-polyacrylamide gel electrophoresis of Blue Agarose-and Procion$^R$-Red Agarose-purified IL 2. IL 2 was treated with 2% sodium dodecyl sulfate and 5 mM 2-mercaptoethanol and applied to a 5–20% gradient gel. The protein bands were visualized by a silver nitrate method. The following marker proteins (200 ng each) were used: ovalbumin (MW 43,000), carbonic anhydrase (MW 30,000), soybean trypsin inhibitor (MW 20,000) and alpha-lactalbumin (MW 14,500) ((a) protein standards; (b) Blue Agarose-purified IL 2 produced in the absence of Daudi cells; (c) Procion$^R$-Red Agarose-purified IL 2 prepared in the absence of Daudi cells; (d) Procion$^R$-Red Agarose-purified IL 2 obtained by costimulation with Daudi cells).

Figure 7:
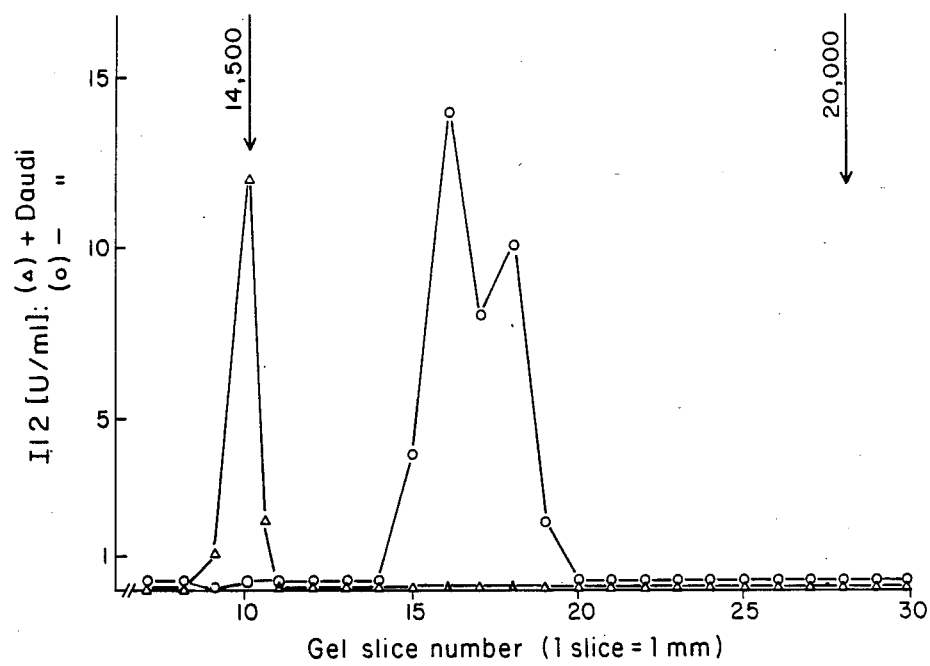

FIG. 7 shows the IL 2 activity of 1 mm gel slices after sodium dodecyl sulfate-polyacrylamide gel electrophoresis of Procion$^R$-Red Agarose-purified IL 2 produced in the presence or absence of Daudi cells. The IL 2 preparations were treated with 2% sodium dodecyl sulfate and 5 mM 2-mercaptoethanol and applied to a 15% polyacrylamide gel. After electrophoresis, the gel was sliced into 1 mm sections and proteins eluted with 0.3 ml phosphate-buffered saline (pH 7.2). The eluted material was assayed for IL 2 activity. The arrows indicate the position of the protein standards soybean trypsin inhibitor (MW 20,000) and alpha-lactalbumin (MW 14,500) (IL 2 (U/ml) produced in the presence (blank triangles) or absence (0—0) of Daudi cells).

Figure 8:
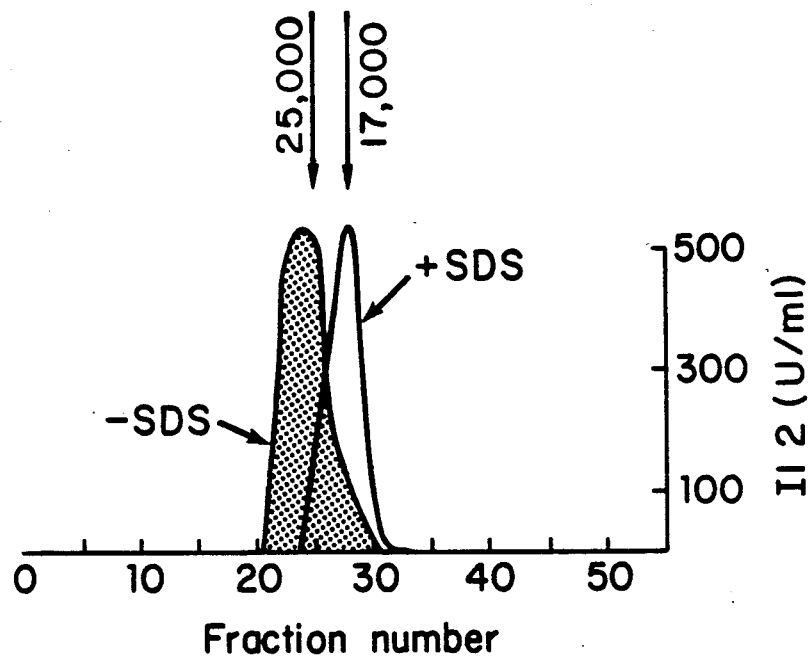

FIG. 8 relates to the gel filtration chromatography of Blue Agarose-purified IL 2 on high performance liquid chromatography in the presence and absence of sodium dodecyl sulfate and dithiothreitol. IL 2, native or treated with 1% sodium dodecyl sulfate and 10 mM dithiothreitol, was applied to a high performance liquid chromatography gel filtration column. The following protein standards were used: bovine serum albumin (MW 68,000), ovalbumin (MW 43,000), chymotrypsinogen (MW 25,000), and ribonuclease and (MW 14,000). The arrows indicate the position of chymotrypsinogen and the calculated 17,000 daltons molecular weight region. The dotted area identifies the position of native IL 2 and the second peak corresponds to the sodium dodecyl sulfate-denatured IL 2.

Figure 9:
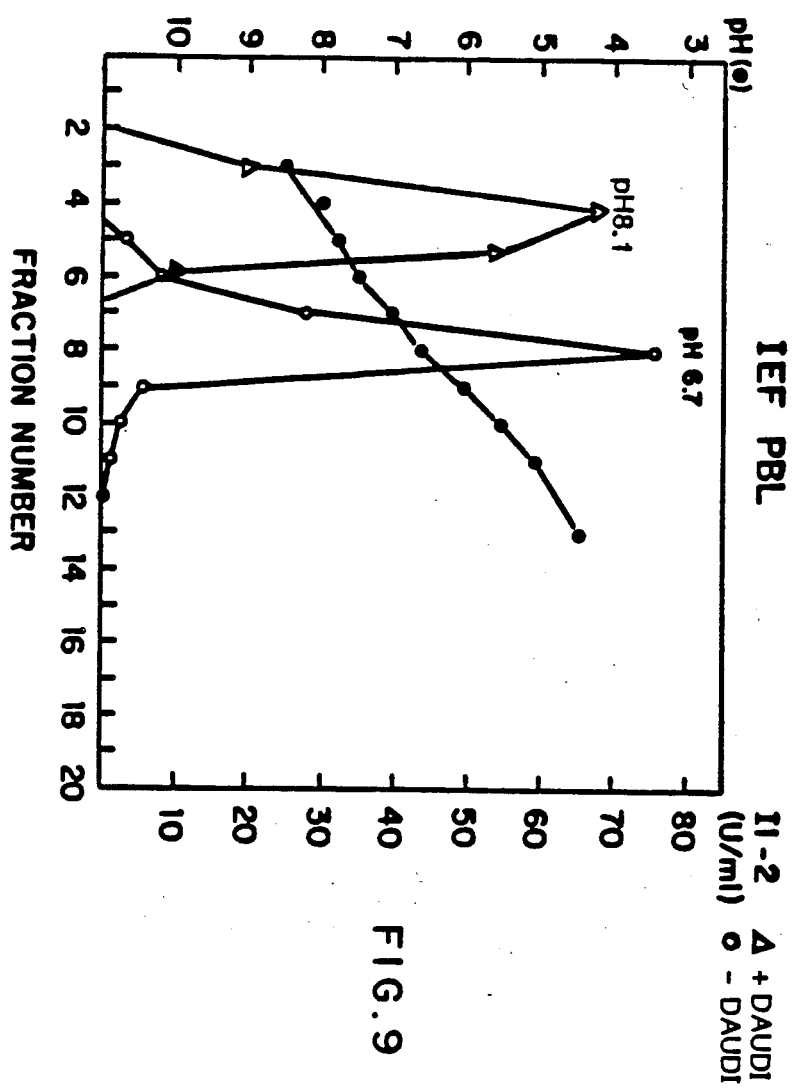

FIG. 9 concerns the isoelectrofocusing of AcA 44 Ultrogel-purified IL 2. An isoelectrofocusing column (110 ml) was prepared by loading a 5–60% glycerol density gradient containing 2% Ampholines of pH 3.5–10. IL 2 eluted from AcA 44 Ultrogel was supplemented with 2% Ampholines (pH 3.5–10) and 20% glycerol and was layered onto the isodense region of the column gradient. Constant power was then applied to the column with a terminal voltage of 2000 V and a current of 5 mA (24 hr, 4° C.) (IL 2 (U/ml) in the presence (open triangles) or absence (0—0) of Daudi cells, pH gradient (filled circles)).

Figure 10:
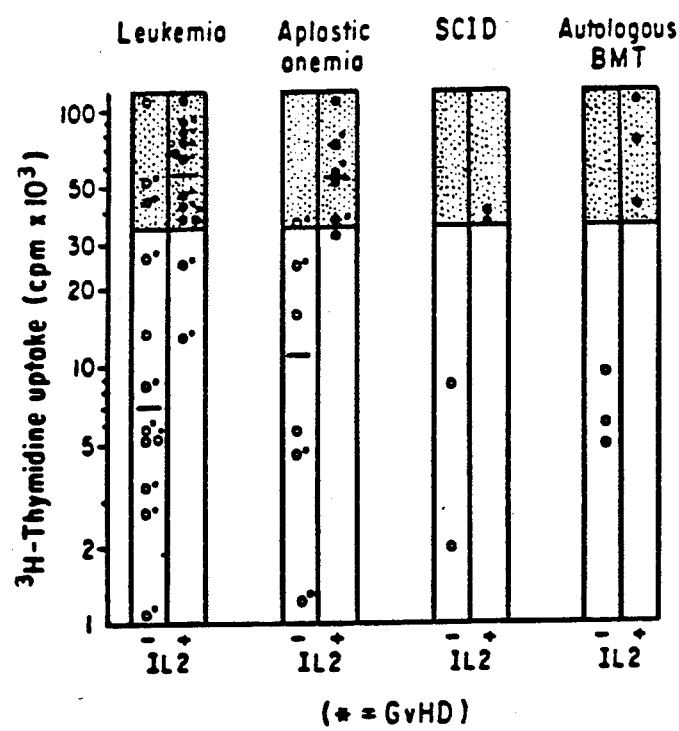
Figure 11:
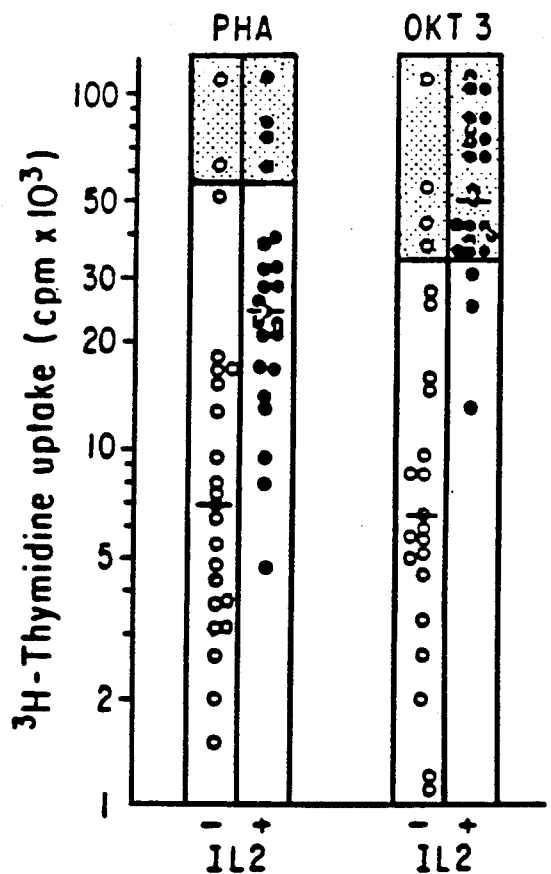
Figure 12:
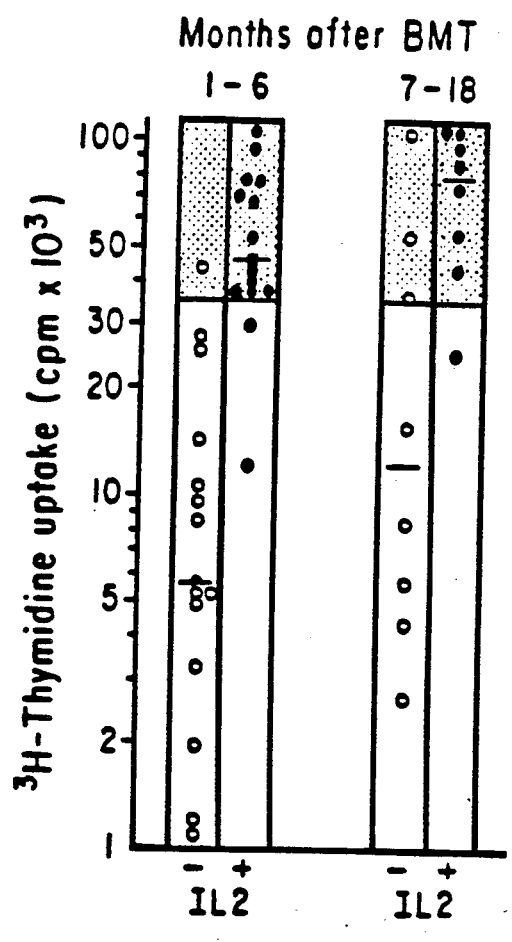

FIG. 10–12 follows thymidine uptake in patients with SCID, leukemias and bone marrow transplants.

The examples below are means to illustrate the invention without limiting it.

Preparation of Lymphocyte-Conditioned Medium
(Fraction I)

Human lymphocytes were obtained from peripheral blood of multiple donors at New York Blood Center. In a typical procedure, the cells were initially stimulated by Sendai Virus ($10^4$ U/ml) as part of a protocol to induce Interferon. Twelve hours later the culture medium, rich in alpha-Interferon, was removed by centrifugation (800× g). The cells were resuspended to $4\times10^6$/ml in serum-free RPMI 1640 (obtained from Gibco, Grand Island) supplemented with 0.25% bovine serum albumin (obtained from Sigma, St. Louis, Missouri) and 1% phytohemagglutinin-M (obtained from Gibco) and incubated at 37° C. for 48 hours. In some preparations irradiated (5000 rad) Daudi cells ($10^6$/ml) were added to the medium in order to increase IL 2 production. At the end of the incubation, cells and cell debris were separated from the conditioned medium by centrifugation (10,000× g, 15 min) and the supernatant was used for purification of IL 2.

Ammonium Sulfate Precipitation (Fraction II)

1683 gm (NH$_4$)$_2$SO$_4$ were added to 3 liters of lymphocyte-conditioned medium to achieve 80% saturation. After gentle stirring overnight at 4° C., the precipitate was spun down (10,000× g, 15 min), dissolved in 0.05M Tris-HCl (pH 7.8) in a final volume of 300 ml, and subsequently dialyzed against 50 volumes of 0.05M Tris-HCl buffer (pH 7.8) for 48 hours with five changes of the dialyzing buffer.

Anion Exchange Chromatography (Fraction III)

For analytical purposes, 10 ml of the dialyzed concentrate was loaded on a 40 ml column of microgranular diethylaminoethyl cellulose (DE 52, obtained from Whatman, England) which had been previously equilibrated with 0.05M Tris-HCl (pH 7.8). The column was washed with 80 ml of the same buffer and proteins, including IL 2, were eluted using a linear gradient of Tris-buffered NaCl (0–0.3M NaCl) and 5 ml fractions were collected. IL 2-containing fractions were pooled and dialyzed against phosphate-buffered saline (pH 7.2) containing polyethyleneglycol (MW 6000) (50%, w/v) in order to concentrate pooled fractions. For large scale purification, 300 ml of diethylaminoethyl-cellulose slurry, equilibrated with 0.5M Tris-HCl (pH 7.8) was gently mixed with 300 ml of redissolved and dialyzed ammonium sulfate precipitate. After 30 minutes the diethylaminoethyl cellulose was spun down and the supernatant saved (Supernatant 1). The pellet was resuspended in 300 ml of 0.05M Tris-HCl (pH 7.8) containing 0.1M NaCl. After 10 minutes the diethylaminoethyl cellulose was spun down again (1,000× g) and the resulting supernatant pooled with Supernatant 1. The pooled supernatants were concentrated by dialysis against polyethyleneglycol (MW 6000)/phosphate-buffered saline (pH 7.2) as described above.

Gel Filtration (Fraction IV)

The concentrated diethylaminoethyl cellulose preparation was applied in 10 ml aliquots to an AcA 44 Ultrogel (obtained from LKB, Rockland, Maryland) column (2.5×90 cm), which had been previously equilibrated with phosphate-buffered saline (pH 7.2) containing 0.1% polyethyleneglycol (MW 6000). The flow rate was adjusted to 30 ml/hr and 6 ml fractions were collected. IL 2-containing fractions were pooled. The column was calibrated with bovine serum albumin (MW 68,000), chymotrypsinogen (MW 25,000), and ribonuclease A (MW 14,000), all obtained from Pharmacia (Piscataway, New Jersey). Subsequent to the preceding work, we have come to prefer the AcA 54 column over the AcA 44.

Chromatography on Blue Agarose (Fraction V)

Two hundred ml of the active fractions pooled from the AcA 44 Ultrogel column were applied to a Blue Agarose column (obtained from BRL, Gaithersburg, Maryland) with a bed volume of 40 ml that had been previously equilibrated with phosphate-buffered saline (pH 7.2). A linear gradient of NaCl (0–0.8M) in phosphate-buffered saline (pH 7.2) was applied and 20 ml fractions were collected. The IL 2-containing fractions were pooled and polyethyleneglycol (MW 6000) added to a final concentration of 0.1% (w/v) to stabilize the IL 2.

Chromatography on Procion$^R$-Red Agarose (Fraction VI)

The pool of active fractions eluted from Blue Agarose was dialyzed against phosphate-buffered saline (pH 7.2) and loaded on a 10 ml Procion$^R$-Red Agarose column (obtained from BRL), which had been previously equilibrated with phosphate-buffered saline (pH 7.2). The column was then washed with phosphate-buffered saline (pH 7.2) and bound proteins were eluted by using a stepwise gradient of NaCl in phosphate-buffered saline (pH 7.2) with a starting salt concentration of 0.3M NaCl and a final concentration of 1.0M NaCl.

High Performance Liquid Chromatography (for Trace Impurities)

BIF and IL-2 sometimes copurified with partially overlapping peaks through a number of steps: separation was achieved after the red agarose step above. Sometimes this separation showed partial overlap of the two activities. This appears to be dependent on the batch of Ly-CM used. A further step using reverse phase HPLC could also be used to effect complete separation or removal of trace impurities. The high salt eluates containing both IL-2 and BIF from red agarose were than fractionated by reverse phase HPLC on a Protesil 300 column (Whatman) using increasing concentrations of propanol in TEAP (1% phosphoric acid-triethylamine, pH 3.0) or acetic acid-pyridine buffer pH 4.0. For example:

Reverse Phase High Performance Liquid Chromatography (RP-HPLC)

RP-HPLC was performed with a Waters HPLC system (Walters, Associates, Milford, MA). The HPLC system included two M 6,000 solvent delivery pumps, a model 400 variable wavelength detector, a data module and a data processor. The separation was performed on a Protesil 300 column (Whatman). The buffers used were: Buffer A: 0.9M acetic acid/0.2M pyridine, pH 4.0; buffer B: buffer A in 50% 1-propanol (Burdick and Jackson, Lab., Muskegon, MI). Acetic acid and pyridine (HPLC grade) were purchased from Fisher, Scientific Co.). The IL 2 containing pool obtained from Procion$^R$-Red Agarose chromatography was acidified with acetic acid to pH 4.0 and injected onto the Protesil 300 column without regard to sample volume. The column was washed with buffer A (20 min) and bound proteins were eluted using a steep gradient 0–40% buffer B within the first 20 min and a 40–100% gradient of buffer B in 120 min. The flow rate was adjusted to 1 ml/min and 3 ml fraction were collected. One-half of each fraction was immediately stabilized by addition of 10 micrograms/ml bovine serum albumin and dialysis against PBS. Protein was estimated by Bio-Rad Protein Assay (microassay procedure using bovine albumin as a standard). IL 2 eluted at 45% propanol in TEAP.

High Performance Liquid Chromatography for Molecular Weight Determination

A micromeritics liquid chromatography Model 700 B (Micromeritics, Norcross, Georgia) with a fixed wavelength detector and injector system was used. The chromatography was performed either in the presence or absence of sodium dodecyl sulfate/dithiothreitol. Under non-denaturing conditions, 1 ml of Blue Agarose-purified IL 2 was injected into a Micropak TSK 3000 SW column (from Varian, Sunnyvale, California) and eluted with 0.035M sodium phosphate buffer (pH 6.8) at a flow rate of 0.8 ml/min. Fractions of 0.4 ml each were collected and 0.1% polyethyleneglycol (MW 6000) (w/v) was added to the fractions. The column was calibrated with bovine serum albumin (MW 68,000), chymotrypsinogen (MW 25,000), and ribonuclease A (MW 14,000), all obtained from Pharmacia. For analysis under denaturing conditions, 1 ml of Blue Agarose-Purified IL 2 was treated with 1% sodium dodecyl sulfate and 10 mM dithiothreitol at 37° C. for 1 hour and loaded onto the same column (previously equilibrated with 0.035M sodium phosphate buffer (pH 6.8) containing 0.1% sodium dodecyl sulfate and 1 mM dithiothreitol). Marker proteins were pre-treated in the same way and then used for column calibration.

Isoelectrofocusing

Ten mls of the AcA Ultrogel preparation of IL 2 were supplemented with 20% glycerol (v/v) and 2% Ampholine (v/v) (pH 3.5–10) (from LKB). A 5–60% glycerol density gradient, containing 0.1% polyethyleneglycol (MW 6000) (w/v) and 2% Ampholine (pH 3.5–10) was layered into an isoelectrofocusing column (110 ml from LKB). The IL 2 sample was applied onto the isodense region of the gradient, followed by focusing for 24 hrs at 4° C. using a constant power supply (Model 2103 from LKB). The terminal voltage was 2000 V and the terminal current 5 mA. Five ml fractions were collected and the pH determined in every fraction. All fractions were dialyzed against phosphate-buffered saline (pH 7.2) containing 0.1% polyethyleneglycol (MW 6000) (w/v) to remove the bulk of Ampholine and glycerol. The IL 2-containing fractions were pooled.

Concanavalin A-Agarose Chromatography

One ml of Procion$^R$-Red Agarose-purified IL 2 (500 U/ml) was loaded on a 2 ml concanavalin A (Con A)—agarose column (from Pharmacia) equilibrated with 0.02M sodium phosphate buffer (pH 7.2) containing 1M NaCl and 1 mM each of MgCl$_2$, MnCl$_2$, and CaCl$_2$. The column was washed with the equilibration buffer and the proteins were eluted with the same buffer containing 0.1M alpha-methyl-alpha-D-mannoside (obtained from Sigma).

Wheat Germ Agglutinin Column Chromatography

The wheat germ agglutinin column (2 ml from Pharmacia) was equilibrated with phosphate-buffered saline (pH 7.2) and 1 ml of Procion$^R$-Red Agarose-purified IL 2 was loaded onto the column. After washing with phosphate-buffered saline (pH 7.2) the column was eluted with phosphate-buffered saline (pH 7.2) containing 0.1M N-acetyl-glucosamine (obtained from Sigma).

Treatment with Neuraminidase

Blue Agarose-purified IL 2 (1000 U/ml) was adjusted to pH 5.0 with acetic acid and added to agarose-bound neuraminidase (from Clostridium perfringens, Type VI-A, supplied by Sigma). The mixture was incubated for 90 min at 37° C. with gentle shaking. The neuraminidase-agarose was then removed by centrifugation and the pH of the IL 2-containing supernatant was adjusted to 7.8 with Tris base. A control sample was treated in the same way except that the neuraminidase-agarose was removed prior to the incubation.

Protein Assay

The protein content of samples was measured using the Lowry technique [Lowry, O.H., et al. (1951) J. Biol. Chem. 193:265]. For protein concentrations lower than 5 micrograms/ml, samples were subjected to sodium dodecyl sulfate-polyacrylamide gel electrophoresis; the protein bands were visualized by the silver staining technique [Merril, C. R., (1979) Supra]; and the protein concentration estimated by comparison with known amounts of protein standards (soybean trypsin inhibitor and alpha-lactalbumin). Serial dilutions (200 ng to 2 ng) of these marker proteins were used.

Sodium Dodecyl Sulfate-Polyacrylamide Gel Electrophoresis

The discontinuous Tris-glycine system of Laemmli [Laemmli, U.K., (1970) 227:680] was used for 1.5-mm thick slab gels using a 5–20% gradient or a 15% of acrylamide. The samples were analyzed under both reduced (2% sodium dodecyl sulfate, 5% mercaptoethanol) and non-reduced (2% sodium dodecyl sulfate) conditions. After electrophoresis, gels were stained with Coomassie Brilliant Blue or by a silver nitrate method [Merril, C.R., et al., (1979) Supra]. Apparent molecular weights were determined using protein standards phosphorylase b (MW 94,000), bovine serum albumin (MW 68,000), ovalbumin (MW 43,000), carbonic anhydrase (MW 30,000), soybean trypsin inhibitor (MW 20,000) and alpha-lactalbumin (MW 14,500). After electrophoresis, the gels were sliced into 1-mm sections and proteins from each slice were eluted in 0.3 ml phosphate-buffered saline (pH 7.2). After 12–18 hours, the eluted materials were assayed for IL 2 activity.

Assay for IL 2 Activity

For the IL 2 assay, 4000 murine IL 2-dependent cytotoxic T-cell line cells were grown in the presence of log 2 dilutions of putative IL 2-containing medium in 96-well microtiter plates (obtained from Costar, Cambridge, Massachusetts). The total volume in each well was 0.2 ml. Twenty-four hours later, 0.5 microcurie of 3H-thymidine (specific activity 20 Ci/mmole, supplied by New England Nuclear, Boston, Massachusetts) were added to each well. After 4 hours, the cells were harvested on glass fiber strips and 3H-thymidine incorporation measured in a liquid scintillation counter (from Packard, Downers Grove, Illinois).

The IL 2 concentration in the experimental sample was then calculated by probit analysis [Gillis, S., et al. (1978) J. Immunol. 120:2027], using a standard containing 2 U/ml of IL 2. One unit activity is equivalent to half-maximal stimulation of 6 day old PHA-stimulated lymphoblasts obtained from normal human donors.

High levels of IL 2 production were achieved by sequential stimulation of pooled peripheral blood lymphocytes from multiple donors. Peripheral blood lymphocytes were first stimulated by Sendai Virus for 12 hours. After a change of serum-free culture medium, these cells were restimulated by phytohemagglutinin for an additional 48 hours.

Sendai Virus or phytohemagglutinin alone stimulated the production of IL 2 at a 6–10 U/ml level, while sequential stimulation by Sendai Virus and phytohemagglutinin increased IL 2 production to 50–100 U/ml. An additional increase in IL 2 production, up to 200 U/ml, was achieved by costimulation with Daudi cells.

Lymphocyte-conditioned medium was precipitated with $(NH_4)_2SO_4$ at 80% saturation. This yielded an approximate 10-fold concentration of the proteins with high recovery of IL 2 activity. See Table I.

Factor Assays

BIF T cell-replacing factor activity was measured in a plaque-forming assay for immunoglobulin secretion (Ralph, P. J., et al. (1984) J. Immunol. 132:1858 or Saiki et al. (1981) J. Immunol. 127:1044). Interferon content was assesed on inhibition of the cytopathic effect or vesicular stomatis virus (Steward, W. E. II (1980) The Interferon Systems. Springer-Verlag, Vienna and New York). Colony stimulating factor activity was determined on the ability to support growth of marrow granulocyte-macrophage colony-forming cells (Broxmeyer, H. E., et al. (1982) Blood 60:595).

B cell growth factor was assayed by the ability to enhance proliferation of anti-IgM-stimulated, purified tonsillar B cells and Staphylococcus Aureus-induced proliferation of purified B cells (Welte, K., et al. submitted for publication)

Analysis of trace Polypeptides with a silver stain (Merrill, et al. (1979) Supra)

This stain is highly sensitive; combining two dimensional electrophoresis and a silver stain.

Two-dimensional electrophoresis: This electrophoresis was carried out according to O'Farrell [(1975) J. Biol. Chem. 250:4007], with 3/10 Biolyte (Bio-Rad) in the first dimension and a 10% acrylamide uniform gel in the second dimension. Isoelectric focusing was at 500 V for 20 hr; slab gels were run at 20 mA/gel.

Staining: To stain the gels with silver (2) they are fixed in 50% methanol/12% acetic acid for 30 min (gels can be stored overnight in this solution). The gels tend to shrink in the 50% methanol solution. To expand them prior to staining, they are placed in 10% ethanol/5% acetic acid for 2 hr, followed by three washes with 10% ethanol (5 min each). The gels are then soaked in 4% (wt/vol) paraformaldehyde/1.43% (wt/vol) sodium cacodylate (adjusted to pH 7.3 with HCl) for 30 min., followed by three 5-min washes with 10% ethanol. The gels are then agitated gently for 30 min in a cupric nitrate/silver nitrate solution (made by dissolving 3.5 g of silver nitrate in 100 ml of water followed by addition of 1.5 ml of 0.5% cupric nitrate solution and then the simultaneous addition of 4 ml of pyridine and 8 ml of ethanol). We have found it necessary to use reagent-grade absolute ethanol in this step.

Next the gels are placed in fresh diammine solution (made within 5 min of use) prepared by mixing together 30 ml of a 19.4% (wt/vol) silver nitrate solution and 22.2 ml of a solution of sodium and ammonium hydroxide [stock solution contains 100 ml of 0.36% NaOH, 45 ml of fresh concentrated $NH_4OH$ and 55 ml of 20% (vol/vol) ethanol]. Diammine solution remaining after the procedure must be discarded because an explosive complex may form upon storage! After the diammine rinse, the gels were washed for 1 min in a reducing solution containing 2.5 ml of 10% formaldehyde (10 ml of commercial formaldehyde solution in 100 ml of water), 6 ml of 1% citric acid, and 100 ml of ethanol in one liter of water. This wash was repeated, again for 1 min, followed by several rinses in a second reducer, containing 5 ml of 10% formaldehyde, 5 ml of 1% citric acid, and 100 ml of ethanol in one liter of water. The proteins may begin to appear as brown or black spots at any time in the reducing solutions. Staining can be stopped by washing the gel in successive changes of deionized water. Image formation in the diammine step may occur if reagent-grade absolute ethanol and fresh stock solutions are not used. Surface contamination can be minimized by washing the glass slab plates thoroughly, immediately after each electrophoresis run, and using well washed surgical gloves when handling the gels. The gels are fragile after staining and should be photographed for a permanent record.

Gels that are overdeveloped may be lightened with a photographic reducer such as the copper reducer of Smith [Walls, E. J., et al. (1976) in Photographic Facts and Formulas, revised and enlarged by Carrol, J. S. ed. (Prentice Hall, Englewood Cliff, N.J. pp. 170–180]. A fresh mixture of equal volumes of two stock solutions ("A" and "B") are required. Solution A contains 37 g of cupric sulfate and 37 g of NaCl dissolved in liter of water with the addition of sufficient concentrated ammonium hydroxide to dissolve any precipitate. A deep blue solution should be formed. Solution B contains 458 g of sodium thiosulfate in 1 liter of water. Usually a 3:1 dilution of water to fresh reducer is used to lighten gels. The reduction is stopped by washing the gel in water.

Stained gels may be kept in water. Gels that are to be dried for storage or autoradiography should be first soaked in 30% (wt/vol) sodium thiosulfate for 15 min followed by four 15-min water rinses. The gels should then be soaked for 5 min in a preserving solution [methanol/$H_2O$/glycerol, 70:27:3 (vol/vol) [Mayer J. W., (1976) Anal. Biochem. 76:369], followed by drying on 3 MM filter paper (Whatman) at 50° C. under reduced pressure for 2 hr.

Autoradiography: Gels that were to be autoradiographed were dried as described above and then placed in x-ray film cassette holders (Kodak X-omatic, with regular intensifying screens). Exposure was at −70° C. with Kodak XR-2 x-ray film for appropriate timed intervals. Films were developed at 25° C. for 5 min in developer (Kodak KLX developer) followed by a 5-min fix (Kodak X-omatic fixer).

Radioiodination of Proteins with Enzymobeads

Bio-Rad technical bulletin, Supra method as follows (as used in Branca, Supra):

1. Rehydrate the Enzymobead reagent with 0.5 ml distilled water at least 1 hour before use. Store at 4° C. (Rehydrate the Singel Reaction Enzymobeads with 50 microliter water).

2. Make up 1% Beta-D-Glucose in aqueous solution. (2% Alpha-D-glucose can be used; however, it must be allowed to mutarotate overnight to the Beta configuration).

3. Into a disposable test tube or the single reaction vial add:

| | |
|---|---|
| 0.2 M phosphate buffer pH 7.2 | 5 microliter |
| Protein sample (IL2) | 10–25 microliter (10–100 microgram in a minimum volume of an azide-free buffer*) |
| Enzymobead Reagent | 50 microliter |
| 1.0 mCiNa$^{125}$I | 5–25 microliter |
| 1% Beta-D-Glucose | 25 microliter |
| All in 175 microliters. | |

*Since multiple isotopic substitution of a single molecule is undesirable, one generally labels a greater mass of a high molecular weight material (i.e. 150,000 Daltons) than a low molecular weight material (i.e. 18,000 Daltons).

4. Mix the reagents and allow iodination to proceed at room temperature for 15–25 minutes. The reaction can be quenched by either of two methods. The first requires centrifugation to remove the Enzymobead Reagent from the reaction mixture, followed by immediate removal of the supernatant for subsequent gel filtration. The second method used for IL 2 utilizes direct application of the test tube mixture to a gel filtration column.

In both cases, a Bio-Gel P-6 DG column is recommended for the separation of the unbound iodide from the labeled protein.

Dialyzed $(NH_4)_2SO_4$ precipitate was placed on a diethylaminoethyl cellulose column (DE 52). IL 2 was eluted with a salt gradient from 0–0.3M NaCl in 0.05M Tris-HCl (pH 7.8) buffer. The IL 2 produced in the absence of Daudi cells eluted as broad peak at low salt concentration (0–0.03M NaCl), while the IL 2 produced by costimulation with Daudi cells eluted at salt concentrations between 0.03 and 0.08M NaCl. See FIG. 1. Under both conditions, the bulk of proteins were eluted at higher salt concentrations (0.01–0.3M NaCl). This permitted a separation of IL 2 from the bulk of proteins in large scale batch preparations by using the 0.1M NaCl wash of the diethylaminoethyl cellulose for elution of IL 2.

Anionic exchange chromatography on diethylaminoethyl cellulose achieved about 50-fold purification and approximately 75% of the loaded IL 2 activity may be recovered in this procedure. See Table I.

The material eluted from diethylaminoethyl cellulose may then be concentrated approximately 20-fold by dialysis against 50% polyethyleneglycol (MW 6000) (w/v) and loaded onto an AcA 44 Ultrogel column. The IL 2 produced in the absence of Daudi cells was eluted in fractions 42–52 as a single peak corresponding to a molecular weight of 26,000±4000 daltons. When IL 2 was produced by costimulation with Daudi cells, a major peak of activity was eluted on fractions 52–66, corresponding to a molecular weight of 13,000–18,000 daltons, while a minor peak of activity was found at 26,000 daltons. See FIG. 2. The IL 2 activity-containing fractions were pooled.

This purification step achieved about a 2.7-fold increase in the specific activity and approximately 80% recovery of the loaded IL 2 activity. See Table I. This step also effectively removed proteins having molecular weights greater than 30,000 daltons. See FIG. 5.

IL 2 bound strongly to Blue Agarose, while most proteins did not bind to the column, as shown in FIG. 3. IL 2 was eluted from this column with 0.5–0.6M NaCl and could be clearly separated from alpha-Interferon, which eluted at 0.05–0.4M NaCl in phosphate buffer. See FIG. 3. In this purification step the specific activity increased 25-fold, with 61% recovery of the loaded IL 2 activity. See Table I.

Procion$^R$-Red Agarose has different binding properties from that of Blue Agarose [Thompson, S. T., et al. (1976), Proc. Nat'l. Acad. Sci. U.S.A. 73:361; Watson, D. H., et al. (1978) Biochem. J. 173:591].

IL 2 was also bound strongly to this column and eluted as a broad peak between 0.6–0.9M NaCl in phosphate buffer with peak activity in the 0.7–0.8M NaCl eluate. See FIG. 4. This broad elution profile was suggestive of molecular heterogeneity of IL 2. A majority of the other proteins did not bind to Procion$^R$-Red Agarose, and the rest eluted at low salt concentrations, as shown in FIG. 4. The 0.7M–0.8M NaCl eluate pool was found, through silver staining of a 5–20% gradient gel (sodium dodecyl sulfate-polyacrylamide gel electrophoresis), to contain three molecular components with molecular weights of 14,500±2000, 16,000±1000 and 17,000±1000 daltons depending on the experimental condition used for the production of IL 2. See FIG. 7.

The protein content of the preparation was measured by comparing the density of protein bands, visualized by silver staining, with serial dilutions of protein standards of known concentrations. Taking into account the limitation of this measurement, a specific activity of approximately $10^6 \pm 10\%$ U/mg protein and a final purification of 37, 191-fold were calculated. The overall recovery of IL 2 was 19% after Procion$^R$-Red Agarose chromatography (Fraction VI, Table I).

The strong binding of IL 2 to Procion$^R$-Red Agarose also made this step very useful for concentrating IL 2 from diluted preparations using a two-step elution method with phosphate buffer containing 0.5M and 1.0M NaCl. Under this condition, IL 2 activity was fully recovered in the 1.0M NaCl eluate.

The IL 2 preparation from various steps of purification were subjected to sodium dodecyl sulfate-polyacrylamide gel electrophoresis analysis. Preparations obtained prior to the Blue Agarose chromatography (Fractions I–IV) were analyzed on a 5–20% gradient gel followed by Coomassie brilliant blue staining as shown in FIG. 5. Preparations obtained after Blue Agarose chromatography and Procion$^R$-Red Agarose chromatography were also analyzed on a 5–20% gradient gel followed by the highly sensitive silver staining method as shown in FIG. 6.

When IL 2 was produced in the absence of Daudi cells and denatured, the Procion$^R$-Red Agarose preparation showed only two active bands with MW of 16,000 and 17,000 daltons (FIG. 6(c)) under both reducing and non-reducing conditions. When Daudi cells were used as costimulator for IL 2 production, one active protein band with a MW of 14,500 daltons was observed (FIG. 6(d)). If suboptimal concentrations of Daudi cells (less than $5 \times 10^5$/ml) were used, three protein bands with MW 14,500, 16,000 and 17,000 daltons were found.

To obtain a better resolution, the purified IL 2 was also analyzed on a 15% acrylamide gel. After staining, a molecular weight pattern similar to that obtained in the gradient gel was found. A parallel gel was sliced into 1-mm sections and proteins from each slice were eluted in phosphate-buffered saline (pH 7.2). IL 2 activity was found to be localized in slice numbers corresponding to molecular weights of 14,500, 16,000 and 17,000 daltons (FIG. 7). Re-electrophoresis of the proteins present in all three slices with IL 2 activity showed one single band with molecular weight identical to that of the eluted band.

Blue Agarose-purified IL 2, produced in the absence of Daudi cells, was incubated with 1% sodium dodecyl sulfate and 20 mM dithiothreitol at 37° C. for 1 hour and applied to an high performance liquid chromatography gel filtration column. The column was eluted with buffer containing 0.1% sodium dodecyl sulfate and 1mM dithiothreitol. As shown in FIG. 8, sodium dodecyl sulfate denatured IL 2 was eluted in the 17,000 daltons molecular weight region. Native IL 2, eluted with sodium dodecyl sulfate-free buffer, exhibited an apparent molecular weight of 26,000 daltons.

The IL 2 preparation obtained from the AcA 44 Ultrogel column was subjected to isoelectrofocusing analysis using Ampholines with a broad pH range (pH 3.5–10). The IL 2 obtained without Daudi costimulation was focused with an approximate isoelectric point of 6.7. See FIG. 9. The same pI was found if peripheral blood lymphocytes were stimulated in the presence of Daudi cells. The relatively broad focusing range observed, pH 6.5–7.5, was probably due to the reported molecular heterogeneity of IL 2 [Robb, R. J., et al., (1981) Supra]. The yield of IL 2 from the isoelectrofocusing column was approximately 30%. This method was, therefore, useful only for the biochemical characterization of IL 2, and not advantageous for preparative purification.

We were unable to detect any binding of IL 2 to either agarose-bound concanavalin A or to a wheat germ agglutinin column. Neuraminidase treatment of IL 2 did not affect its biological activity or its molecular weight pattern.

The mitogenicity on normal peripheral blood lymphocytes, the capacity to support the growth of murine and human cytotoxic T-cell line and the presence of other cytokines were studies in the highly purified IL 2. In order to test for the presence of phytohemagglutinin, the mitogenicity of the IL 2 preparations was studies on normal peripheral blood lymphocytes. A low level of mitogenic activity, about 5% of that present in lymphocyte-conditioned medium, was detected only in undiluted IL 2 preparations obtained from the diethylaminoethyl cellulose purification step. Blue Agarose- and Procion$^R$-Red Agarose-purified IL 2 was completely free of mitogenic activity. IL 2 obtained from Blue Agarose and Procion$^R$-Red Agarose chromatography reportedly very actively supports the long term growth of human and murine cytotoxic T-cell lines. Human cytotoxic T-cell line appear to require approximately 10 U/ml purified IL 2 for their optimum growth, while murine cytotoxic T-cell lines. Human cytotoxic T-cell line appear to required approximately 10 U/ml purified IL 2 for their optimum growth, while murine cytotoxic T-cell line are maximally stimulated at 2 U/ml. Procion$^R$-Red Agarose preparations of IL 2 contained generally no detectable pyrogen activity, alpha- or gamma-Interferon, granulocyte-macrophage colony-stimulating activity, T-cell replacing factor, or thymocyte differentiating activity. (See above). Dr Geneviene Incefy of Sloan-Kettering performed these thymocyte differentiating factor assays.

Lymphocyte-conditioned medium harvested after sequential stimulation of peripheral blood lymphocytes with Sendai Virus and phytohemagglutinin, and costimulation with Daudi cells, showed an IL 2 concentration of 200—200 U/ml. It was possible, therefore, to obtain a high IL 2 concentration in the absence of other potentially toxic costimulators such as PMA [Robb, R. J. et al., (1981) J. Exp. Med. 154:1455; Mizel, S. G., et al., (1981) J. Immunol. 126:834], which could interfere with biological testing and clinical trials of purified IL 2.

The purification procedure disclosed introduces the chromatography on Blue Agarose, on Procion$^R$-Red Agarose and on HPLC as three new purification steps for IL 2. Although it has been suggested that these blue and red agarose dyes bind specifically to proteins containing the dinucleotide fold [Thompson, S. E., et al. (1976) Supra], we have found no evidence for any effect of NAD± or NADH on biological activity or biochemical behavior of IL 2. The binding of IL 2 to these dyes may be due to the electrostatic or hydrophobic interactions. The use of these two steps permitted a 37,000-fold purification of IL 2 from medium conditioned in the presence of 0.25% bovine serum albumin, with a 19% overall recovery of IL 2 activity. All other purification methods, for both murine and human IL 2, have achieved neither a specific activity nor a yield comparable to those described here. (See discussion of work of Mier et al, Gillis et al. and Granelli-Piperno et al. Supra above). Also see German patent application No. 314 9360 by Sonnenborn, Hans H., et al. where IL-2 prepared for production of mAb appears to be contaminated with gamma-interferon, albumin and pyrogen. Limited use of hydrophobic chromatography (blue only) leads to an impure IL 2 certainly not pure enough for clinical use. In the work there is no analytical purity check and the goal of the work seems to be to produce antibody to an impure IL 2, separated from PHA.

Our purification procedure also avoided time consuming steps. This has made our procedure very useful for large scale purification of IL 2.

Lymphokines and other regulator molecules such as IL 1, [Mizel, S. G., et al. (1981) Supra], alpha- or gamma-Interferon, T-cell replacing factor, and CSF [Burgess, A.W., et al. (1980) Blood 56:947], have different capabilities of forming hydrophobic interactions. These properties were utilized to separate IL 2 from other lymphokines and factors which contaminate most partially purified IL 2 preparations. For example, alpha-Interferon co-purified with IL 2 during ion exchange chromatography and gel filtration steps, but was clearly separated from IL 2 by Blue Agarose chromatography. See FIG. 3. After chromatography on Procion$^R$-Red Agarose, the IL 2 preparation did not contain any detectable Interferon (alpha and gamma), granulocyte-macrophage colony-stimulating factor, T-cell replacing factor, or thymocyte differentiating activities. In addition, the Procion$^R$-Red Agarose-purified IL 2 appeared to be free of any contaminating proteins (FIG. 6).

TABLE II

| Independence of BIF Action From IL-2 | | | |
|---|---|---|---|
| | | Induced ISC | |
| | 0 | BIF | BIF (1:8) |
| No addition | 0 | 868 ± 42 | 207 ± 22 |
| + IL-2 | 0 | 830 ± 16 | 219 ± 13 |

Native IL 2 has been previously shown to exist in several molecular forms [Mier, J. W., et al., (1980) Proc. Nat'l. Acad. Sci. U.S.A. 77:6134; Gillis, S., et al., (1980) J. Immunol. 124:1954; Robb, R. J., et al., (1981) Mol. Immunol. 18:1087]. Here we show that the methods used for IL 2 induction by peripheral blood lymphocytes can be responsible for the heterogeneity. Native IL 2 produced in the presence or absence of Daudi cells exhibited molecular weights of about 14,500 and 26,000 daltons, respectively (FIGS. 2 and 8). Both molecular forms could be obtained by varying the concentration of costimulator cells. These results demonstrated that molecular weight differences [reported by Mier, J. W., et al. (1980) Supra and Gillis et al. (1980) J. Immunol. 124:1954] were most likely due to different methods of IL 2 induction.

Taniguchi et al. (1983) [Nature 302:305 (1983)] report a cDNA coding for a protein product with some characteristics of human IL 2. The human mRNA used originated from a human leukemic cell-line stimulated by concanavalin A. The DNA clone contains bacterial DNA as well to form the cDNA and the cDNA is expressed in an SV40 transformed monkey kidney cell line COS-7. It is questionable whether this represents a properly glycosylated human IL 2. The deduced amino acid sequence has no N-glycosylation site. Low IL 2 activity is found (70 units per ml COS cell medium). Extra amino acids also appear to be present in the structure. No human studies were done with this material, nor large scale production.

After denaturation by sodium dodecyl sulfate, the 26,000-dalton IL 2 of the invention exhibited a molecular weight of 16,000–18,000 daltons by high performance liquid chromatography gel filtration. Sodium dodecyl sulfate-polyacrylamide gel electrophoresis of this denatured form demonstrated the presence of two biologically active bands with molecular weights of about 16,000 and 17,000 daltons, respectively. These results, together with those of Caplan et al. [(1981)] J. Immunol. 126:1264], indicate that, after sodium dodecyl sulfate denaturation, human and murine IL 2 exhibit similar molecular weights. The molecular weight of human IL 2 produced in the presence of Daudi cells was not affected by sodium dodecyl sulfate denaturation. Since native rat IL 2 has been reported to show a molecular weight of 15,000 daltons [Gillis, S., et al. (1980) J. Immunol. 124:1954; Smith K. A., (1980) Immunological Rev. 51:337; Smith, K. A., et al. (1980) Molecular Immunol. 17:57], it appears that IL 2 activity is present in a polypeptide of about 14,500–17,000 daltons in all species studied. It is not known if these different molecular forms have different functions, such as preferential stimulation of T cell subsets. It is also not known whether the same T-cell will switch its IL 2 synthesis from 26,000 daltons to 14,500 daltons upon costimulation by Daudi cells, or whether different T-cell subsets are indeed responsible for the release of IL 2 in two molecular forms.

Assuming two functional T-cell subsets, one subset would produce the 26,000 MW IL 2 in response to phytohemagglutinin alone, while the second subset would require phytohemagglutinin as primary stimulus and costimulation by Daudi cells as a second signal for the production of 14,500 MW IL 2. Daudi cells express HLA-DR antigens and Fc receptors. Both of these surface molecules have been implicated in the augmentation of the IL 2 response [Palacios, R., et al., (1981) Cellular Immunol. 63:143; Shimizu, S., et al., (1982) J. Immunol. 128:296]. The effect of Daudi cells on the IL 2 response, however, does appear to be more complicated than previously suggested [Palacios, R., et al., (1981) Supra; Shimizu, S., et al., (1982) Supra], in view of: (a) the shift in molecular weight of IL 2 from 26,000 to 14,500 daltons induced by Daudi cells; (b) the augmentation of IL 1-independent IL 2 production as seen in the human lymphoblastic cell line Jurkat [Venuta, S., et al. (1983) Blood 61:781]; while Friedman et al. [(1982) J. Immunol. 128:935] recently reported that cells obtained from a patient with T-cell chronic lymphocytic leukemia, stimulated under identical conditions, released the 14,500 MW form of IL 2.

The reason for the molecular heterogeneity of the sodium dodecyl sulfate-denatured and native IL 2 remains to be explored. A variable degree of glycosylation may provide an explanation of this phenomenon [Robb, R. J., et al., (1981) Mol. Immunol. 18:1087; Clark-Lewis, I., et al., (1982) J. Immunol. 128:180]. Robb et al. (1981) Supra have shown that neuraminidase, glycosydases and inhibitors of glycosilation can reduce the heterogeneity of IL 2 produced by tonsil lymphocytes. However, we were not able to affect the molecular weight of IL 2 by neuraminidase treatment, nor were we able to detect any binding of IL 2 to immobilized lectins (concanavalin A and wheat germ agglutinin). The lack of binding of IL 2 to lectins has been previously reported by Mier et al. [Mier, J. W., et al., (1980) Supra]. The difference between these results are probably due to the different methods of induction and purification of IL 2, which appear to affect the biochemical characteristics of IL 2.

The purification steps described herein produced hp Il 2 with a specific activity of about $10^6$ U/mg protein. Since the lowest molecular weight of an active IL 2 polypeptide was 14,500 daltons, it could be calculated that 1 U/ml of IL 2 was equivalent to a molar concentration of $7 \times 10^{-11}$M. An IL 2 concentration of $1.4 \times 10^{-11}$M or approximately $4 \times 10^5$ molecules/cell was required for half maximum stimulation of murine cytotoxic lymphocytes. Similar values have been reported by Mizel et al. for IL 1 [Mizel, S. G., et (1981) Supra].

The highly purified (hp IL 2) IL 2 may be used to investigate the biological effects of IL 2, both in vitro and in vivo. In preliminary experiments, we have been able to partially restore, in vitro, the response of T cells of a patient with Nezeloff's syndrome in both the allogeneic mixed lymphocyte reaction (MLR) and in cell-mediated lympholysis (CML) by addition of human Procion$^R$-Red Agarose-purified IL 2 (Fraction VI). These studies should contribute to the understanding of normal human lymphocyte function, immunoficiency syndromes, and the pathophysiology of human lymphoblastic leukemias (Gillis, S., et al., (1980) AACR Abstract No. 955, p. 238; Venuta, S., et al., (1983) Supra.

hp IL 2 is useful in a variety of in vitro systems, including the continuous growth of antigen specific cytotoxic T-cells and the establishment of IL 2 dependent long-term cell lines from patients with certain T-cell neoplasias. It is also feasible to grow autologous tumor-specific human T-cells in large quantities in vitro and then transfuse these cells in vivo with a therapeutic result. Further uses to be considered are the establishment of long-term cultures of normal T-cells for drug testing and carcinogenicity tests.

Animal models that have been used to explore therapeutic uses of crude conditioned media containing IL 2 are the nude mouse (T-cell immunodeficiency) and the mouse immunosuppressed by Cytoxan ®. Preliminary results suggest that the immune response can be normalized by these media [Lipsick et al., (1981) Proc. Nat'l. Acad. Sci. 78:2398; Merluzzi et al., (1981) Cancer Res. 41:850]. Preliminary studies using our own material suggest that the active ingredient in fact is IL 2.

Further studies in both mice [Miller et al., (1981) Eur. J. Immunol. 11:751] and men [Gillis et al., (1981) J. Clin. Invest. 67:937] have shown that aging and its associated immune defects might be related to a defect in IL 2 production.

Frabricus et al. U.S. Pat. No. 4,390,623 issued June 28, 1983 use mitogen-free and serum free crude IL 2-containing material which is not further purified and study its effect on cells in culture. No patients are treated. The material is not pyrogen-free and Fabricus et al. propose to treat humans with IL 2 derived from cattle and/or pigs as well.

More recently, Lopez-Botet et al., [(1982) J. Immunol. 128:679], evaluated patients with severe combined immunodeficiency, Wiskott-Aldrich Syndrome, immunodeficiencies with hyper IgM, x-linked agammaglobulinemia, and common variable immunodeficiency for proliferative response to phytohemagglutinin with and without addition of mitogen-free supernatants containing IL 2. The hyporesponse to phytohemagglutinin in this group of patients was associated with a defect in the production of IL 2.

We have found that the defect of the proliferative response of T-cells in patients with Nezeloff Syndrome, in immunodeficiency associated with (a) advanced age, (b) burn patients, (c) newborns, (d) Kaposi's Syndrome in Homosexuals, (e) Hodgkin's disease, and (f) chemotherapy can almost be completely normalized in vitro by additions of homogeneous hp IL 2.

Based on these encouraging results we show results herein of a combined phase I and phase II trial of IL 2 in patients with congenital and acquired immunodeficiency syndrome. So far no untoward reactions have been seen in fifteen patients. (maximum dose levels reached 20,000 U/m$^2$/day).

We anticipate extensive clinical trials and therapeutic potential for patients with congenital immunodeficiency syndromes, Hodgkin's disease (T-cell defect frequent), Kaposi's Syndrome, immunosuppression associated with cancer, and immunosuppression associated with chemotherapy and/or radiation therapy; and for aged individuals as well as patients with other immunodeficient states like patients after bone transplantation therapy.

We believe that hp IL 2 alone or in combination with other lymphokines might become the treatment of choice for several of the above listed syndromes, in a similar fashion as parenteral insulin has become the specific therapy for diabetes mellitus.

Further use is anticipated in IL 2-dependent neoplasia such as ALL and neoplasias of mature T-cells. Modification of the hp IL 2 molecule either chemically or through addition of cytotoxic substances to the IL 2 molecule may allow selective elimination of IL 2-dependent neoplastic cells through blockage of receptor sites or cell type specific delivery of toxic substances to IL 2 responder cells. This approach might also be helpful in selectively eliminating IL 2 responder cells in cases with over-reactive immunity, such as in autoimmune disorders.

The examples serve only to illustrate the therapeutic utility of this highly purified IL 2 without limiting it to the specific examples shown. These examples are based on work which resulted in several papers which are hereby incorporated by reference: Flomenburg, N., et al. (1983) J. Immunol. 130:2644; Mertelsmann, Roland et al. in Normal and Neoplastic Hematopoiesis pp. 545–555 (1983), Alan R. Liss Incorp., Ciobanu, Niculae et al. (1983) J. Clin. Immunol. 3;332 and Merluzzi, Vincent J. (1983) J. Immunol. 131:806. Welte, K., et al. (1984) Blood in press.

The highly purified IL 2 (hp IL 2) of the invention has recently been approved by the Food and Drug Administration (FDA) for use as a drug; this IL 2 has IND number BB IND 1916.

Immunological Effects of IL 2 in Primary Immunodeficiency Diseases

Five children with primary deficiencies of T cell function were studied to assess the effects of highly purified exogenous Interleukin 2 (hp IL 2) on their in vitro T cell responses. The lymphocytes from one child with Nezeolof's T cell deficiency demonstrated absence of endogeneous IL 2 production and improved proliferative responses to mitogen or alloantigen in the presence of exogenous hp IL 2. Moreover, during in vitro mixed lymphocyte culture in the presence of exogenous hp IL 2, his lymphocytes were able to develop into cytotoxic effector cells. A second child with Nezelof's syndrome demonstrated a different type of defect. The lymphocytes from this child had less impairment of endogenous IL 2 production. Although hp IL 2 increased the proliferation of his cells in response to PHA, similar augmentation was not seen after stimulation with OKT3 or alloantigen. In cell-mediated cytotoxicity assays, after mixed lymphocyte culture, natural killer-like activity was strongly boosted in the cultures that contained IL 2, but T cell-mediated cytotoxicity was not. The lymphocytes from three patients with severe combined immunodeficiency did not show improved proliferative responses in the presence of hp IL 2. Thus, only one of the five patients demonstrated the combination of defective endogenous IL 2 production, but preservation of the ability to respond appropriately to exogenous hp IL 2. This child may therefore have suffered from a T cell defect pathophysiologically similar to that seen in nude or aged mice.

We have studied five children with defective T cell function caused by primary immunodeficiency diseases in order to ascertain whether some human immunodeficiency states might be caused by defects in the production of or response to IL 2. One child subsequently received an in vivo trial of hp IL 2. The results of these studies are presented and their implications discussed. Highly purified human IL 2 above was used for all in vitro work IL 2 assay was done as above.

Cell collection: All in vitro assays employed PBL collected from density gradient centrifugation of a 1:1 mixture of peripheral blood and RPMI 1640 on Ficoll-Hypaque (Lymphoprep, Accurate Chemical and Scientific Corp, Hicksville, NY). Cells suspended over the Ficoll-Hypaque layer were harvested, washed three times in RPMI 1640, and then used for appropriate studies [Boyum, A. (1968) J. Clin. Lab. Invest. 91:21S]. E-rosette assays and immunofluorescent characterization were performed according to standard techniques [Kaplan, M. E., et al. (1974), J. Immunol. Methods 5:131; Herzenberg, L. A., et al. (1978) in Handbook of Experimental Immunology ed. by D. M. Weiss Blackwell Scientific Publications, Oxford, p. 22.1.].

T cell response to mitogens and microassay for IL-2 production: PBL were diluted to a concentration of $2 \times 10^6$ cells/ml in RPMI 1640+5% fetal calf serum (FCS). One hundred microliters of cells were mixed with equal volumes of RPMI-5% FCS containing appropriate concentrations of mitogens and/or IL 2. The final concentrations used for the mitogens were 0.5% for phytohemagglutinin and 1 ng/ml for the monoclonal antibody OKT3 [Chang, T. W., et al., (1981) Proc. Nat'l. Acad. Sci. U.S.A. 78:1805) (Ortho Pharmaceuticals, Raritan, NJ]. IL 2 was used at 10 U/ml.

For each time point to be studied, duplicate plates were prepared. 0.5 micro Ci of [$^3$H]TdR (specific activity 20 Ci/mM, New England Nuclear) was added to each well of the first plate. After an additional 4-hr incubation, cells were harvested on glass fiber strips and counted in a liquid scintillation counter. The second plate was spun to ensure pelleting of the PBL. The supernatants were removed and assayed for IL 2 activity as described above. As previously described [Welte, K., et al. (1982), J. Exp. Med. 156;454]. IL 2 production was maximal 24 hr after initiation of culture. Normal controls consisted of healthy volunteers ranging from 4 wk to 40 yr in age.

Mixed lymphocyte culture (MLC): In vitro MLC was performed with the use of PBL. Fifty thousand responder cells were mixed with 50,000 stimulator cells, which had been treated with 4000 rads (444 rad/min for 9 min in a Cesium Gammacell 1000 irradiator (Atomic Energy of Canada Ltd., Ottawa)). The cultures were performed in RPMI 1640 and 15% pooled human serum (HS) supplemented with penicillin 100 U/ml, streptomycin 100 micrograms/ml and glutamine 2 mM. A total volume of 150 microliter per well was cultured in round bottom microtiter plates (NUNC, Vanguard International, Neptune, NJ) at 37° C. in a humidified 5% $CO_2$ atmosphere. After 120 hr, plates were labeled with [$^3$H]TdR 1 microCi/well (6.7 Ci/mmol, New England Nuclear). Eighteen hours later, they were harvested with the use of a Skatron multi-sample harvester (Flow Laboratories, Hamden, CT). After drying the filter papers, each sample was placed in a scintillation vial with 2 ml of scintillation fluid, cooled, dark adapted, and counted in a liquid scintillation counter. To assess the effect of hp IL 2 on MLC, parallel cultured were tested with and without hp IL 2. hp IL 2 was added to produce a final concentration of 20 U/ml [Dupont, B., et al. (1976), Adv. Immunol. 23:107].

Cell-mediated lympholysis (CML) and natural killer cell (NK) assays: Effector cells for CML were developed by incubating equal numbers of responder PBL and 4000 rads irradiated stimulator PBL at a final concentrations of $1 \times 10^6$ cells/ml in RPMI-10% HS in 25 $cm^2$ tissue culture flasks (Corning, Medfield, MA) as previously described [Schendel, D. J., et al. (1979) Tissue Antigens 13:112]. After 6 days, the cells were harvested and resuspended in fresh media (RPMI 1640-10% HS) at appropriate cocentrations dependent on the effector to target cell ratios (E:T) to be used. Duplicate cultures with and without hp IL 2 were prepared. hp IL 2 was added to produce a final concentration of 20 U/ml.

Target cells for CML consisted of PHA-stimulated lymphoblasts that had been cultured for 3 days in medium containing PHA at a 1:100 dilution of the stock solution. Targets were incubated for 1 hr with 250 micro Ci of $^{51}$Cr($Na_2{}^{51}CrO_4$) specific activity 200 to 500 mCi/mg Cr, New England Nuclear), washed twice, and resuspended at a concentration of 30,000 cells/ml. One hundred microliters of effectors and targets were mixed in round bottom microliter wells (Linbro, Flow Laboratories). Triplicate determinations were performed. Microtiter plates were spun momentarily to ensure adequate mixing and incubated for 4 hr.

Supernatants were harvested with a Titertek Harvesting System (Flow Laboratories) and counted in a gamma counter for 1 min. Percent cytotoxicity is determined by the formula:

$$\% \text{ Cytotoxicity} = \frac{\text{Experimental }^{51}\text{Cr release (cpm)} - \text{Spontaneous }^{51}\text{Cr release (cpm)}}{\text{Maximum }^{51}\text{Cr release (cpm)} - \text{Spontaneous }^{51}\text{Cr release (cpm)}} \times 100$$

Spontaneous release is defined as the number of counts produced by incubation of 3000 target cells in media without effectors. Maximum release is the number of counts produced when 3000 target cells are lysed using 10% Triton X detergent (New England Nuclear).

The NK cell activity studied in the patients included both spontaneous NK activity of freshly isolated PBL as well as the NK activity which is developed during 6 day in vitro MLC. It is defined as NK activity through the use of the normal NK target cell line. K562. The assays were performed in identical fashion as for the CML assay except that the K562 cell lines was used as the target [West, W. H., et al. (1977) J. Immunol. 118:355].

Case Summary—J.V.

J.V. was a 3½-yr-old patient with Nezelof's syndrome. He came to medical attention at the age of 2 because of a series of infections secondary to Gram-positive and Gram-negative bacteria, amebae, and fungi. Evaluation revealed low normal levels of immunoglobulin(IgG 810 mg/100 ml, IgA 210 mg/100 ml, IgM 85 mg/100 ml). Complement levels were normal. T cells were markedly reduced in number (absolute T cell count=400/microliter); Sixteen percent of his PBL were Leu 2a+, 9% were 3a+, and 16% were SIg+. Lymph node biopsy revealed depleted parafollicular zones. Proliferative responses to the T cell mitogens PHA and Con A were markedly reduced (PHA-1244 cpm $^{14}$C TdR vs 29,290 cpm for a normal control, Con A-386 cpm vs 13,350 cpm). Based on these findings, the diagnosis of Nezelof's syndrome was made.

At the age of 3½, he developed *Mycobacterium avium* penumonitis and Candida esophagitis. He was referred to our institution for a T cell-depleted marrow graft from his HLA haploidentical half-brother with the use of the lectin separation technique of Reisner et al. [(1980) Lancet 2:1320]. The initial in vitro studies described here were performed before grafting. No durable evidence of engraftment was documented. The patient's condition deteriorated with cardiomyopathy secondary to adenovirus infection, renal failure, seizures, and aspergillus pneumonia. Because of the desperate clinical situation and evidence of improved T cell function in vitro in the presence of IL 2, highly purified IL 2 was administered subcutaneously daily in the left thigh as part of an approved phase I investigation. Informed consent was obtained.

The patient received five escalating doses of 0.1, 1.0, 10, 100, and 500 units. His clinical condition deteriorated with several episodes of severe bronchospasm. Mechanical ventilation was required and the patient expired because of respiratory failure and hypotension 8 days after initiation of hp IL 2 therapy. Postmortem examination revealed extensive pulmonary aspergillosis. It has been suggested retrospectively that this child may have suffered from the acquired immunodeficiency syndrome that has affected homosexual men, drug abusers, Haitians, and hemophiliacs [CDC Task Force (1982) N. Engl. J. Med. 306:248]. This issue was raised based on the fact that the child's mother was an i.v. drug abuser and that his infectious problems were not documented during his first 2 yr of life.

Characterization of the immunologic defect of patient J.V.: The ability of PBL from patient J.V. to produce IL 2 was assessed by using stimulation with PHA and the mitogenic monoclonal antibody OKT3 [Chang, T. W., et al. (1981), Proc. Nat'l. Acad. Sci. U.S.A. 78:1805]. As demonstrated in Table III, after 24 hr of culture, neither stimulus was capable of inducing IL 2 production from the PBL of this child. In contrast, each of these mitogens regularly elicits IL 2 production from normal PBL. The production of IL 2 was monitored for 72-hr. After mitogen stimulation at no time during the 72 hour period was IL 2 production observed.

The effects of highly purified, exogenous IL 2 on in vitro assays of T cell function were subsequently studied in this child. The proliferation of patient J.V.'s.

TABLE III

| | IL 2 production 24 hr after mitogenic stimulation | | |
|---|---|---|---|
| | IL 2 Produced (U/ml) | | |
| | Production by Nezelof's patients | | Median production and range in normal individuals |
| Stimulus | J.V. | A.F. | (N = 22)* |
| | U/ml | | |
| OKT3 | 0.0 | 0.6 | 3.0 (0.9–16) |
| PHA | 0.0 | 0.6 | 2.1 (0.8–6.8) |

*N = the number of normal individuals studied

PBL in response to OKT3 and PHA in the presence and absence of exogenous IL 2. The inability of this patient's cells to sustain proliferation beyond 48 hr is corrected when exogenous IL 2 is added, with an approximately 10-fold increase in proliferation. In a normal individual, addition of hp IL 2 does increase proliferation somewhat, but in contrast to the patient, there is less than a twofold increase. Highly purified IL 2 in the absence of a mitogenic stimulus does not induce significant proliferation of normal PBL during the first 72 hr of culture. (After 5 to 6 days of in vitro culture, some augmentation of thymidine uptake is seen).

The effects of exogenous hp IL 2 on in vitro MLC are summarized in Table IV. In Table IVA, the responses of patient J. V. are shown. The patient's PBL were sensitized with pooled PBL from 10 normal individuals in order to provide maximal allogeneic stimulation. In the absence of hp IL 2, J.V. demonstrates minimal to absent proliferation. When hp IL 2 is added, the response is boosted 4.5- to 13-fold. As shown in MLC experiment 2, the irradiated stimulator pool does not contribute to the observed proliferation. Normal individuals after 6 days are shown in Table IVB. In contrast to the patient, normal individuals do not show significant augmentation of alloantigen-induced proliferation in the presence of exogenous hp IL 2. This is evident with the use of stimulation with either PBL from a single unrelated person or with a pool of PBL from 10 individuals. In contrast, the response to autologous stimulation is boosted when exogenous IL 2 is added. Exogenous hp IL 2 also does not appear to accelerate or otherwise alter the kinetics of the MLC response to alloantigen.

TABLE IV

| In vitro effects of highly purified human IL 2 on mixed lymphocyte culture response* |
|---|
| A. PBL - J.V. (Nezelof's Syndrome) |

TABLE IV-continued

In vitro effects of highly purified human IL 2 on mixed lymphocyte culture response*

| Respondor PBL | Stimulator PBL | | |
|---|---|---|---|
| | Pool$_x$ | JV-PBL$_x$ | Medium |
| MLC 1 | | | |
| J.V. (PBL) + IL2 | 6,048 | 676 | 440 |
| J.V. (PBL) | 466 | 152 | 148 |
| MLC2 | | | |
| J.V. (PBL) + IL2 | 6,442 | 1,400 | 1,178 |
| J.V. (PBL) | 1,464 | 812 | 984 |
| Pool$_x$ medium + IL2 | — | — | 246 |
| Pool$_x$ medium | — | — | 142 |

B. Normal PBL

| Responder PBL | Stimulator PBL | | | | |
|---|---|---|---|---|---|
| | NC1$_x$ | NC2$_x$ | Pool 1$_x$ | Pool 2$_x$ | Medium |
| NC1 | 476 | 11,139 | 19,402 | 19,202 | 448 |
| NC1 + IL 2 | 5,532 | 12,358 | 16,067 | 13,986 | 2,069 |
| NC2 | 10,255 | 363 | 14,936 | 18,241 | 332 |
| NC2 + IL 2 | 10,327 | 3,451 | 15,220 | 13,780 | 1,076 |

C. PBL - A.F. (Nezelof's Syndrome)

| Responder PBL | Stimulator PBL | | | |
|---|---|---|---|---|
| | Pool$_x$ | Unrelated$_x$ | PBL$_x$ | Medium |
| A.F. (PBL) + IL 2 | 9,154 | 9,406 | 8,314 | 8,674 |
| A.F. (PBL) | 1,692 | 642 | 736 | 632 |
| Medium + IL 2 | 150 | 158 | ND | ND |
| Medium | 144 | 164 | ND | ND |

D. PBL - A.W. (SCID)

| Responder PBL | Stimulator PBL | | | |
|---|---|---|---|---|
| | Pool$_x$ | Unrelated$_x$ | PBL$_x$ | Medium |
| A.W. (PBL) + IL 2 | 666 | 414 | 316 | 292 |
| A.W. (PBL) | 342 | 316 | 274 | 288 |
| Medium + IL 2 | 302 | 208 | ND | ND |
| Medium | 230 | 182 | ND | ND |

*MLC induced proliferation of PBL from patients J.V., A.F., and A.W. and two normal individuals in the presence and absence of highly purified IL 2. x denotes irradiated (4000 rads) stimulator cell. Pool denotes PBL from 10 normal donors. The data represents median triplicate values of cpm after 24-hr pulse labeling with [$^3$H]Tdr (120 to 144 hr).

The effect of exogenous hp IL 2 on the generation of cytotoxic effector cells by patient J.V. is shown in Table VA. Freshly harvested PBL from J.V. without in vitro stimulation exhibited low but normal levels of NK activity vs the NK-sensitive target K562, but no cytotoxic T cell activity vs PHA lymphoblasts. After 6-day in vitro sensitization vs an allogeneic pool of PBL in the absence of IL 2, no viable cells were recovered. A similar sensitization in the presence of hp IL 2 resulted both in the generation of cytotoxic T cell activity against PHA lymphoblasts and augmented NK-like cytotoxicity against K562. In normal individuals, hp IL 2 produces minimal augmentation of cytotoxicity in mixed lymphocyte cultures, employing pooled alloantigenic stimulation (Table VB). However, with a submaximal stimulation using PBL from a single unrelated donor, T cell-mediate cytotoxicity against PHA lymphoblast targets is augmented in normal individuals as well.

Results of in vivo trial of highly purified IL 2 in patient J.V.: As detailed in the case history, patient J.V. received a brief in vivo trial of subcutaneous hp IL 2. Although the patient succumbed to severe pulmonary infection, the postmortem examinations of his lymphoid tissues suggests that hp IL 2 may have exerted an in vivo effect. In comparing photommicrographs of a lymph node draining the IL 2 injection sites and a comparable control node from a remote site, the control node, which is representative of the nodes throughout the rest of the body, reveals a striking absence of lymphocytes, with primarily histocytes and plasma cells being identified. The draining node, in marked contrast, shows nests of lymphoid cells, not present in the other lymphoid tissues. It is noteworthy that although the patient received a T cell-depleted bone marrow graft from an HLA haploidentical half brother, there was no evidence of residual engrafted cells at the time of the patient's death either via cytogenetic analysis or HLA typing of purified T cell populations.

TABLE V

In vitro effects of highly purified human IL 2 on cell-mediated cytotoxic responses developed in 6-day MLC[a]

A. J.V. - PBL (Nezelof's Syndrome)

| | | % Cytotoxicity ($^{51}$Cr Release) Target Cells | |
|---|---|---|---|
| Effector Cells | E:T Ratio | Pool PHA[b] | K562 |
| J.V. PBL (before MLC) | 50:1 | 2 | 28 |
| (J.V. PBL) (pool$_x$)[c] | 50:1 | No viable cells recovered | |
| (J.V. PBL) pool$_x$) + IL2 | 50:1 | 21 | 45 |

B1. Normal PBL after pooled allogeneic stimulation

| | | % Cytotoxicity ($^{51}$Cr Release) Target Cells | | |
|---|---|---|---|---|
| (NC1)[d] (Pool$_x$) | E:T Ratio | Pool PHA | NC1 PHA | K562 |
| Without | 100:1 | 56 | 6 | 69 |
| IL2 | 50:1 | 51 | 4 | 63 |
| | 25:1 | 39 | 4 | 54 |
| With | 100:1 | 62 | 7 | 65 |
| IL 2 | 50:1 | 56 | 7 | 61 |
| | 25:1 | 52 | 6 | 57 |

B2. Normal PBL after stimulation by a single unrelated individual

| | | % Cytotoxicity ($^{51}$Cr Release) Target Cells | | |
|---|---|---|---|---|
| (NC1) (NC2$_x$) | E:T Ratio | NC2 PHA | NC1 PHA | K562 |
| Without | 100:1 | 34 | 2 | 63 |
| IL2 | 50:1 | 30 | 3 | 67 |
| | 25:1 | 28 | 1 | 58 |
| With | 100:1 | 67 | 3 | 75 |
| IL 2 | 50:1 | 55 | 3 | 74 |
| | 25:1 | 37 | 3 | 67 |

C. AF - PBL (Nezelof's Syndrome)

| | | % Cytotoxicity ($^{51}$Cr Release) Target Cells | |
|---|---|---|---|
| Effector Cells | E:T Ratio | Pool PHA | K562 |
| (A.F. PBL) (pool$_x$) | 50:1 | 5 | 23 |
| (A.F. PBL) (pool$_x$) + IL 2 | 50:1 | 9 | 77 |

[a]Cytotoxic responses of patients J.V., A.F., and a normal individual after 6 day in vitro mixed lymphocyte culture in the presence and absence of exogenous hp IL 2.
[b]Pool PHA denotes day 3 PHA lymphoblasts from a pool of PBL from 10 normal individuals.
[c]x denotes 4000 rads irradiation.
[d]NC1 and NC2 denote two unrelated normal control individuals.
NC1 PHA and NC2 PHA denotes day 3 PHA lymphoblasts from PBL of NCI and NC2.

Case Summary—A.F.

A.F. is a 3-year-old patient with Nezelof's syndrome, who was the product of a normal term pregnancy and delivery. During his first 2 yr of life, he was noted to have severe eczema, bronchiolitis, and otitis, but he did not require hospitalization. At the age of 2, he developed bilateral interstitial pneumonitis as a result of enterovirus and rapid, progressive respiratory failure, requiring 2 weeks of respiratory support on a ventilator.

Over the next 6 months, he was hospitalized three more times for pneumonia. In spite of prolonged administration of antibiotics, his chest x-ray failed to improve. An open lung biopsy grew *Hemophilus influenzae*. Evaluation revealed moderate neutropenia (1000 to 1500 polymorphonuclear leukocytes (PMN) /microliter) and eosinophilia. A sweat test was negative and alpha-1 antitrypsin levels were normal. Although 70% of his PBL formed E-rosettes and stained with monoclonal antibodies to the sheep red blood cell (SRBC) receptor, the majority of these bound only three SRBC). In contrast, only 22% of his PBL bound the T cell specific monoclonal antibody OKT3, whereas 20% bound OKT4 and 15% bound OKT8. Fifteen per cent of his cells were SIg positive.

After stimulation with PHA and Con A, his proliferative responses were only 263 and 283 cmp $^{14}$C TdR in contrast to the 14,700 and 9200 cpm of control PBL. Nucleoside phosphorylase and adenosine deaminase levels were normal. Serum immunoglobulin were normal to slightly elevated (immunoglobulin G (IgG) 1516 mg/100 ml, immunoglobulin A (IgA) 155 mg/100 ml, and immunoglobulin M (IgM) 285 mg/100 ml). He was, however, unable to produce specific immunoglobulin in response to pneumococcal or typhoid vaccines, although a titer of 1:32 to herpes simplex was noted. Based on these findings, Nezelof's T cell deficiency was diagnosed.

He was referred to our institution for transplantation of fetal liver and thymus. His post-transplant course has been complicated by multiple episodes of otitis, penumonitis, sinusitis, and a transient eosinophilic leukemoid reaction. He is presently more than 1-year post-transplant without any evidence of improved T cell function and without evidence of engraftment of the fetal tissues by either HLA or cytogenetic analyses.

Characterization of the immunologic defect of patient A. F.: In response to stimulation with PHA and OKT3, it was found the A. F.'s PBL were able to generate 0.6U/ml of IL 2 (Table III). The effect of exogenous IL 2 on the MLC and CML responses of the PBL of this child is shown in Tables IVC and VC. In the absence of IL 2, minimal proliferation was seen in response to pooled or single alloantigenic stimulation. When exogenous hp IL 2 was added, a substantial boost in proliferation was seen in medium alone without alloantigen. However, no additional boost in proliferation was seen in response to the combination of alloantigen plus IL 2. After 6-day MLC in the absence of IL 2, NK-like cytotoxicity against k562 was observed, but T cell-mediated cytotoxicity against PHA lymphoblasts was minimal to absent. In the presence of hp IL 2, NK activity was boosted further, but significant T cell mediated cytotoxicity was still not generated.

A.F.'s response to mitogens in the presence of hp IL 2 differed from the response of J. V. as well as from the response of normal individuals. Although A. F.'s PHA response was boosted sixfold, the response to OKT3 increased only threefold. In contrast, J. V.'s responses to both mitogenic stimuli were boosted over 10-fold, whereas normals were boosted twofold or less. This differential response to PHA plus IL 2 vs OKT3 plus IL 2 was unique to A. F. This finding is in agreement with the previous observation that the majority of A. F.'s SRBC rosetting lymphocytes lacked the OKT3 antigen.

The effects of IL 2 on MLC response in three patients with severe combined immunodeficiency (SCID): Three patients with classical SCID were studied to assess the effects of IL 2 on their response to alloantigen. In all three children, there was no boosted in the proliferation of their PBL above that seen in medium alone irrespective of the addition of alloantigen and/or hp IL 2. A representative MLC study from one child, A. W., is shown in Table IVD.

Early studies of the soluble factors released during immune reactions identified a variety of helper "activities" that could substitute for T cells in in vitro assays [Plate, J.M.D. (1976) Nature 260:329; Finke, J. H., et al. (1977) Nature 267:353; Wagner, H., et al. (1978) J. Exp. Med. 148:1523; Farrar, J. J., et al. (1978) J. Immunol. 121:1353; Baker, P. E., et al. (1978) J. Immunol. 121:2168; Watson, J., et al. (1979) J. Immunol. 122:209; Watson, J., et al. (1979) J. Immunol 122:1633; Okada, M., et al. (1979) J. Immunol 122:2527; Okada, M., et al. (1980), J. Immunol. 125:850; and Hamaoka, T., et al. (1981) J. Immunol. 126:659]. Subsequently, it has been shown that many of these T cell helper activities represent the effects of a single lymphokine, IL 2, in the various assay systems employed [Gillis, S., et al. (1978), J. Immunol. 120:2027; Watson, J. et al. (1979) J. Exp. Med. 150:849; Gillis, S., et al. (1979) J. Immunol. 124:1954; Kern, D. E., et al. (1981) J. Immunol. 127:1323]. The most direct demonstration of IL 2 activity is via its ability to support the long-term in vitro growth of activated T lymphocytes [Morgan, D. A., et al. (1976) Science 193:1007; Gillis, S. et al. (1978) Supra]. In addition, however, purified IL 2 preparations have been shown to provide "help" in inducing humoral responses to heterologous erythrocytes in nude mice (presumably via induction of helper T cells) [Farrar, J. J., et al. (1978) J. Immunol 121:1353; Watson, J., et al. J. (1979) Immunol. 122:209; Watson, J., et al. (1979) J. Immunol. 122:1633; Watson, J., et al. (1979), J. Exp. Med. 150:849]. Exogenous IL 2 also allows thymocytes and nude mouse spleen cells to develop proliferative responses to mitogen and antigen and to develop T cell-mediated cytotoxicity [Farrar, J. J., et al. (1978) Supra; Watson, J., et al. (1979) J. Immunol. 122:1633; Watson, J., et al. (1979) J. Exp. Med 150:849; Gillis, S., (1979) J. Immunol. 124:1954; Gillis, S. et al. (1979) J. Exp. Med. 149:1460; Wagner, H., et al. (1980) Nature 284:278]. In nude mice, the inability to generate adequate amounts of IL 2 appears to play a major pathophysiologic role in the T cell defects that are seen [Gillis, S., et al. (1979) Exp. Med. 149:1460), although this deficit may not be absolute (MacDonald, H. R., et al. (1982) J. Immunol. 129:521]. Diminished IL 2 synthesis has also been demonstrated in aged mice. Antigen-induced T cell proliferation, MLR, and CML responses that are normally impaired in these animals are all markedly enhanced when exogenous IL 2 is added [Thoman, M. L., et al. (1982) J. Immunol., 128:2358].

Evidence has also accumulated that IL 2 is necessary for the generation of cytotoxicity by normal T lymphocytes. Metabolically inactivated (UV- or heat-treated) stimulator cells fail to induce the in vitro generation of CTL unless exogenous IL 2 is added to the culture medium [Kern, D. E., et al. (1981) J. Immunol. 127:1323]. Addition of a monoclonal antibody to IL 2 is capable of abrogating the proliferative response of T cells to mitogen and the development of cytotoxicity in in vitro mixed lymphocyte culture [Gillis, S., et al. (1981) J. Exp. Med. 154:983]. Taken together, these data argue quite strongly that IL 2 plays an important role in the development of a variety of normal T cell responses. They also suggest that some human disorders of T cell incompetence might result from defects in the production of and/or response to IL 2.

We have attempted to test this hypothesis by studying the effect of highly purified IL 2 on in vitro assays of T cell function in children with primary T cell deficiencies. In one child with Nezelof's T cell deficiency, J. V., the available evidence would pointtoward an IL 2-related defect. This child was deficient in his ability to product IL 2. Moreover, his proliferative response to T cell mitogens and alloantigen were markedly improved when exogenous IL 2 was added. Finally, in the presence of hp IL 2, he was able to generate cytotoxic effector lymphocytes after in vitro mixed lymphocyte culture. This child would therefore appear to have suffered from an immunologic defect similar to that seen in nude or aged mice.

These observations and the desperate clinical circumstances led to the in vivo trial of hp IL 2 this patient. The appearance of increased numbers of lymphocytes in the draining lymph nodes suggests that subcutaneously administered hp IL 2 produced an in vivo effect on the patient's T cells.

A different pattern of in vitro response was seen in the second Nezelof's patient, A. F. This child was less deficient in his ability to produce IL 2 than was J. V. His cells were also less susceptible to the growth-promoting effects of hp IL 2 after stimulation with mitogens. In MLC, increased proliferation was seen in the presence of IL 2, irrespective of whether additional allogeneic stimulation was provided. In cytotoxicity assays, NK-like activity was strongly boosted whereas T cell lysis of PHA lymphoblasts was not. In this context, it is noteworthy that NK cells in mouse and man have been shown to be sensitive to the growth-promoting properties of IL 2 [Dennert, G. (1980) Nature 287:47; Nable, G., et al. (1981) J. Exp. Med. 153:1582; Kuribayashi, K., et al. (1981), J. Immunol. 126:2321; Sugamura, K., et al. (1982), J. Immunol. 128:1749; Pawlec, G., et al. (1982), J. Immunol. 128:1892; Flomenberg, N., et al. (1982), J. Cell. Biochem. (suppl. 6): 25 and Kornbluth, J., et al. (1982) J. Immunol. 129:2831].

Moreover, although T cells require activation to become IL 2 sensitive, this may not apply to NK cells (Kornbluth, J., et al. (1982) Supra). Normal individuals also show increased proliferation in response to autologous stimulation plus IL 2. Lesser degrees of proliferation are also seen with highly purified IL 2 without autologous stimulation after 5 to 6 days of culture. These responses may therefore represent the proliferation of NK cells that may not require triggering to become IL 2 sensitive. This proliferative response may also partially reflect the expansion of T cell populations previously activated in vivo. NK active cells expressing a "non-T-cell" phenotype (SRBC receptor positive by Leu1/OKT1, Leu2a/OKT8, Leu3a/LKT4, and Leu4/OKT3 negative) can be grown in conditioned medium from the peripheral blood of normal individuals [Kornbluth, J., et al. 1982 Supra; Flomenberg, N., et al. (1983), J. Immunol. 130:2635; Herberman, R.B. (1982), Transplantation 34:1] as well as from A.F. and other T cell-deficient patients. This child, therefore, seems to possess IL 2 responsive NK cells, but unlike J. V., his T cell defect cannot be attributed solely to subnormal IL 2 production. A. F. would therefore appear to be suffering from a different pathophysiologic defect than J. V. The variation between these two patients illustrates the potential utility of this type of immunologic phenotyping in characterizing immune defects. Although initially felt to be suffering from the same clinical disorder, these children clearly had different pathogenetic defects underlying their T cell deficiencies. Clearly, other cytokines derived from either monocytes or T cells are involved in the generation of T cell response (Larsson, E. L., et al. (1980) Nature 283:664, Raulet, D. H., et al. (1982) Nature 296:754). As these various factors become available in relatively pure form and in sufficient quantity, further dissection of clinical T cell defects may well become possible.

None of the children with SCID demonstrated any change in their proliferative response in MLC in the presence of hp IL 2. A recent study (Lopez-Botet, M., et al. (1982), J. Immunol. 128:679) reported an absence of IL 2 synthesis in SCID. In addition, this study demonstrated that exogenous IL 2 did not alter the proliferative response to PHA stimulation in SCID. These combined results suggest that both the production of the response to IL 2 are impaired in this disease.

Only one of these five children with primary T cell deficiencies therefore had the combination of a defect in endogenous IL 2 production, but preservation of the ability to respond to exogenous IL 2. In this child, that IL 2 was capable of exerting some in vivo effects on T lymphocytes. These findings together raise the possibility that purified cytokines may ultimately have therapeutic potential in appropriately selected patients with immune deficiency states. We have recently had the opportunity to study an additional patient with Nezelof's syndrome. This child's proliferative and cytotoxic responses to alloantigen with and without hp IL 2 were strikingly similar to those of A. F.

Interleukin 2 (IL2), also known as T cell growth factor, can be produced by all T cell subsets (Meuer, S. C., et al., (1982), J. Immunol. 129:1076; Welte, K., et al. (submitted) OKT8 antibody inhibits OKT3 induced IL 2 production and proliferation in OKT8+ cells.) and NK cells in response to mitogenic or antigenic stimulation. The same stimulus also leads to expression of IL2 receptors on IL2 responder cells, which can be of any T cell or of NK cell subtype [Meuer, S. C., et al. (1982) Supra; Welte, K., et al. (submitted) Supra; Domzig, W., et al. (1983) J. Immunol. 130:1970; Flomenberg, N., et al. J. Immunol. in press]. The binding of IL2 to its receptor on appropriately activated responder cells leads to cell proliferation and clonal expansion of the activated responder cell subset(s) [Meuer, S. C., et al. (1982) Supra; Welte, K., et al. (submitted) Supra; Domzig, W., et al. (1983) J. Immunol. 130:1970; Flomenberg, N., et al. J. Immunol. in press; Welte, K., et al. (1982) J. Exp. Med. 156:454].

Beyond its physiological role in maintaining and expanding cell mediated immunity, alterations in IL2 production and response have been postulated to play a pathophysiological role in certain lymphoid leukemias [Ruscetti, F. W., et al. (1981) Blood 57:379; Mertelsmann, R., et al. (1981) Blut 43:99; Venuta, S., et al. (1983), Blood 61:781].

Since T cells and NK cells are considered to play an important role in the immune responses to tumor cells and infectious agents, we investigated (a) endogenous IL2 production, (b) proliferative response to endogenous IL2, as well as (c) the proliferative response to highly purified human IL2 (HP IL2) in a variety of human leukemias and immunodeficiency states (IDS). In the majority of patients, defective mitogen responses were found to be associated with IL2 production defects [Ciobanu, N., et a. (1983) J. Clin. Immunol. 3:332;

Welte, K., et al. (in press) Human Interleukin 2 in Modern Frends in Human Leukemia V, Springer Verlag, N.Y.]. Furthermore, addition of highly purified human IL2 [Welte, K., et al. (1982), J. Exp. Med. 156:454] led to at least partial correction of diminished in vitro proliferation in the majority of these patients [Ciobanu, N., et al. 1983 Supra; Welte, K., et al. (in press) Human Interleukin 2 Supra; Flomenberg, N., et al. (1983) J. Immunol. 130:2644]. Based on these observations, in vivo animal studies and combined phase I and II clinical trial of human IL2 were initiated.

Highly Purified Human IL2 (hpIL2)

IL2 was purified 40,000-fold from human lymphocyte CM, costimulated with Daudi cells as previously described in detail above (Welte, K., et al. 1982 Supra). The IL2 exhibited a single peak of 14,500 daltons by SDS-PAGE and HPLC. The specific activity of the final product was $10^6$U/mg protein. The IL2 assay and definition of units were as described previously above (Welte, K., et al. 1982 Supra). The hp IL2 preparation was sterile and nonpyrogenic, both in the limulus assay and in rabbits. In preliminary toxicity studies, hpIL2 was found to be non-toxic in mice (5,000 U/day×15 days, equivalent to 600,000 U/m$^2$×15 days). It is free of CSF, BGF, BIF, i.e. colony-stimulating factor, B cell growth factor and B cell inducing factor (also previously known as T cell replacement factor and BDF) respectively, alpha and gamma-interferon activities and is biologically active in vitro on both human and murine IL2 responder cells.

Further Studies of Correction of Immunodeficiency States in Man by highly purified IL2 (hpIL 2)

Expansion of Cytotoxic Precursors by hpIL2 in mice

C57BL/6 mice (2–12 per group) were given injections of L1210 tumor cells (5×10$^5$, s.c.) in the hind flank. Cyclophosphamide was administered (i.p. 180 mg/kg) 24 hr after tumor cell inoculation. On the 7th day after tumor implant, the inguinal nodes were removed and the cells were washed, counted and mixed with $^{51}$Cr-labelled target cells in a 5-hr $^{51}$Cr release assay. This in vivo lymph node assay elicits a local cytotoxic response with n detectable cytotoxic activity in the contralateral node or spleen. In mice receiving IL2, hpIL2 was infused subcutaneously by the use of osmotic infusion pumps (Alza Corp., Palo Alto, CA). Details of the experimental protocol have been described elsewhere [Merluzzi, V. J., et al. (in press) J. Immunol.].

In Vitro Studies In Man

Patients with the disease categories detailed in Table VII were followed at Memorial Hospital. Ten ml of heparinized blood was drawn upon obtaining informed consent. Lymphocytes were separated and phenotyped as previously described (Venuta, S., et al. (1983), Blood 61:781). Cell proliferation was measured in the absence and presence of 10 U/ml hpIL2 on day 3 upon stimulation with medium alone (RPMI 1640, 10% fetal calf serum), PHA, OKT3 or PAN T2.

Pan T2 is an IgG1 anti-human T cell monoclonal antibody which reacts with a different epitope of the same antigenic complex that is recognized by OKT3 (Venuta, S., et al. (1983) Supra). Supernatants of identical cultures were harvested after 24 hours and assessed for endogenous IL2 production as described above.

Phase I Trial In Man

Standard phase I criteria for patient selection were used. The protocol was approved by the Institutional Review Board. Informed consent was obtained from each patient. To be eligible for this study patients were required to show in vitro(a) defective proliferative responses to at least one of three mitogens (PHA, monoclonal antibodies OKT3, Pan T2), and (b) at least at 100% increment of proliferative response upon addition of IL2 (10 U/ml) in at least one of the three mitogen assays.

IL2 was administered subcutaneously to achieve maximum lymphatic drainage. In the first phase of the study (Phase A: "toxicity screen"), three patients were treated with escalating doses. In the first patient, dosages were increased daily to a maximum of 1,000 U/day. In the two subsequent patients, IL2 was administered subcutaneously by 24 hr infusion to more closely parallel the mode of administration used in the animal study. Dosages in these two patients were escalated every 3rd day starting at 300 U to a maximum of 4,000 U/day for 3 days over a total of 21 days. Since no toxicity was seen in these three patients, subsequent patients received IL2 at a constant daily dose s.c. for two weeks, followed by a two-week treatment-free interval. Dosages were escalated either in patients already on study after the two-week treatment-free interval or in patients newly entering the study.

Because of logistic considerations, hp IL2 was administered as a single daily s.c. injection. When starting on hpIL2 for the first time, the patient received an intradermal test-dose of 100 U and in the absence of any local reaction received the full dose one hour later. Following the first dose of IL2, vital signs were monitored every 30 min for 4 hours. In vitro tests performed at weekly intervals included complete blood counts, differential and reticulocyte count, T cell proliferation in response to PHA, OKT3 and Pan T2 in the presence and absence of 10 U/ml hpIL2 (Ciobanu, N., et al. 1983 Supra) cell surface marker studies including OKT3, OKT4, OKT8 and Leu 4 (Venuta, S., et al. 1983 Supra; Ciobanu, N., et al. (1983) Supra) as well as determination of NK activity with K562 as target (Flomenberg, N., et al. (in press) J. Immunol.). Details of the various techniques have been described (Welte, K., et al. (submitted) Interleukin 2; Domzig, W., et al. (1983) Supra; Flomenberg, N., et al. (in press) Supra; Welte, K., et al. (1982) Supra; Mertelsmann, R., et al. (1981) Blut 43:99; Venuta, S., et al. (1983) Supra; Ciobanu, N., et al. (1983) Supra; Welte, K., et al. (in press) Supra; Flomenberg, N., et al. (1983) J. Immunol. Supra; Merluzzi, V. J. et al. (in press) J. Immunol.). Every two weeks, biochemical screening profile, serum immunoglobulins, immunoelectrophoresis, PT, PTT and urinalysis were performed.

The clinical trial was designed to yield information on both, potential toxicity (phase I) as well as biological activity and efficacy (Phase II). While standard phase I/II chemotherapy studies are based on the presumption that maximum tolerated dose levels are also the most efficacious dose levels, this hypothesis might not extend to trials of biological response modifiers.

Murine Studies

Cyclophosphamide (CY) has been shown to be one of the most potent anti-cancer agents available. However, its strong immunosuppressive properties limit its full potential, since several studies have shown that the use of CY as an effective antitumor agent depends upon intact host immunity [Cheever, M. A., et al. (1980), J. Immunol. 124:2137; Cheever, M. A., et al. (1980) J. Immunol. 125:711; Lubet, R. A., et al. (1978) J. Nat'l. Cancer Inst. 61:897; Moore, M., et al. (1973) Int. J. Cancer 11:358].

Spleen cells from mice treated with high single doses of CY are unable to generate normal cytotoxic T-lymphocyte (CTL) response in vitro (Merluzzi, V. J., et al. (1981) Cancer Res. 41:850). This low response, however, can be reconstituted by the addition of T helper cells to the culture system (Merluzzi, V. J., et al. (1980) Int. J. Immunopharmacol 2:341) or crude mixed lymphocyte culture (MLC) supernatants (Merluzzi, V. J., et al. (1981) Supra).

Since production of helper and differentiation factors for cytotoxic cells is one of the properties of T-helper cells and IL2 is one of the predominant lymphokines generated in MLC, we have analyzed human hpIL2 for its ability to recover in vitro and in vivo cytotoxic activity in mice pre-treated with high single doses of CY. These high doses of CY have been shown to be very active against murine L1210 leukemia (Skipper H. E., et al. (1964) Cancer Cancer Chemother Rep. 35:1), but also to be highly immunosuppressive (Merluzzi, V. J., et al. (1981) Cancer Res. 41:3663). We have selected highly purified human IL2 because hpIL2 is the most highly purified IL2 available and is active on murine lymphoid cells (Welte, K., et al. (1982) J. Exp. Med. 156:454). In addition, this in vivo experimental system should serve as a relevant pre-clinical model for a clinical trial of hpIL2 in immunosuppression caused by antineoplastic therapy.

Mice and Cell Lines. Male C57BL/6 (H-$2^b$) and DBA/2 (H-$2^d$) mice were obtained from the Jackson Laboratory, Bar Harbor, ME. P815-X2 (H-$2^d$) mastocytoma cells and L1210-CYR (H-$2^d$) leukemia cells were maintained by weekly i.p. passage in syngeneic DBA/2 mice. The L1210-CYR cell line is a CY-resistant subline of L1210 and described previously [Merluzzi, V. J., et al. (1981) Cancer Res. 41:3663]. The AKSL thymoma cell line (H-$2^k$), derived form a spontaneous AKR leukemia, and the YAC lymphoma cell line (H-$2^{d/k}$) were maintained by in vitro passage in RPMI 1640 culture medium containing 10% fetal calf serum (FCS). The P815, L1210-CYR and AKSL cell lines are insensitive to classical natural killer (NK) cells. The YAC cell line is sensitive.

Preparation of Spleen Cells. C57BL/6 spleen cells were prepared for in vitro culture in a manner similar to that described by Mishell and Dutton [(1967) J. Exp. Med. 126:423]. Briefly, spleens were aseptically removed and gently teased into suspension in balanced salt solution (BSS). Large debris were allowed to settle at 0° C. for 5 min, and the cells remaining in the supernatant were aspirated, washed 3 times in BSS, and adjusted to the desired concentration in RPMI 1640 (Grand Island Biological Co., Grand Island, NY) containing $5 \times 10^{-5}$M 2-mercaptoethanol and 10% specifically-screened heat-inactivated (56° C., 30 min) FCS.

Determination of cytotoxic activity. Cytotoxic activity was measured by a modification on the $^{51}$Cr release assay as described by Baum and Pilarski [(1978) J. Exp. Med. 148:1579]. Briefly, $2-4 \times 10^6$ tumor target cells were mixed with 250 microCi $^{51}$Cr (New England Nuclear, Boston, MA) in a volume of 0.6 ml in RPMI 1640 medium and incubated for 1 hr. After washing and counting, 100 microliters containing $5 \times 10^3$ $^{51}$Cr-labeled target cells were added to each culture well. The responder cells were harvested, washed and counted in incubated at several L/T ratios with $^{51}$Cr-labeled target cells in microculture plates. The cultures were mixed with a multichannel pipettor, centrifuged for 3 min at $30 \times g$, and then incubated at 37° C. for 5 hr in a humidified atmosphere with 5% $CO_2$. At the end of 5-hr incubation period, the plates we centrifuged at $400 \times g$ for 5 min, and the amount of radioactivity released into 0.1 ml of the supernatant of each culture was determined in a Nuclear Chicago gamma counter. The percentage of specific $^{51}$CR release on quadruplicated cultures was calculated in the following manner:

$$\frac{\text{Experimental release} - \text{spontaneous release}}{\text{Total release} - \text{spontaneous release}} \times 100$$

Total releasable counts were determined by diluting the $^{51}$Cr-labeled target cells in distilled water. Spontaneous release for the 5-hr assay was less than 20%.

In vivo generation and assay of cytotoxic cells. C57BL/6 mice (2-12 per group) were given injections of L1210-CYR tumor cells ($5 \times 10^5$, subcutaneously) in the hind flank. CY was administered (i.p. 180 mg/kg) 24 hr after tumor cell inoculation. On the 7th day after tumor implant, the inguinal nodes were removed and the cells were washed, counted, and mixed with $^{51}$Cr-labeled target cells in a 5-hr $^{51}$Cr-release assay as described above. This in vivo lymph node assay elicits a local cytotoxic response with no detectable cytotoxic activity in the contralateral node or spleen.

When cytotoxic activity was measured at several lymphocyte:target cell ratios, cytotoxic activity was quantified as a function of the logarithm of the effector:-target cell ratio. The data was plotted and the effector:-target cell ratio necessary to obtain 33% lysis was extrapolated from the linear portion of the curve. This number of effectors was arbitrarily taken as a "lytic unit" (L.U.). The number of L.U./10 effectors was calculated.

IL2 infusion in vivo. IL2 was infused subcutaneously by the use of osmotic infusion pumps (Alza Corp., Palo Alto, CA). Mice were anesthetized (325 mg/kg chloral hydrate) for a period of 20–30 min. The mice were shaved (from right ear and midback to the posterior section of the rib cage) and the skin was then washed with 70% ethanol. From above the shoulder blade, the shaved skin was pinched between the thumb and index finger and a small disc-shaped incision was made. The incision was then further extended to the Panniculus carnosus layer. Hemostats were inserted into the incision and used to create a subcutaneous trough extending to the right inner thigh. The minipump was then inserted portal-end first anterior to the right inguinal lymph node. The would was then closed with two 9 mm would clips (Clay Adams, Parsippany, NJ). All procedures were accomplished with sterile instruments and materials. The osmotic minipumps were weighed before and after filling with IL 2 and all infusion pumps were cut in cross section at the end of each experiment to check for complete elution of IL2. The weight of the minipumps was subtracted from the total weight of each mouse when injecting CY on a mg/kg basis. Preliminary experiments have shown that anesthesia and/or insertion of pumps had no effect on general immunological parameters of immune reactivity (antibody production and CTL generation). Several lots of osmotic pumps were previously checked for in vitro elution of IL2 into tissue culture medium and all were shown to be positive. Empty or RPMI-filled osmotic pumps did not alter the in vivo CTL response. The pumps were implanted 2 hr. before tumor cell inculation.

Cyclophosphamide. The sterile CY-sodium chloride preparation (Mead Johnson & Co., Evansville, Ind) was dissolved in distilled water to a concentration of 20 mg/ml. Individual mice were weighed and given i.p. injections of CY. All mice received a single dose of 150 mg/kg 48 hr before removing spleens for culture or 180 mg/kg after tumor implant for in vivo studies. There was a 40–75% reduction in spleen and lymph node cellularity after CY treatment. The lymphoid cells of treated mice and normal littermate controls were more than 80% viable as determined by Trypan blue exclusion.

Anti-Thy 1.2 and Complement (C′). Lymphoid cells ($10^6$–$10^7$) were treated with monoclonal anti-Thy 1.2 serum (1/100) obtained form Dr. Ulrich Hammerling (Sloan-Kettering Institute) for 45 min. at room temperature. Rabbit C′ (1/12) (Cedarlane Laboratories, Hornby, Ontario, Canada) was then added for 45 min. at 37° C. The cells were washed in BSS, counted and adjusted to the desired concentration in RPMI tissue culture medium.

Initial experiments were designed to test the effect of hpIL2 on NK effector cell activity in a 5-hr $^{51}$Cr-release assay. Normal C57BL/6 spleen cells and spleen cells from CY-treated mice were not able to lyse the NK insensitive P815 target in the absence or presence of IL2, while the YAC target was effectively lysed by all fresh effector cells. There was no appreciable difference in lytic activity against YAC in the absence or presence of IL2 at the concentration used (25 U/ml) and NK effector cells were not affected by previous treatment with CY. When the spleen cells were cultured for 72 hr with or without IL2, differences in lytic activity became apparent (Table VIA).

Spleen cells from normal mice or mice pretreated with CY and cultured alone displayed very little lytic activity against P815 and YAC target cells. If the spleen cells were cultured in the presence of highly purified human IL2, both P815 and YAC target cells were effectively lysed by both normal and CY-pre-treated spleen cell preparations. These results indicate that CY does neither eliminate NK effector cells nor the precursors that lead to cytotoxic activity driven by purified IL2 in vitro.

The fresh NK effectors were not eliminated by treatment with X-irradiation or anti-Thy 1.2 and C′ before analysis in the Cr release assay. Spleen cells cultured for 72 hr in the presence of purified IL2, however, were no longer able to express lytic activity to NK-sensitive (YAC) or NK-insensitive (P815, L1210-CYR) target cells after treatment with anti-Thy 1.2 and C′.

TABLE VIA

Effect of highly Purified Human IL2 on Cytolytic Effector Cells

| Effector Cells[a] | IL2[b] | % specific $^{51}$Cr release | | |
|---|---|---|---|---|
| | | YAC | P815 | L1210-CYR |
| B6 | — | 15 + 0.4[c] | 3 + 0.2 | 1 |
| B6 | + | 56 + 1.5 | 37 + 1.9 | 28 + 0.8 |
| B6-CY | — | 1 | 1 + 0.3 | 1 |
| B6-BY | + | 55 + 2.9 | 66 + 0.9 | 53 + 2.1 |

[a]Effector cells were derived from normal (B6) or CY-treated B6 mice (B6-CY) and cultured for 72 hr in the presence or absence of IL2.
[b]25 U/ml
[c]Mean + S.E.M. of quadruplicate cultures.

These results suggest that IL2 can activate precursors of cytotoxic cells in vitro, and that the effector cells are thymus-derived T cells, active against both, NK-sensitive and NK-insensitive target cells.

Initial experiments were designed to test the effect of human hp IL 2 on the generation of splenic cytotoxic cells in vitro. In vitro cultured spleen cells from both normal and CY-pretreated mice did not elicit cytotoxic activity to P815 target cells in the absence of alloantigen. When mitomycin C-treated P815 target cells in the absence of alloantigen. When mitomycin C-treated P815 stimulator cells were present in the culture system, spleen cells from normal C57BL/6 mice generated effective cytotoxic activity whereas spleen cells from CY-treated did not. When human IL2 was present in the culture system, low doses (3.125–12.5 U/ml) restored cytotoxic activity to CY-treated spleen cells when P815 stimulator cells were present in the cultures. When high doses of IL2 (50 U/ml) were used, nonspecific cytotoxic activity was seen. That is, spleen cells from both normal and CY-treated mice elicited cytotoxic activity in the absence of alloantigen. In both cases, the precursors of the cytotoxic effector cells were resistant to CY pretreatment. Both specific and nonspecific cytotoxic effector cells generated in vitro were sensitive to anti-Thy 1.2 and C′.

We next investigated the effects of highly purified human IL2 on cytotoxic cell generation in vivo. hp IL 2 alone, in the absence of antigen, was not sufficient to generate nonspecific cytotoxic cells in vivo. In addition, IL2 administered to normal mice in combination with antigen either did not alter lytic activity of suppressed cytotoxic activity. If the mice were immunosuppressed by CY, however, lytic activity was restored by the infusion of IL2 (Table VII). The effector cells were again, as in vitro, Thy 1.2 positive but unlike the in vitro responses, lytic activity was specific for L1210-CYR. Further studies explore different dose schedules of IL2 to assess the effect of higher IL2 concentrations on NK cell and non-specific cytotoxic effector cell activities in vitro and in vivo.

TABLE VII

In Vivo Effect Of Highly Purified Human IL2 On Cytotoxic Activity Against L1210-CYR Target Cells

| Group[a] | IL2 | % Secific $^{51}$Cr Release | | | L.U.[b] |
|---|---|---|---|---|---|
| | | 25/1[c] | 12.5/1 | 6.25/1 | |
| B6 | — | 45 + 1.0[d] | 31 + 1.2 | 15 + 1.2 | 14.08 |
| B6-CY | — | 16 + 1.8 | 12 + 0.6 | 10 + 0.6 | 0.14 |
| B6-CY | 0.5 U/hr | 59 + 0.8 | 48 + 1.5 | 18 + 0.4 | 21.38 |

[a]B6 (saline-treated); B6-CY (cyclophosphamide-treated), osmotic pumps were inserted on day 0; L1210-CYR injected 4 hr later; CY injected 24 hr later.
[b]Lytic Units/$10^6$ cells.
[c]Lymphocyte: target cell ratio
[d]Mean + S.E.M. of quadruplicate cultures The following experiments were performed to test the effect of human hp IL 2 in vivo. Table VIB shows the results of two experiments in which human IL2 restores cytotoxic activity in lymph nodes of mice immunosuppressed by high doses (180 mg/kg) of CY. The effector cells are Thy 1.2+ and are specific for immunizing L1210-CYR antigen. The AKSL target (H-2 $^{k/k}$) is not lysed by the effector cells. The AKSL target is susceptible to lysis by specific anti-k/k CTL and by in vitro-induced cytotoxic cells in the presence of high doses of IL2 Table VIC shows the results of an experiment in which human IL2 was tested for its effects on non-tumor-bearing mice and on tumor-bearing control mice not injected with CY. In Table VIC Experiment #1, lymph node cells from normal C57BL/6 mice showed some natural cytotoxic activity only against the NK-sensitive YAC target cells. When IL2 was infused, the cytotoxic activity was not enhanced and was in fact lower than the control. This was again shown in Table VIC Experiment #2 where the only appreciable cytotoxic response was seen against the YAC target cell. No enhancement of cytotoxic activity was seen by IL2 infusion. Mice injected with CY alone showed similar results (Table VIC lines 5 and 6, Expt #1). When normal C57BL/6 mice were injected with L1210-CYR, normal cytotoxic activity was observed with no appreciable enhancement of the cytotoxic response by IL 2 infusion.

The experiments presented here show that highly purified human IL2 stimulates cytotoxic cells in vitro and in vivo.

TABLE VIB

Effect of Human IL2 on Cytotoxic Activity In Vivo

| Group[a] | IL2[b] | % Specific $^{51}$Cr Release[c] 25/1[f] | 12.5/1 | 6.25/1 | Corr. Coef.[d] | L.U./ $10^6$ cells[e] |
|---|---|---|---|---|---|---|
| B6 | — | 45 ± 1.0[g] | 31 ± 1.2 | 15 ± 1.2 | .999 | 14.08 |
| B6-CY | — | 16 ± 1.8 | 12 ± 0.6 | 10 ± 0.6 | .981 | 0.14 |
| B6-CY | Fraction V | 59 ± 0.8 | 48 ± 1.5 | 18 ± 0.4 | .967 | 21.38 |
| B6 | — | 54 ± 0.3 | 33 ± 0.3 | 21 ± 0.8 | .987 | 18.08 |
| B6-CY | — | 16 ± 1.2 | 14 ± 0.6 | 13 ± 1.2 | .981 | <.01 |
| B6-CY | Fraction VI | 28 ± 1.3 | 23 ± 0.4 | 19 ± 0.9 | .998 | 3.58 |

[a]B6 (saline-treated C57BL/6); B6-CY (cyclophosphamide at 180 mg/kg), osmotic pumps were inserted on day 0; L1210-CYR injected 2 hr later; CY was injected 24 hr later. The CTL assay was performed on day 7 after tumor implant.
[b]Interleukin 2: blue agarose (Fraction V) and red agarose (Fraction VI) delivered by infusion at 0.5 U/hr (500 U/ml).
[c]5 hr assay vs $^{51}$Cr-labeled L1210-CYR target cells.
[d]Correlation coefficient
[e]Lytic Units/$10^6$ cells.
[f]Lymphocyte: target cell ratio
[g]Mean ± S.E.M. of quadruplicate cultures.

TABLE VIC

Effect of Human IL2 on Cytotoxic Activity In Vivo (B) Non-tumor bearing mice and tumor bearing mice treated with saline only

| Group[a] | % Specific $^{51}$Cr Release[b] | | |
|---|---|---|---|
| | L1210-CYR | YAC | AKSL |
| Expt 1 | | | |
| B6 | <1 | 12 ± 0.4[c] | n.d.[d] |
| B6 + IL2 | <1 | 5 ± 0.4 | n.d. |
| B6 × L1210-CYR | 27 ± 0.1 | n.d. | n.d. |
| B6 × L1210-CRY + IL2 | 29 ± 1.2 | n.d. | n.d. |
| B6-CY | <1 | 5 ± 0.6 | n.d. |
| B6-CY + IL2 | <1 | 2 ± 0.2 | n.d. |
| Expt 2 | | | |
| B6 | 3 ± 0.1 | 35 ± 1.5 | 4 ± 1.8 |
| B6 +IL2 | 3 ± 0.3 | 22 ± 1.7 | 2 ± 0.9 |

[a]B6 (saline-treated C57BL/6); B6-CY (CY at 180 mg/kg); osmotic pumps were inserted on day 0; L1210-CYR injected 2 hr later (lines 3 + 4 only; CY was injected on day +1. The cytotoxic assay was performed on day +7. IL2 by infusion at 0.5 U/hr (500 U/m).
[b]$^{51}$Cr release at 5 hr; E/T = 50/1.
[c]Mean ± S.E.M.
[d]n.d. = not done

TABLE VID

Effect of Human IL2 on Cytotoxic Activity In Vivo (A) Characterization of Effector Cells

| Group[a] | IL2[b] | Treatment of Effector Cells[c] | % Specific $^{51}$Cr Release[d] | |
|---|---|---|---|---|
| | | | L1210-CYR | AKSL |
| B6 | — | none | 31 ± 1.8[e] | <1 |
| B6-CY | — | none | <1 | <1 |
| B6-CY | + | none | 30 ± 1.8 | <1 |
| B6-CY | + | C' | 16 ± 2.2 | n.d.[f] |
| B6-CY | + | anti-Thy 1.2 + C' | <1 | n.d. |

[a]B6 (saline-treated C57BL/6); B6-CY (cyclophosphamide at 180 mg/kg); osmotic pumps were inserted on day 0; L1210-CYR injected 2 hr later; CY was injected on Day +1. The CTL assay was performed on day 7 after tumor implant.
[b]Interleukin 2; red agarose (Fraction VI) delivered by infusion at 0.05 U/hr (500 U/ml)
[c]Complement (C'); or anti-Thy 1.2 + C' before $^{51}$Cr release assay.
[d]% $^{51}$Cr release at 5 hr; ET = 12.5/1.
[e]Mean ± S.E.M. of quadruplicate cultures.
[f]n.d. = not done.

The effector cells are thymus-derived (T cells) as shown by their susceptibility to anti-Thy 1.2 and C' treatment. These highly purified preparations of IL2 lack detectable interferon (alpha and gamma), granulocyte-macrophage colony-stimulating factor, B-cell growth factor, thymocyte differentiating activity, and were free of any contaminating proteins judged by silver staining in SDS-PAGE. It remains to be determined whether lymphoid cells from normal or CY-treated mice, the IL2 preparations used, or both, contain a T-cell differentiation factor which has been described to act in concert with IL2 in promoting T-cell lytic activity [Raulet, D. H. et al. (1982) Nature 296:754].

Whether the effector cells for classical NK reactions and their precursors are different subsets of a common T-cell lineage is not yet clear. It is clear, though, that the cytotoxic precursors are resistant to CY and therefore are able to generate lytic activity in the presence of IL2.

We have shown that mice immunosuppressed by CY have a lower cytolytic capacity than normal littermates. Infusion of IL2 in a rate-controlled manner distal to the immunized lymph node enhances the low in vivo cytotoxic response. The cytotoxic cells again are thymus-derived effectors. It is not clear why IL2 infused into normal mice with or without antigen administration does not enhance cytotoxic activity. It is possible that medium components in vitro are acting together with IL2 in promoting non-specific T-cell-derived effectors which cannot be demonstrated in vivo and thus this in vitro system represents activity which can only be artifactual. Another possibility is differences in dose response kinetics in vivo and thus this in vitro system represents activity which can only be artifactual. Another possibility is differences in dose response kinetics in vivo and in vitro. Hefeneider et al. [(1982) J.

Immunol. 130:222]. We have demonstrated that in vivo administration of murine IL2 augments alloreactive CTL as well as NK cells. We have shown augmentation of CTL only in immunosuppressed mice, but differences in IL2 concentration and use of lymph node effector cells as opposed to splenic effectors may explain these differences.

CY is an ideal agent to combine with IL2 as an immunotherapeutic adjunct to its cytotoxic properties because in addition to being a strong antineoplastic agent, CY eliminates suppressor T cells [Röllinghoff, M. A. (1977) J. Exp. Med. 145:455], an IL2 inhibitor [Hardt, et al. (1981) J. Exp. Med. 154:262], and spares allocytotoxic precursors [Taswell, C. et al. (1980) Thymus 1:1119]. It should be noted that syngeneic CTL precursors may be more sensitive to CY than allogeneic CTL precursors [Hancock, E. J. (1982) Immunol. Immunother 14:54 and Hurme, M. (1979) J. Exp. Med. 149:290]. The syngeneic CY-resistant precursors can still be expanded however, with IL2 [Hancock et al. (1982) Supra]. The fact that CY spares some cytotoxic precursors and IL2 allows for their differentiation and/or proliferation can lessen this drug's negative impact upon the cellular immune system.

Since lymphokine therapy for neoplasia is becoming potentially important and much more feasible with the advent of adequate delivery systems and technological advances in protein purification it is possible to use these naturally-occurring biological response modifiers in clinical trials. Preliminary studies in humans suggest a role for IL2 in the restoration of the chemotherapy-suppressed mitogen response in vitro, as well as in vivo enhancement of immunological parameters in acquired and congenital immunodeficiency syndromes. The experiments presented here show that if precursor cells are spared by cytoreductive agents, the immunosuppressive effect of these agents may be counteracted in vivo by the adequate delivery of naturally-occurring lympholines.

Precursors of cytotoxic lymphoid cells obtained from mice treated with cyclophosphamide (CY) can be expanded in culture by alloantigens in the presence of purified human interleukin 2 (IL2). Similarly, hp IL2 delivered in vivo in a rate-controlled manner enhances cytotoxic activity in mice immunosuppressed by high doses of CY. The effector cells are Thy 1.2 positive and are not elicited in the absence of antigen.

In Vitro Studies in Man

IL-2 in Lymphoid Leukemias. Several lines of evidence suggest that the growth of human tumors is factor dependent and that tumor cells can be responsible for the production of these factors. We have investigated the possibility that the growth of certain lymphomas and leukemias is IL2 dependent and whether leukemogenesis is associated with any of these factors. We have investigated the possibility that the growth of certain lymphomas and leukemias is IL2 dependent and whether leukemogenesis is associated with alterations of the mechanisms regulating IL2 production and T cell proliferation. We have found that cALL and T ALL cells produce IL2 after PHA stimulation (Venuta, S., et al. 1983 Blood 61:781), and that these leukemias do not respond to the addition of Pan T2 which is mitogenic and induces IL2 production in normal lymphocytes (Venuta, S., et al. (1983) Supra). Daudi, a B lymphoblastoid line, is able to rescue the response of ALL to Pan T2 (Venuta, S., et al. (1983) Supra). These results indicate that leukemogenesis induces an alternation of the molecule which is recognized by Pan T2 and responsible for Pan T2 induced IL2 production. Since ALL cells present in the peripheral blood do not proliferate detectably in suspension culture in response to IL2, we hypothesized that IL2 is required by leukemic stem cells in order to proliferate and differentiate into more mature IL2 producing leukemic cells (Venuta, S, et al. (1983) Supra). Experiments demonstrating IL2-dependence of colony formation in the cALL cloning assay (Izaquirre, C. A., et al. 1981, Blood 57:823) support this conclusion (Feldman et al., submitted).

IL2 in Immunodeficiency States (IDS). Table VIII summarizes the cell proliferation and IL2 data in the patient groups studied. Defective proliferation of peripheral blood T cells in response to mitogens was found to be associated with defective IL2 production in all cases. Addition of IL2 at a concentration of 10 U/ml, which we found to be saturating for normal T lymphocytes tested under these conditions, restored cell proliferation partially or completely in the majority of patients.

TABLE VIII

IL2 Production and Proliferation +/−IL2 In Immunodeficiency

| Diagnosis | PHA (0.5%, v/v) | | | OKT3 (1.25 ng/ml) | | |
|---|---|---|---|---|---|---|
| | IL2 | −IL2 | +IL2 | IL2 | −IL2 | +IL2 |
| | U/ml cpm × 10³ | | | U/ml cpm × 10³ | | |
| AIDS[b] | 1.1 | 20 | 28 | 0.9 | 13 | 32 |
| Hemophilia | nt[a] | 52 | 58 | nt | 26 | 56 |
| CVI[c] | | | | | | |
| −IL2 responders | 0.6 | 43 | 78 | 0.5 | 32 | 55 |
| −IL2 non-responders | 0.9 | 14 | 18 | 0.5 | 16 | 16 |
| BMT[d] | 0.2 | 5 | 24 | 0.2 | 8 | 51 |
| Hodgkin's | nt | 5 | 13 | nt | 4 | 17 |
| Controls | 2.3 | 78 | 90 | 3.5 | 61 | 82 |

[a]not tested.
[b]acquired immunodeficiency syndrome
[c]common variable immunodeficiency
[d]bone marrow transplantation The relative increase of T cell proliferation achieved by addition of IL2 was significantly higher in all patient groups as compared to controls.

In a recent detailed analysis of IL2 production and response in the acquired immunodeficiency syndrome (AIDS), OKT3 appeared to be the most sensitive mitogenic stimulus to identify a proliferative T cell defect (Ciobanu, N., et al. (1983) Supra). Furthermore, the degree of proliferation in response to OKT3 appeared to be of prognostic significance. Patients incorporating less than 13,000 cpm in response to OKT3 exhibited significantly shorter survival than those with more than 13,000 cpm. It is of interest, that in vitro T cell proliferation could be boosted to more than 13,000 cpm by hp IL2 in all patients studied. Although the in vivo significance of this phenomenon remains to be determined, it provides a further rationale to attempt to restore defective T cell proliferation in vivo by administration of hpIL2.

Recently an aggressive form of Kaposi's sarcoma (KS) as well as an outbreak of opportunistic infections, mainly with Pneumocystis carinii and herpes-viruses, has been described in young homosexual males, reaching almost epidemic proportions in New York City and California [Friedman-Kien, A, et al. (1981), Morbid Mortal Weekly Rep. 301:305–308; Siegal, FP, et al. (1981), N. Engl. J. Med. 305:1439–1444; Gottlieb, MS, et al. (1981), N. Engl. J. Med. 305:1425-1431; Reiner, NE, et al. (1982), Ann Intern Med. 96:170-173]. Several studies have shown that these homosexuals with or without KS exhibit T-cell dysfunction, described as an increase in the percentage of suppressor/cytotoxic T-cell subpopulations (Gottlieb, MS, et al. (1981) Supra) or as a lower-than-normal ratio of helper to suppressor cells (Koziner, B, et al. (1982), N. Engl. J. Med. 306:933-934). Others found absent mitogen responses of peripheral blood lymphocytes (PBL) from homosexuals with KS and depressed natural killer-cell activity (Siegel, FP, et al. (1981), Supra).

It has been previously shown that the proliferative response to T lymphocytes to mitogenic (or antigenic) stimulation is dependent upon the release of a low molecular weight protein designated interleukin 2 (IL2) (Ruscetti, FW, et al. (1981), Blood 57:379-394). This laboratory has previously reported on the use of the T-cell-specific mitogenic monoclonal antibodies, OKT3 and Pan T2, in the analysis of IL2 production and response in human disease states [Venuta, S, et al. (1982), in UCLA Symposia in Molecular and Cellular Biology Vol. XXIV eds. E. Viteta and C. Fred Fox, New York, Academic Press, pp. 253-259]. Both reagents are able to induce IL2 release, expression of IL2 receptors, and, as a result, lymphocyte proliferation (Venuta, S, et al. 1982 Supra).

In view of the evidence that T lymphocytes from homosexual patients with KS have suboptimal proliferative responses to mitogen stimulation, as well as the data demonstrating a decrease in helper T cells, we studied the effect of both phytohemagglutinin (PHA) and mitogenic antibody stimulation on T-cell proliferation and IL2 production in peripheral blood lymphocytes from homosexuals with and without KS.

Patient Population. We have tested the peripheral blood mononuclear cells from 21 homosexual patients seen in the outpatient department at Memorial Hospital in the spring and summer of 1982 (Table XI). Twelve of them had biopsy-proven KS. Four patients had only generalized lymphadenopathy of a "reactive type" but were otherwise healthy. The remaining five patients had different opportunistic infections. None of the patients with either lymphadenopathy or opportunistic infections had associated KS. The herpes titers and T-cell characteristics of the patients as well as survival data are listed in Table XI. As controls we used 10 healthy heterosexual males, matched for age.

Lymphocyte Separation and Identification. The mononuclear cells from heparinized blood samples were separated by Ficoll-Hypaque density gradient centrifugation and used immediately. The lymphocyte fraction was reacted with a panel of anti-T-cell monoclonal antibodies (Ortho Pharmaceuticals, Raritan, NJ) that recognized all peripheral T cells (OKT3), helper T cells (OKT4), or suppressor T cells (OKT8) [Reinherz, EL, et al. (1979), N. Engl. J. Med. 301:1018-1022]. The percentage of cells binding specific mouse monoclonal antibodies was determined by indirect immunofluorescence on a cytofluorograph system 30 (Ortho Instruments).

Mitogen Stimulation of Lymphocytes. RPMI-1640 supplemented with 10% heat-inactivated fetal calf serum was used to prepare incubation media containing the following mitogens: (a) phytohemagglutinin (PHA; M form; GIBCO, Grand Island, NY), final concentration 0.5%; (b) OKT3 monoclonal antibody (Ortho, Raritan, NJ), final concentration 1 ng/ml; (c) Pan T2 is monoclonal antibody [produced by our laboratory [Wang, C. Y., et al. (1983) (submitted for publication)] final concentration 100 ng/ml. Briefly, Pan T2 is an $IgG_1$ anti-human T-cell monoclonal antibody which reacts with more than 90% human peripheral T lymphocytes and thymocytes, while it is unreacting with B cells, monocytes, granulocytes and platelets. All mitogen concentrations were chosen after appropriate titration experiments to induce a maximum proliferative response [Wang, CY, et al. (1983) (submitted for publication)].

Mononuclear cells of patients and controls were tested for proliferation and IL2 production using the mitogen-containing media and media only as control. Proliferation was measured by [$^3$H]thymidine incorporation as previously described above (Welte, K, et al. (1982) J. Exp. Med. 156:454-465), both in the absence and in the presence of highly purified exogenous IL2 (10 U/ml final concentration).

IL2 Purification and Assay for IL2 Activity. We used highly purified IL2, prepared as previously described above [Welte, K, et al. (1982) Supra]. This IL2 preparation is 37,000-fold enriched from lymphocyte conditioned medium, shows a specific activity of $10^6$ U/mg of protein, and consists of two active bands on a silver-stained sodium dodecyl sulfate-polyacrylamide gel [Welte, K, et al. (1982) Supra].

The IL2 assay was used as described before [Venuta, S, et al. (1982), UCLA Symposia in Molecular and Cellular Biology Supra; Gillis, S, et al. (1977) Nature (London) 268:154-156; Gillis, S, et al. (1978) J. Immunol. 120:2027-2031] using murine CTLL cells grown in the presence of $log_2$ dilutions of putative IL2-containing media. The IL2 concentration in each sample was calculated by probit analysis using a standard containing 2 U of rat IL2 [Gillis, S, et al. (1978) Supra]. One unit of IL2 was defined as the quantity of IL2 released in a 48-hr culture medium conditioned by rat spleen cells ($1 \times 10^6$/ml) stimulated by concanavalin A [5 micrograms/ml [Gillis, S, et al. (1978), Supra)]]. Statistical analysis of the data presented was performed using the nonparametric Kruskal-Wallis test [Kruskal, WH, et al., J. Am. Stat. Assoc. 48:583 (1952); 48:907 (1953)], Spearman rank-correlation coefficient [Siegel, S, (1956), Nonparametric statistics for the Behavioral Sciences HF Harlow (ed) New York, McGraw-Hill pp. 202-213], and Kaplan-Meyer calculations (Peto, R, et al. (1977) Br. J. Cancer 35:1-39).

TABLE IX

| | | Viral Studies Cell Surface Markers, and Survival[a] | | | | | | |
|---|---|---|---|---|---|---|---|---|
| Diagnosis | Age (years) | Herpes group titers | ERFC[b] | OKT3 | OKT4 | OKT8 | OKT4/OKT8 | Survival[c] |
| | | a | | | | | | |
| Kaposi's sarcoma | | | | | | | | |
| 1 LW | 38 | CMV[d]: CF: anticomplementary | 78.0 | 40.2 | 11.1 | 24.9 | 0.44 | 6+ |
| 2 CM | 43 | CMV: IgG: 1/1024 EBV[e]: 1/320 | 77.5 | 49.6 | 15.4 | 26.1 | 0.59 | 6+ |
| 3 AB | 38 | CMV: CF: 1/64 | 55.0 | 30.3 | 12.1 | 31.6 | 0.38 | 4 |

TABLE IX-continued

Viral Studies Cell Surface Markers, and Survival[a]

| Diagnosis | Age (years) | Herpes group titers | ERFC[b] | OKT3 | OKT4 | OKT8 | OKT4/OKT8 | Survival[c] |
|---|---|---|---|---|---|---|---|---|
| 4 JS | 34 | IgG: 1/256<br>EMV: 1/640<br>CMV: CF: 1/128 | 33.0 | 40.5[f] | 22.6[f] | 13.4[f] | 1.82 | 1 |
| 5 JP | 36 | IgG: >1/1024<br>EBV:1/1640<br>CMV: CF: 1/64 | ND | 84.0[f] | 33.8[f] | 49.1[f] | 0.68 | 6.5+ |
| 6 DV | 49 | EBV: 1/2650<br>CMV: CF: 1/64 | 81.0 | 17.9 | 33.6 | 36.5 | 0.92 | 5+ |
| 7 RS | 36 | IgG: >1/1024<br>EBV: 1/320<br>CMV: CF: 1/32 | 81.0 | 40.3 | 33.3 | 15.6 | 2.13 | 6+ |
| 8 GR | 35 | IgG: 1/128<br>EBV: 1/5128<br>CMV: CF: 1/32 | 53.0 | 39.9 | 6.5 | 26.8 | 0.24 | 3+ |
| 9 KH | 46 | IgG: >1/1024<br>EBV: 1/2540<br>CMV: CF: 1/32 | 78.0 | 29.5 | 39.3 | 32.9 | 1.19 | 2+ |
| 10 EF | 44 | EBV: 1/640<br>EBV: 1/40960 | ND | 55.1 | 27.4 | 38.4 | 0.71 | 2+ |
| 11 JP | 48 | CMV: CF: 1/256<br>IgG: >1/1024 | 77.5 | 35.2 | 47.3 | 50.2 | 0.94 | 1 |
| 12 MM | 36 | CMV: CF: 1/128<br>IgG: 1/1024 | 62.5 | 24.5 | 13.6 | 17.2 | 0.79 | 2+ |
| Opportunistic infections[g] | | | | | | | | |
| 1 JC | 24 | CMV: CF: 1/16<br>EBV: 1/640 | ND | ND | ND | ND | — | 1 |
| 2 JS | 35 | CMV: CF: 1/64<br>EBV: 1/320 | 72.0 | 26.0 | 30.0 | 61.0 | 0.49 | 1 |
| 3 HC | 37 | CMV: CF: 1/128<br>EBV: 1/1280 | 77.0 | 36.6 | 6.6 | 38.9 | 0.17 | 2+ |
| 4 JS | 40 | CMV: IgG: 1/1204<br>EBV: 1/320 | ND | 35.8 | 8.9 | 31.3 | 0.28 | 2+ |
| 5 GL | 24 | CMV: IgG: 1/1024<br>EBV: 1/320 | 83.0 | 20.5 | 14.6 | 25.2 | .0.58 | 5+ |
| Reactive lymphadenopathy | | | | | | | | |
| 1 Cl | 37 | CMV: CF: 1/64<br>EBV: 1/2560 | ND | ND | ND | 0 | — | 15+ |
| 2 CJ | 40 | CMV: IgG: 1/512<br>EBV: 1/1280 | 58.0 | 42.0[f] | 11.7[f] | 30.0[f] | 0.39 | 2+ |
| 3 JG | 42 | CMV: IgG: 1/512<br>EBV: 1/320 | 75.5 | 20.4 | 11.4 | 7.3 | 1.59 | 2+ |
| 4 JP | 27 | CMV: CF: 1/32<br>EBV: 1/2360 | ND | ND | ND | ND | — | 6+ |

[a]Normal values for laboratory: ERFC, 80 ± 8%; OKT3, 67.7 ± 10.4; OKT4, 45.2 ± 8.6; OKT8, 24.8 ± 4.2; OKT4/OKT8 ratio, 1.83 ± 0.27.
[b]ERFC, sheep erythrocyte rosette-forming cells.
[c]Survival measured from the time of assay, (+) ongoing survival.
[d]CMV, cytomegalovirus, CMV IgG, determined by ELISA.
[e]EBV, Ebstein-Barr virus; EBV antibody titers measrued by indirect fluorescence (against viral capsid antigen).
[f]Leu series of monoclonal antibodies used.
[g]Opportunistic infections present in this group: with Pneumocystis carinil, CMV, ulcerative herpes simplex, Candida.

T-Cell Mitogen-Stimulated Proliferation

The proliferation of peripheral blood mononuclear cells stimulated by PHA, OKT3, or Pan T2 was measured on day 3 or incubation, since maximal proliferation was always noted to peak on this day, with patients and controls showing the same kinetics. The kinetics of IL2 production showed maximum levels of IL2 at 15-16 hr from the initiation of cultures in both patients and controls. Tables X and Table XI show the proliferative response of the stimulated cells in the absence and presence of exogenous hp IL2. All patients with KS and opportunistic infections had significantly lower mitogen-stimulated DNA synthesis as compared to the controls, irrespective of the mitogen used (P less than 0.01). The patients with lymphadenopathy exhibited significantly lower responses only in the OKT3 assay as compared to the normals (P=0.009). All but two patients (No. 9 with KS and No. 4 with lymphadenopathy) exhibited a very low proliferative response to OKT3 (maximum cpm, less than 30,000). It is also noted that nine patients (five with KS and four with opportunistic infections) had a very low proliferative response to PHA (maximum cpm, less than 18,000). This markedly reduced proliferative response was paralleled by a consistently low response in the Pan T2-stimulated cultures of eight (four with KS and four with opportunistic infections) of those nine patients who failed to respond to PHA (maximum cpm, less than 4000). The other patients with intermediate proliferation in response to PHA also showed higher proliferation in the Pan T2 assay. There were no significant differences among the patient groups (KS versus the lymphadenopathy or opportunistic infection group, lymphadenopathy versus the opportunistic infection group) with respect to radioactive thymidine incorporation in any of the mitogen-stimulated PBL proliferation of patients with lymphadenopathy was significantly higher than that of patients with opportunistic infections (P=0.027). In two KS patients (Nos. 1 and 3) we repeated the assays after 4.5 and 4 months, respectively. PBL of patient No. 1, who had progressive disease, incorporated 9500 cpm in response to PHA the second time versus 54,800 cpm in the first study, 6500 cpm versus 18,000 cpm in the OKT3 assay, and 2000 cpm versus 38,000 cpm in the Pan T2 assay. Patient No. 3, in whom the repeated assay was run 48 hr prior to his death, showed no significant response to any of the three mitogen studies, while he had shown a low but definite mitogen response when tested the first time with 1600 cpm in the PHA proliferation, 3500 cpm in the OKT3 proliferation, and 2400 cpm in the Pan T2 proliferation. Although the longest follow-up time from the performance of assays did not exceed 6.5 months, the level of OKT3-induced proliferation correlated with patients' survival (Kaplan-Meyer calculations). All 10 patients with OKT3-induced proliferation greater than 13,000 cpm were alive at last follow-up (range 1+ to 6.5+ months), whereas 5 of 11 patients with OKT3-induced proliferation less than 13,000 cpm had died (P=0.015) (Table XI).

TABLE X

Mitogen Induced Proliferation as Measured by [$^3$H]Thymidine Uptake (cpm × $10^3$) With And Without the Addition of Purified IL2$^a$

| Diagnosis | PHA (cpm × $10^3$) −IL2 | PHA (cpm × $10^3$) +IL2 | OKT3 (cpm × $10^3$) −IL2 | OKT3 (cpm × $10^3$) +IL2 | Pan T2 (cpm × $10^3$) −IL2 | Pan T2 (cpm × $10^3$) +IL2 |
|---|---|---|---|---|---|---|
| Kaposi's sarcoma | | | | | | |
| 1. LW | 54.8 | 55.6 | 18.0 | 43.5 | 38.0* | 71.5 |
| 2. CM | 7.9 | 21.8 | 11.0 | 46.4$^c$ | 0.5 | 17.5 |
| 3. AB | 1.6 | 14.5 | 3.5 | 14.6 | 2.4 | 17.6 |
| 4. JS | 6.6 | 50.6 | 12.8 | 37.2 | 13.7 | 68.7$^c$ |
| 5. JP | 72.2* | 108.5 | 19.3 | 50.7$^c$ | 50.7* | 82.0 |
| 6. DV | 13.2 | 21.0 | 10.3 | 27.2 | 0.8 | 9.9 |
| 7. RS | 56.4 | 69.5 | 29.1 | 80.3$^c$ | 35.0* | 78.1 |
| 8. GR | 17.4 | 26.4 | 12.9 | 16.9 | 19.2 | 17.5$^n$ |
| 9. KH | 29.7 | 28.0$^n$ | 31.6 | 50.1$^c$ | 17.3 | 44.4$^c$ |
| 10. EF | 25.2 | 27.6$^n$ | 15.9 | 41.2 | 18.1 | 46.9$^c$ |
| 11. JP | 20.5 | 22.6$^n$ | 12.7 | 31.3 | 5.7 | 23.7 |
| 12. MM | 54.3 | 54.3 | 7.2 | 13.0 | 0.6 | 0.7$^n$ |
| Opportunistic infections | | | | | | |
| 1. JC | 28.9 | 28.7$^n$ | 11.4 | 25.2 | 0.3 | 1.4$^n$ |
| 2. JS | 3.1 | 3.3$^n$ | 3.2 | 1.7$^n$ | 3.5 | 6.3 |
| 3. HC | 10.3 | 24.5 | 8.4 | 22.0 | 18.7 | 37.7$^c$ |
| 4. JS | 16.0 | 26.0 | 14.7 | 33.3 | 0.4 | 0.9$^n$ |
| 5. GL | 11.4 | 25.7 | 14.4 | 30.1 | 1.5 | 4.9 |
| Reactive lymphadenopathy | | | | | | |
| 1. CL | 41.7 | 44.3 | 13.1 | 26.7 | 20.4 | 32.3$^c$ |
| 2. CJ | 55.0 | 53.0 | 27.8 | 42.0 | 19.4 | 36.5$^c$ |
| 3. JG | 26.0 | 29.4 | 12.7 | 25.9 | 0.5 | 1.4$^n$ |
| 4. JP | 108.6* | 137.0 | 48.2* | 86.2 | 72.6* | 112.5 |
| Heterosexual controls [median (range)] | | | | | | |
| N = 10 | 78.9 (56.5–110.9) | 93.3 (59.1–125.0) | 66.1 (46.3–88.3) | 84.0 (55.9–127.0) | 60.2 (27.6–88.0) | 91.2 (41.0–126.0) |

$^a$*cpm within normal range before the addition of IL2 (The values for patients 1, 7 and 12 with Kaposi's sarcoma and 2 with lymphadenopathy in the PHA assay without purified IL2 considered biologically normal.) With the addition of IL2: $^c$complete correction; $^n$no response.

TABLE XI

IL2 Production by PBL in Response to Stimulation with PHA, OKT3, and Pan T2

| Diagnosis | N$^a$ | PHA | OKT3 | Pan T2 |
|---|---|---|---|---|
| | | IL2 (U/ml); median (range)] | | |
| Kaposi's sarcoma | 12 | 1.1(<0.1–4.2) | 0.9(0.2–1.8) | 0.3(<0.1–1.3) |
| P value$^b$ | | 0.020 | 0.002 | 0.024 |
| Opportunistic infections | 5 | 0.2(<0.1–0.9) | 0.2(<0.1–1.4) | 0.1(<0.1–0.7) |
| P value | | 0.006 | 0.006 | 0.050 |
| Reactive lymphadenopathy | 4 | 1.1(0.6–1.6) | 0.6(0.5–9.6) | 0.2(<0.1–0.6) |
| P value | | >0.05 | >0.05 | 0.030 |
| Heterosexual controls | 10 | 2.3(0.8–6.8) | 3.5(0.9–16) | 0.7(0.4–2.4) |

$^a$N number of patients
$^b$P value based on the Kruskal-Wallis test comparing patient groups with controls in each mitogen-induced assay.

TABLE XII

Simulation of the Proliferative Response of PBL to PHA, OKT3, and Pan T2 by the Addition of IL2

| Diagnosis | N$^a$ | PHA | OKT3 | Pan T2 |
|---|---|---|---|---|
| | | [cmp(+IL2)/cmp(−IL2)$^b$; median (range)] | | |
| Kaposi's sarcoma | 12 | 1.4(0.9–9.1) | 2.6(1.3–4.2) P = 0.000* | 2.6(0.9–35.7) |
| Opportunistic infections | 5 | 1.6(1.0–2.4) | 2.2(0.9–2.1) | 2.0(1.8–3.8) |
| Reactive lymphadenopathy | 4 | 1.1(0.9–1.3) | 1.9(1.5–2.0) P = 0.006* | 1.7(1.5–2.7) |

TABLE XII-continued

Simulation of the Proliferative Response of PBL to PHA, OKT3, and Pan T2 by the Addition of IL2

| Diagnosis | N[a] | PHA | OKT3 | Pan T2 |
|---|---|---|---|---|
| | | [cmp(+IL2)/cmp(−IL2)[b]; median (range)] | | |
| Heterosexual controls | 10 | 1.1(0.9−1.4) | 1.3(1.1−1−5) | 1.6(1.1−2.9) |

[a]N number of patients
[b]cpm(+IL2)/cpm(−IL2) = [$^3$H]thymidine incorporation in the presence of added IL2 divided by [$^3$H]thymidine incorporation without the addition of IL2.
*Ratio of cpm(+IL2)/cpm(−IL2) significantly higher than in controls using the Kruskal-Wallis test. All other IL2-induced increments of T-cell proliferation were not significant at the 0.05 level compared to controls.

The OKT4+/OKT8+ Ratio

The patient group had significantly lower OKT4+/OKT8+ ratios compared to controls (P=0.030), with a median ratio of 0.79 versus 1.88 for controls. There was no significant difference with respect to OKT4+/OKT8+ ratio among patient groups (KS versus the lymphadenopathy or opportunistic infection group, lymphadenopathy versus the opportunistic infection group). There was no correlation between the level of proliferation induced with any of the mitogens used and the OKT4+/OKT8+ ratio, as well as no correlation between patients' survival and this ratio (P greater than 0.05).

Endogenous IL2 Production

Patients with KS and opportunistic infections produced significantly lower amounts of IL2 than normal controls irrespective of the mitogen used (Table XIV). The median IL2 production in the OKT3-stimulated cultures was 0.9 U/ml for KS patients and 0.2 U/ml for patients with opportunistic infections, compared to 3.5 U/ml for normal controls. Patients with lymphadenopathy produced significantly lower amounts of IL2 only in the Pan T2-stimulated cultures, while IL2 production was not significantly lowered in this patient group when OKT3 or PHA was used as mitogen (P greater than 0.5). The amount of IL2 produced by cultured PBL correlated significantly with the level of proliferation (absolute cpm) in all mitogen-stimulated assays for both patients and controls (P less than 0.01) using the Spearman rank-correlation coefficient).

TABLE XIII

OKT3 AND PHA INDUCED IL2 PRODUCTION OF PBMC FROM PATIENTS AFTER BMT

| Diagnosis | n | OKT3 (1.25 ng/ml) IL2 (U/ml) median (range) | PHA (0.5%, v/v) IL2 (U/ml) median (range) |
|---|---|---|---|
| Leukemia (ALL, AML, CML) | 12 | <0.2 (<0.2−1.5) | <0.2 (<0.2−1.0) |
| Aplastic anemia | 6 | 0.25 (<0.2 −1.0) | <0.2 (all < 0.2) |
| Severe combined immunodeficiency | 2 | <0.2 (both < 0.2) | <0.2 (both < 0.2) |
| Autologous BMT (NHL, neuroblastoma) | 3 | <0.2 (all < 0.2) | <0.2 (all < 0.2) |
| Controls | | | |
| (a) normal | 21 | 3.5 (0.9−16) | 2.3 (0.8−6.8) |
| (b) prior BMT* | 8 | 1.5 (0.4−2.5) | 1.0 (0.7−1.6) |

*patients prior to BMT (all diagnostic subgroups)

Effect of Highly Purified IL2 on Mitogen-Induced Proliferation

The addition of hp IL2 in the absence of mitogenic stimulation did not have any effect on the proliferation of PBL from patients or controls. In the KS group, hp IL2 brought the level of thymidine incorporation within the normal range of patients 2, 5, 7, and 9 with OKT3 as mitogen and normalized the proliferation for patients 4, 9, and 10 with Pan T2 as mitogen. hp IL2 with Pan T2 as mitogen also normalized the proliferation of patients 1 and 2 in the lymphadenopathy group and of patient 3 in the opportunistic infection group (Table XIII). hp IL2 was unable to induce complete correction for any patient in the PHA-stimulated assay.

In several patients there was no significant correction of proliferation (less than 25% increment) with the addition of hp IL2 (Table XI). These nonresponder patients in the PHA assay were three patients with KS (Nos. 9, 10, and 11) and two patients with opportunistic infections (Nos. 1 and 2); in the OKT3 assay, only one patient (No. 2) with opportunistic infection; and in the Pan T2 assay, two patients with KS (Nos. 8 and 12), one patient with lymphadenopathy (No. 3), and two patients with opportunistic infections (Nos. 1 and 4) (Table XI). The median increase in [$^3$H]thymydine incorporation after the addition of IL2 was 1.4-, 1.1-, and 1.6-fold, respectively, for KS, lymphadenopathy, and opportunistic infection patients in PHA-stimulated culture; 2.6-, 1.9-, and 2.20fold, respectively, after OKT3 stimulation, and 2.6-, 1.7-, and 2.0-fold, respectively, in the Pan T2-stimulated cultures. Patients with KS and lymphadenopathy, compared to controls, showed significantly higher increments of T-cell proliferation in response to exogeneous IL2 when OKT3 was used as mitogen (P less than 0.01 Table XIII).

IL is a potent regulator of T cell proliferation, acting as an antigen nonspecific, genetically unrestricted mediator [Watson, J, et al. (1980), Immunol. Rev. 51:257−278; Smith, KA, (1980), Immunol. Rev. 51:337−357]. Previously, the OKT4+ helper subset of T cells was thought to be solely responsible for the synthesis of IL2 upon appropriate antigen or mitogen stimulation and interaction with macrophages and their products (Palacios, R, et al. (1981), Cell Immunol. 63:143−153). Recent data proved, however, that IL2 can be secreted by OKT8+ lymphocytes as well [Meuer, SC, et al., (1982) J. Immunol. 129:1076−1079; Luger, TA, et al. (1982), J. Clin. Invest. 70:470−473]. Antigens or mitogens such as PHA or the monoclonal antibodies OKT3 and Pan T2 are required to activate IL2 responder T cells to express the IL2 receptor, which appears essential for IL2 binding and subsequent triggering of T-cell proliferation [Ruscetti, FW, et al. (1981), Blood 57:379−394; Smith, KA, (1980), Immunol. Rev. 51:337−357; Palacios, R, et al. (1981), Cell Immunol. 63:143−153].

In the present study we have investigated the ability of PBL from homosexual patients with KS, lymphadenopathy, and opportunistic infections to generate IL2 and to proliferate upon stimulation in vitro with PHA and two mitogenic monoclonal antibodies, as well as the effect of exogenous highly purified IL2 on the proliferative response induced by these mitogens. We studied IL2 production and response in these homosexuals with KS and opportunistic infections since this patients population has been shown to have a rather unique immunodeficiency syndrome [Siegal, FP, et al. (1981) Supra; Gottlieb, MS, et al. (1981) Supra; Koziner, B, et al. (1982), N. Engl. J. Med. 306:933–934] of unknown etiology and pathogenesis, and no treatment has so far been able to restore their immune functions to normal either in vitro or in vivo. The homosexuals with reactive lymphadenopathy were included in the study since they might represent the first step toward the clinically manifested acquired immunodeficiency.

To our knowledge there is only one report in the medical literature dealing with the aspects of IL2 synthesis and its role in the proliferative response to PHA in patients with primary immunodeficiencies (Lopez-Botet, M, et al. (1982), J. Immunol. 128:679–683). We found that the addition of IL2-containing supernatant to cultured PBL from patients with primary immunodeficiencies caused an increase in DNA synthesis in the presence of suboptimal concentrations of PHA. The PBL of these patients with a reduced proliferative response to PHA ("hyporesponders") were shown to produce significantly lower amounts of IL2 [Lopez-Botet, M, et al. 1982 Supra]. We have described previously the ability of exogenous IL2 to increase thymidine incorporation by PBL cultures of normal controls when stimulated with PHA [Mertelsmann, R, et al. (1981) Blut 43:99–103], although this was not seen by Lopez-Botet et al. (Lopez-Botet, et al. (1982) Supra). As a source of IL2 these authors used only IL2 containing conditioned media, whereas our IL2 preparation derived from normal human lymphocytes was highly purified, nonmitogenic, and free of other lymphokine activities [without alpha—or gamma-interferon, granulocyte macrophage colony stimulating factor, T-cell replacing factor, B-cell growth factor, T-cell replacing factor, B-cell growth factor, thymocyte differentiating activities [Welte, K, et al (1982), J. Exp. Med. 156:454–464]], which might account for the discrepancy. Although the absolute increase in proliferation after the addition of hp IL2 was similar in patients and controls, the median values of IL2-induced increments were higher for each patient groups compared to the controls (median value equal to the controls only the lymphadenopathy group, PHA assay). The relative increments were statistically significantly higher at P less than 0.01 for the KS and the reactive lymphadenopathy groups in the OKT3 assay.

We have shown that PBL from all homosexual patients investigated by us, except for patient No. 4 from the lymphadenopathy group, failed to show a normal proliferative response to OKT3. This defect appears to be due to a decrease in IL2 production, since PBL from KS and patients with opportunistic infections produced only low quantities of IL2. hp IL2 in the OKT3-stimulated cultures was able to normalize the proliferation of four patients with KS and to partially restore the proliferation in another 15 deficient patients, except patient No. 2 from the opportunistic infections group. We have also studied the response of PBL from the patients to an additional mitogenic monoclonal antibody, Pan T2, isolated in this laboratory. This antibody appears to recognize a different epitope of the same molecular complex recognized by OKT3, which appears to play an important role in T-cell activation (Wang, CY, et al. (1983) (submitted for publication). In the presence of Pan T2, the addition of IL2 normalized the proliferative response in six patients and partially corrected the response in another six patients. The Pan T2-induced proliferation was onto correctable with IL2 in five patients. Pan T2 proved to be the most sensitive of the three mitogens in detecting an IL2 production abnormality, since using Pan T2, we observed significantly lower amounts of IL2 even in the lymphadenopathy group. The results indicate that all groups of patients have a defect in IL2 production. The defect does not appear to be at the level of the IL2 receptor, since all mitogens tested were able to induce a proliferative response in the presence of exogenous IL2. The difference between the IL2 responder cells in normal heterosexual controls and those in homosexual patients appears thus to be more of a quantitative than a qualitative nature and possibly related to the different absolute counts of OKT4+ and OKT8+ subsets.

Our data are consistent with the previously reported decreased T-helper subpopulation (OKT4+) in these patients [Gottlieb, MS, et al. (1981), Supra; Koziner, B, et al. (1982) Supra]. The decreased OKT4+/OKT8+ ratio (helper/suppressor) previously reported (Koziner, B, et al. (1982) Supra) and also found in our patient population suggests either that the production of IL2 by OKT8+ T cells in homosexuals is less than that of OKT4+ cells or, alternatively, that the OKT8+ subset might absorb and required higher concentrations of IL2 for the induction of proliferation than OKT4+ cells. In healthy blood donors similar concentrations of IL2 were found in supernatants from mitogen-stimulated cultures of highly enriched OKT4+ or OKT8+ cells [Meuer, SC, et al. (1982) J. Immunol. 129:1076–1079].

Kornfeld et al. recently reported a significantly lower OKT4+/OKT8+ ratio in symptomatic homosexuals (lymphadenopathy and/or opportunistic infections) compared to asymptomatic homosexuals [Kornfeld, H, et al. (1982) N. Engl. J. Med. 307:729–731]. We were unable to find a correlation between OKT4+/OKT+ ratio and PBL proliferative ability or IL2 production under mitogen stimulation.

It may be only homosexual patients with inverted OKT4+/OKT8+ ratios are deficient in IL2 production; other pathological entities associated with inverted helper/suppressor ratio may well show the same IL2 production defect. Since advanced age has previously been shown to be associated with decreased IL2 production [Gillis, S, et al. (1981) J. Clin. Invest. 67:937–042], the classic KS seen in the older population may also be related to a similar immune defect, as seen in the young homosexual males. It will be of interest to observe the further course of the disease(s) in the "healthy" homosexuals with lymphadenopathy, since this group appears to have immune alteration as evidence by a lower response in the OKT3-stimulated cultures.

Follow-up assays in the same patients seem to have a prognostic value, as suggested by the two patients who had repeated determinations of their PBL proliferative capacity.

The level of OKT3-induced proliferation may also be of prognostic significance (P=0.015), as suggested by our data, but longer follow-up is necessary to document the validity of this observation. It is of interest to note that of the five patients that died within the 6.5-month follow-up, three were nonresponders in at least one of the IL2-supplemented mitogen assays.

Our data indicate that the proliferation defect can be corrected at least partially by the addition of IL2. However, the patients' T cells do not spontaneously express receptors for IL2 since they need to be primed with a mitogen before they become responsive to IL2.

The in vivo administration of IL2 may be beneficial for homosexual patients with and without KS who are severely immunocompromised. Whether IL2 receptor activation by the simultaneous administraton of mitogenic monoclonal antibodies is required for the restoration of the immune response in vivo remains to be determined. A phase I trial of IL2 in this patient population has been initiated.

Phase I/Phase II Clinical Trial: As of 5/1/83 a total of twelve patients have received hp IL2 as part of the phase I/phase II trial of hpIL2. The mode of administration, dosage schedules and monitoring are detailed above. So far a dose level of 20,000 U/m$^2$ daily for 14 days has been reached. We have not seen any evidence of toxicity either by clinical evaluation or by monitoring laboratory studies. Furthermore, preliminary evidence suggests biological activity of hpIL2 in man in vivo, with improvement of some of the marker studies while on hpIL2. Preliminary evidence for efficacy was also seen with an apparent effect of IL2 on disease related symptoms, e.g., reduction of fever in patients with AIDS. Although the evidence for biological activity and clinical efficacy is very preliminary at this point, we are encourage by the absence of side-effects of hpIL2 and the first indications of an in vivo effect in man. The current trial will be continued until either toxicity is reached or a dose level resulting in definite and reproducible biological activity can be established. Murine studies investigating different dose levels and schedules in transplanted and autochthonous tumor models will be performed in parallel with the ongoing phase I trial.

Use of hp IL2 in transplantation disorders

Using OKT3 monoclonal antibody as a mitogen, we have studied Interleukin 2 (IL2) production and proliferation in peripheral blood mononuclear cells (PBMC) of 23 patients receiving bone marrow transplants. Twenty patients were recipients of allogeneic bone marrow for treatment of hematological malignancies, a plastic anemias (AA) or severe combined immunodeficiencies (SCID). Three patients with Hodgkin's disease or neuroblastoma received autologous bone marrow. Endogeneous IL2 production was not detectable (less than 0.2 U/ml) in PBMC of 18 patients and was very low in PBMC from 5 patients (0.5–1.5 U/ml) as compared to normal controls (median 3.5 U/ml) or pretransplant patients (median: 1.5 U/ml). The low IL2 production was associated with defective OKT3 induced proliferation of PBMC in 19 of 23 patients studied. In the first 6 months after BMT, 14 of 15 patients (93%) showed defective proliferation of PBMC as compared to 5 of 8 patients (63%) tested between 7 and 18 months after BMT (p less than 0.1). In all but three patients, addition of highly purified human lymphocyte IL2 (hp IL2) restored OKT3 induced proliferation of PBMC to within the normal range. This study demonstrates that PBMC in patients after BMT have a defect of IL2 production but are able to express IL2 receptors in response to OKT3 antibody and to proliferate normally upon addition of hpIL2. PBMC of all patients showed similar functional defects whether or not they received additional therapy, including various conditioning regimens prior to BMT and immunosuppressive therapy after BMT. These observations suggest that T cell defects after BMT are most likely secondary to quantitative or qualitative defects of transplanted T lymphocytes or their precursors.

During the first two years after transplantation recipients of allogeneic marrow transplants demonstrate a severe deficiency of cellular and humoral immunity [Noel, DR., et al. (1978) Blood 51:1087; deBruin, HG, et al. (1981) J. Immunol. 127:244; Witherspoon, RP, et al. (1982) Blood 59:844; Friedrich, W, et al. (1982) Blood 59:696; Fox, R., et al. (1982) Blood 60:578; Donnenberg, AD, et al. (1982) J. Immunol. 129:1080; Schroff, RW, et al. (1982) J. Immunol. 129:1926; Mori, T., et al. (1983) J. Immunol. 130:712]. This immunodeficiency leads to increase susceptibility to frequently letal bacterial, fungal, and viral infections.

Interleukin 2 (IL2) is one of the major cytokines responsible for clonal expansion of T cells [Ruscetti, FW, et al. (1981) Blood 57:379] and human natural killer (NK) cells [Domzig, W, et al. (1983) J. Immunol. 130:1970; Flomenberg, N, et al. (1983) J. Immunol. 130:2635] as well as for the activation of cytotoxic effector cells [Domzig, W., et al. Supra (1983); Merluzzi, VJ, et al. (1983) J. Immunol. 131:806]. The role of IL2 in several immunodeficiency states [Welte, K, et al. (1983) in "Modern Trends in Human Leukemia V" Springer Verlag, Berlin-New York pp. 369; Ciobanu, N, et al. (1983) J. Clin. Immunology 3:332; Flomenberg, N, et al. (1983) J. Immunol. 130:2644] as well as in certain lymphoid leukemias [Gootenberg, JE, et al. (1981) J. Exp. Med. 154:1403; Venuta, S, et al. (1983) Blood 61:781] has been previously documented. Defective IL2 production could be one possible mechanism for the abnormal immune function in patients after bone marrow transplantation (BMT) [Donnenberg, AD, et al. (1982) J. Immunol. 129:1080; Mori, T, et al. (1983) J. Immunol. 130:712].

Recently, OKT3, a monoclonal antibody against a T-cell surface antigen has been shown to be mitogenic even in nanogram concentrations [Van Wauwe, JP, (1980) J. Immunol. 124:2708; Chang, TW, et al. (1981) Proc. Nat'l. Acad. Sci. USA 78:1805] and to induce IL2 production in total T cells as well as in T cell subsets [Welte, K, et al. (1983) J. Immunol. 131:2356]. OKT3 appears to recognize an epitope of the antigen-recognition complex on T-lymphocytes [Chang, TW, et al. (1981) Proc. Nat'l. Acad. Sci. USA 78:1805; Reinherz, EL, et al. (1982) Cell 30:735] triggering mitogenesis in a way similar to that induced by antigen.

We studied IL2 production and response of peripheral blood mononuclear cells (PBMC) from patients up to 18 months after BMT using OKT3 antibody as mitogen and, as control, phytohemagglutinin (PHA). In addition we investigated whether highly purified human lymphocyte IL2 (hpIL2) [Welte, K, et al. (1982) J. Exp. Med. 156:454] was capable of restoring defective proliferative responses of T cells in vitro.

Patients: The study group consisted of 20 recipients of an allogeneic BMT: 4 patients with acute myelogenous leukemia (AML) in first or second remission, 4 patients with acute lymphoblastic leukemia (ALL) in second or third remission, 4 patients with chronic myelogeneous leukemia (CML), 6 patients with aplastic anemia (AA), and 2 patients with severe combined immunodeficiency (SCID). In addition 3 recipients of autologous BMT were studied: 1 patient with neuroblastoma and 2 patients with Non-Hodgkin's lymphoma (NHL). Details of the transplantation procedure have been described [Friedrich, W, et al. (1982) Blood 59:696]. Patients with AML, ALL and CML were conditioned for transplantation with cyclophosphamide (60 mg/kg for 2 days) and hyperfractionated total body irradiation (TBI, total dose 1320 rads). In the aplastic anemia group, 4 patients received only preparative chemotherapy with cyclophosphamide (50 mg/kg for 4 days), cytosine arabinoside (200 mg/kg/day for 5 days) and 6-thioguanine (200 mg/kg/day for 5 days), whereas 2 other patients were conditioned similar to patients with leukemias but with less TBI (800,300 rads, respectively). SCID patients received nb cytoreductive treatment. The patient with neuroblastoma was treated with L-phenylalanine mustard (L-PAM) 240 mg/m$^2$ plus dihydroglactitol 240 mg/m$^2$ and low TBI, while the two patients with NHL received the same regimen used for the patients with leukemias. All patients receiving an allogeneic BMT except one, received the marrow from HLA-A,B,C, and D identical siblings and engrafted permanently following the first attempt. One patient with SCID engrafted permanently only after the fourth attempt, when receiving a lectin separated marrow from his haploidentical mother. Post-transplant immune suppression for all patients receiving allogeneic BMT consisted of methotrexate 15 mg/m$^2$ on day 1, followed by 10 mg/m$^2$ on days 3,6,13,20 and weekly thereafter to day 100. All immune suppressive drugs were stopped at that time. Patients with graft- versus-host disease (GvHD) of at least grade 2 were treated with high dose prednisone (2 mg/kg/d). One AML patient received prednisone plus cyclosporine A (10 mg/kg/d) while another ALL patient was maintained only on azathioprine (50 mg/d). At the time of the IL2 analysis, 13 patients had GvHD (4 patients grade 1;3 patients grade 2; and 6 patients grade 3). Four of the 13 patients had acute GvHD.

Proliferation Assay: Mononuclear cells (PBMC) from 10–20 ml of heparinized blood were separated by density gradient centrifugation on Ficoll-Hypaque as previously described (Welte, K, et al. (1983) J. Immunol. 131:2356) and resuspended at a final concentration of 10$^6$ cells/ml in RPMI 1640 supplemented with 10% heat-inactivated FCS, glutamine (2 mM), Penicillin (50 U/ml), and Streptomycin (50 microg/ml). Each sample was stimulated in triplicate microwell cultures (#3596 culture plate, Costar Inc. Cambridge, MA) in the presence or absence of mitogen (PHA, OKT3), and in the presence or absence of hpIL2 [Welte, K, et al. (1982) J. Exp. Med. 156:454]. Unless stated otherwise the concentrations used were 1.25 ng/ml for OKT3 Ortho Pharmaceuticals, Raritan, NJ) and 0.5% (v/v) for PHA (PHA-M, Grand Island Biological Co.). After 24 hours, 100 microl supernatant were removed from each well to be assayed for IL2 activity. Identical cultures were incubated for 3 days and then pulsed for 4 hrs. with $^3$H-thymidine (0.5 micro Ci/well; New England Nuclear, Boston, MA) and the $^3$H-thymidine uptake measured as described previously [Welte, K, et al. (1983) Springer Verlag, Berlin-New York pp. 369 Supra; Welte, K, et al. (1983) J. Immunol. 131:2356]. Maximum IL2 production was seen at 24 hours while maximum proliferation was seen after 3 days. Interleukin 1 (IL1) was purchased from Genzyme, Co. (Norwalk, Connecticut) and its effect on IL2 production and lymphocyte proliferation was tested in PBMC cultures from two patients. Statistical evaluation was performed using the Kruskal-Wallis test (two-side p values).

For the IL2 assay, IL2 dependent cultures of cytotoxic T lymphocytes were used as previously described above. (Welte, K, et al. J. Exp. Med. Supra)

IL2 Production: Table XIV details the IL2 production data of the patient population. PBMC from 18 patients after BMT did not produce detectable amounts of IL2 (less than 0.2 units per ml). PBMC from 5 patients produced between 0.5 and 1.5 U/ml IL2 as compared to a median of 3.5 U/ml IL2 in controls (n=21) (p less than 0.001), when stimulated with OKT3 antibody. IL2 production was not significantly different between the different diagnostic subgroups (p less than 0.1). PBMC from 8 patients (all diagnostic subgroups), analyzed prior to BMT, produced IL2 in the low normal range (Table XIV).

Proliferative Response to OKT3 Antibody and PHA: As shown in FIG. 10–12, low IL2 production was followed by a low proliferative response of PBMC, as measured by $^3$H-thymidine incorporation on day 3. PBMC from 9 of the 12 patients with leukemias, 5 of 6 patients with AA, both SCID patients, and the 3 patients after autologous BMT had defective mitogen responses to OKT3 (FIG. 10) as compared to normal controls (n=21). The PBMC from 8 patients (all diagnostic subgroups) tested prior to BMT showed a wide range of proliferative responses to OKT3 antibody (median: 38,000 cpm, range 15,000–88,000 cpm), and to PHA (median: 71,000, range 17,000–165,000 cpm), respectively. These responses were significantly higher than those seen after BMT (p less than 0.05). Whereas the median proliferative response of PBMC from patients after BMT in the absence of IL2 was similar for OKT3 and PHA as mitogens, the median $^3$H-thymidine incorporation in the presence of hp IL2 was much higher, when OKT3 (median 50,500 cpm) rather than when PHA was used as mitogen (median 24,500 cpm) FIG. 11. In all except 3 patients, proliferation of PBMC could be restored to within the normal range by hpIL2, (FIG. 10–12) when OKT3 was used as mitogen. The enhancement of proliferation by addition of hpIL2 (10 U/ml) to OKT3 or PHA stimulated PBMC was significantly higher in patients (OKT3: median 6.8 fold; PHA: 3.4 fold) than in normal controls (OKT3: median 1.34 fold; PHA: 1.13 fold) (p less than 0.001). However, this enhancement was higher for OKT3 than for PHA (p less than 0.005); comparing enhancement ratios in patients vs. normal controls). To test whether defective production of IL1 by monocytes was responsible for the low endogenous IL2 production and proliferative responses of PBMC from the BMT patients, IL1 (100 U/ml) was added to the mitogen stimulated cultures of two patients. No effect was seen, both, in the absence and presence of exogenous IL2.

Studies in controls and 6 patients after BMT with OKT4/OKT8 T cell ratios of less than 1.0 showed that the ratio of T lymphocyte subsets did not change in vitro when cultured for 3 days in the presence of OKT3 antibody and hpIL2. This finding may suggest that there was no preferential growth of one subpopulation of T cells under our experimental conditions.

The Effect of Time from BMT on Mitogen Responses to OKT3 Antibody: FIG. 12 demonstrates that a proliferative defect was present even up to 18 months after BMT. However, the median proliferation of PBMC in absence of hpIL2 was higher (12,000 cpm) in the group 7–18 months after BMT than in the group in the first 6 months after BMT (5800 cpm) (p=0.09). In the presence of hpIL2, the median $^3$H-thymidine uptake of PBMC was 79,000 cpm in the 7-18 months group and 41,000 cpm in the group less than 7 months after BMT (p=0.06).

The Effect of Conditioning Regimens on Mitogen Responses to OKT3 Antibody: IL2 production and proliferation of PBMC from patients receiving no conditioning regimen (SCID), chemotherapy alone (4 patients with AA) or receiving chemotherapy and TBI (1320 rad for patients with leukemia or receiving autologous transplant; 300 or 800 rad for two patients with AA) were compared. No differences between these groups were seen with respect to endogenous IL2 production or proliferative responses to OKT3 or PHA, respectively, in the absence or presence of exogenous hpIL2.

The Effect of GvHD and Immunosuppressive Drugs on Mitogen Responses to OKT3 Antibody: The study population consisted of three groups with respect to immunosuppressive medications given after BMT. Patients receiving autologous BMT were given no further immunosuppressive therapy after BMT. All patients receiving allogeneic BMT, were treated with prophylactic methotrexate, while those with GvHD received, in addition, high dose prednisone (see above). Only one patient received prednisone plus cyclosporine A for GvHD. No differences between groups were seen with respect to endogenous IL2 production (Table XIV) and proliferative responses to OKT3 antibody and PHA, respectively, in the absence or presence of exogenous IL2 (FIG. 10). It is interesting that PBMC from the one patient receiving cyclosporine A, showed the lowest mitogen responses of all patients tested (OKT3 response without IL2: 1,100 cpm, with exogenous hpIL2: 13,000 cpm).

The study group included 13 patients who developed acute or chronic GvHD (grade 1-3) (shown with asterisks beside the symbols in FIG. 1). There were no statistically significant differences in the mitogen responses nor in the restoration of proliferation of PBMC by hpIL2 between patients with or without GvHD.

This demonstrates, that PBMC from patients up to 18 months after BMT have defective mitogen responses which are secondary to a defect in IL2 production. This finding is specific for patients after BMT, since PBMC from patients tested prior to BMT do not exhibit this defect to the same degree. Addition of IL1 to mitogen stimulated PBMC cultures of two patients was without effect on IL2 production suggesting that defective IL1 production by monocytes is not responsible for the observed defects. Most of the patients had an imbalance in the OKT4/OKT8 (Leu 3/Leu 2) T cell ratio with a predominant OKT8+ subpopulation [deBruin HG, et al. (1981) J. Immunol. 127:244; Friedrich, W, et al. (1982) Blood 59:696; Fox, R, et al. (1982) Blood 60:578; Schroff, RW, et al. (1982) J. Immunol. 129:1926, own unpublished observations]. However, using OKT3 as mitogen both subgroups (OKT4+, OKT8+) of T lymphocytes were capable of producing IL2 (Welte, K, et al. (1983) J. Immunol. 131:2356). It is therefore unlikely that the reversed OKT4/OKT8 ratio is the reason for the IL2 production defect. In addition, we have not found any correlation between IL2 production by PBMC and OKT4/OKT8 T cell ratio in 10 patients tested. The lack of correlation between low OKT-4/OKT8 T cell ratios and OKT3 mitogen responses has recently been documented in other immunodeficiency states including patients with acquired immunodeficiency syndrome [AIDS; Welte, K, et al (1983) Springer, Verlag, Berlin-New York pp. 369 Supra; Ciobanu, N, et al. (1983) J. Clin. Immunology 3:332; Flomenberg, N, et al. (1983) J. Immunol. 130:2644).

Other factors, which could have been reasons for defective IL2 production by PBMC include: (a) the quality or quantity of transplanted T lymphocytes and their precursors, (b) the conditioning for the transplantation with alteration of the microenvironment by chemotherapy and irradiation, (c) post-transplant immunosuppression (prednisone, methotrexate), d) T cell maturation defects following the absence of a normal thymic milieu (a-d have also been proposed as possibly causing the low OKT4/OKT8 ratio; (Schroff, RW, (1982) 129:1926)), (e) a defective interaction between Ia+ monocytes/macrophages and T cells. Since similar defective OKT3 mitogen responses were seen following autologous and allogeneic BMT, it appears unlikely that histocompatibility differences or post-transplant immunosuppressive therapy were responsible for the defects. Furthermore, patients receiving (a) no conditioning regiment or (b) chemotherapy with or without TBI, showed the same defects with respect to OKT3 mitogen responses. Although several of the agents given to BMT patients have previously been shown to suppress IL2 production and response by PBL (e.g. cyclophosphamide, (Merluzzi (1983) J. Immunol. 131:806); cyclosporine A, (Hess, AD et al. (1982) J. Immunol. 128:355)), no clear relationship between administration of these drugs and defective OKT3 mitogen responses was observed. These observations would suggest that defects in T cell function following BMT were primarily due to the quality or quantity of transplanted T lymphocytes or their precursors. This hypothesis is in agreement with previous reports demonstrating relative immaturity of T lymphocytes in BMT patients [deBruin, HG, et al. (1981) J. Immunol. 127:244; Fox, R, et al. (1982) Blood 60:578; Schroff, RW, et al. (1982) J. Immunol. 129:1926].

As expected, the defective IL2 production was followed by defective proliferation of PBMC as measured by $^3$H-thymidine incorporation. In the first 6 months after BMT, PBMC from all patients but one exhibited defective mitogen responses to OKT3. In the group 7-18 months after BMT, PBMC from 3 of 8 patients showed normal proliferative responses. In the presence of hpIL2 (10 U/ml), proliferative responses of PBMC to OKT3 antibody could be restored to within the normal range in all but three patients. One of these three patients received cyclosporin A at the time of study. However, this PBMC proliferation improved from 1,100 cpm in the absence of IL2 to 13,000 cpm in the presence of IL2. PBMC from the two other patients showed normal proliferation upon addition of hpIL2 two months after the first study. Whether different kinetics of restoration of IL2 production and T cell proliferation after BMT are of prognostic value, is under investigation.

The finding that OKT3 antibody was a potent mitogen raised the possibility that OKT3 antibody was reacting with the antigen recognition complex of T cells [Chang, T. W., et al. (1981) Proc. Nat'l. Acad. Sci. USA. 78:1805; Reinherz, E. L., et al. (1982) Cell 30:735] triggering mitogenesis in a way similar to that induced by antigen. The percentage of OKT3 positive lymphocytes reaches normal values shortly after transplantation in most patients and remains normal thereafter in all patients [deBruin, HG, et al. (1981) J. Immunol. 127:244; Friedrich, W, et al. (1982) Blood 59:696; Fox, R, et al. (1982) Blood 60:678]. Possible induction of OKT3 antigen by IL2 is therefore an unlikely explanation for the IL2 responsiveness of OKT3 antibody stimulated PBMC. Furthermore, OKT3 antibody induces modulation of OKT3 antigen, which may be part of the mitogenic effect of OKT3 antibody, within a few hours (Reinherz, EL, et al. (1982) Cell 30:735; E. Rinnooy Kan, E. Platzer, K., Welte, C. Y. Wang, submitted for publication). The OKT3 antigen modulation, however, does not render cells unresponsive to IL2 (Welte, K, et al. (1983) J. Immunol. 131:2356; Reinherz, EL, et al. (1982) Cell 30:735).

The OKT3 antibody induced proliferation of PBMC was normalized in vitro in nearly all patients by hpIL2, whereas only 4 patients achieved normalization of their proliferative response of PBL upon addition of hpIL2 with PHA as mitogen. This observation would suggest that T lymphocytes in patients after BMT were able to express normal levels of IL2 receptors in response to OKT3 antibody but not to PHA. IL2 has previously been shown to be able to restore (a) impaired cell-mediated lympholysis in patients with acute GvHD but not chronic GvHD [Mori, T, et al. (1983) J. Immunol. 130:712] and (b) PHA stimulated T cell colony-formation of lymphocytes from patients early after BMT (Donnenberg, AD, et al. (1982) J. Immunol. 129:1080). Both groups hypothesized, that the defect in those patients was a functional T helper cell defect. Both reports are consistent with our observations, that T cells from patients after BMT were capable of responding to IL2.

Since defective IL2 production and correction of functional T cell defects in vitro by hpIL2 have now been well documented in patients after BMT, in vivo administration of IL2 might be beneficial for these patients. In our ongoing phase I trial of hpIL2 in patients with other immunodeficiency states (AIDs, lymphoma) no side effects have been seen at up to 20,000 U/m$^2$ for 14 days [Mertelsman, R, et al. (1983) Proceedings of the UCLA Symposia on Molecular and Cellular Biology, Steamboat Springs 1983 (in press)]. However, in patients after BMT IL2 might enhance or cause acute GvHD. Animal studies have been initiated to address this problem.

What is claimed:

1. A method of normalizing a subject's immune response which comprises administering to the subject an amount of a human interleukin-2 effective to increase the proliferation of T cells and thus normalize the subject's immune response.

2. A method of claim 1, wherein the subject has an immunodeficiency.

3. A method of claim 2, wherein the immunodeficiency is a congenital immunodeficiency syndrome, Hodgkin's disease, Kaposi's Syndrome, or Nezeloff Syndrome.

4. A method of claim 2, wherein the immunodeficiency is caused by immunosuppression associated with chemotherapy, radiation therapy or bone transplantation therapy of cancer.

5. A method of claim 2, wherein the immunodeficiency is associated with Acquired Immune Deficiency Syndrome.

6. A method of claim 1, wherein the interleukin-2 is selected from the group consisting of interleukin-2s characterized by molecular weights of about 14,500±2,000, 16,000±1,000, 17,000±1,000, and 26,000±4,000 daltons as measured by gel filtration and sodium dodecyl sulfatepolyacrylamide gel electrophoresis.

7. A method of claim 6, wherein the interleukin-2 is further characterized by a specific activity of at least about 9×10$^5$ U/mg in the murine interleukin-2 dependent cytotoxic T-cell line assay.

8. A method of claim 2 which further comprises administering to the subject a lymphokine other than interleukin-2.

9. A method of claim 8, wherein the lymphokine is administered in combination with the human interleukin-2.

10. A method of treating a subject having an interleukin-2 dependent neoplasia which comprises administering to the subject an amount of a human interleukin-2 in combination with cytotoxin effective to inhibit growth of, or cause regression of, the neoplasia.

11. A method of claim 10, wherein the interleukin-2-dependent neoplasia is acute lymphocytic leukemia.

12. A method of claim 10, wherein the interleukin-2-dependent neoplasia is a neoplasia of mature T-cells.

13. A method of claim 10, wherein the interleukin-2 is selected from the group consisting of interleukin-2s characterized by molecular weights of about 14,500±2,000, 16,000±1,000, 17,000±1,000, and 26,000±4,000 daltons as measured by gel filtration and sodium dodecyl sulfatepolyacrylamide gel electrophoresis.

14. A method of claim 13, wherein the interleukin-2 is further characterized by a specific activity of at least about 9× 10$^5$ U/mg in the murine interleukin-2 dependent cytotoxic T-cell line assay.

15. A method of treating a subject having an overreactive immunity which comprises administering to the subject an amount of a human interleukin-2 effective to decrease the reactivity of the subject's immune system.

16. A method of claim 15, wherein the subject has an autoimmune disorder.

17. A method of claim 15, wherein the interleukin-2 is selected from the group consisting of interleukin-2s characterized by molecular weights of about 14,500±2,000, 16,000±1,000, 17,000±1,000, and 26,000±4,000 daltons as measured by gel filtration and sodium dodecyl sulfatepolyacrylamide gel electrophoresis.

18. A method of claim 17, wherein the interleukin-2 is further characterized by a specific activity of at least about 9×10$^5$ U/mg in the murine interleukin-2 dependent cytotoxic T-cell line assay.

19. A method of selectively eliminating interleukin-2 receptor-bearing cells from a subject which comprises administering to the subject an amount of a human interleukin-2 in combination with cytotoxin effective to selectively eliminate the interleukin-2 receptor-bearing cells.

20. A method of claim 19, wherein the interleukin-2 is selected from the group consisting of interleukin-2s characterized by molecular weights of about 14,500±2,000, 16,000±1,000, 17,000±1,000, and 26,000±4,000 daltons as measured by gel filtration and sodium dodecyl sulfatepolyacrylamide gel electrophoresis.

21. A method of claim 19, wherein the interleukin-2 is further characterized by a specific activity of at least about 9×10$^5$ U/mg in the murine interleukin-2 dependent cytotoxic T-cell line assay.

* * * * *